Figure 1:
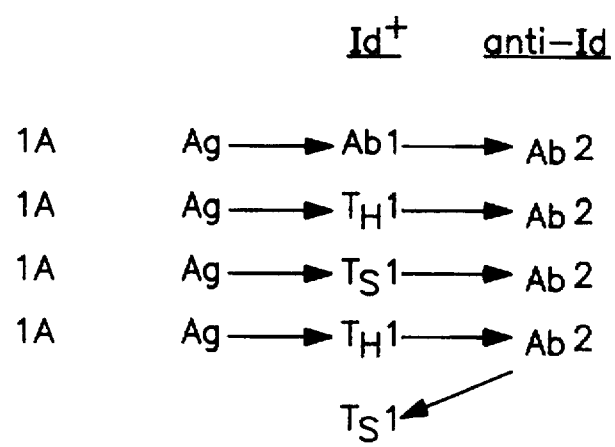

United States Patent [19]
Hellstrom et al.

[11] Patent Number: 5,766,588
[45] Date of Patent: Jun. 16, 1998

[54] TUMOR IMMUNOTHERAPY USING ANTI-IDIOTYPIC ANTIBODIES

[75] Inventors: Ingegerd Hellstrom; Karl Erik Hellstrom; Victor K. Lee. all of Seattle, Wash.

[73] Assignee: Oncogen. Seattle, Wash.

[21] Appl. No.: 532,443

[22] Filed: Sep. 22, 1995

Related U.S. Application Data

[63] Continuation of Ser. No. 096,095, Sep. 10, 1987, which is a continuation-in-part of Ser. No. 901,856, Aug. 28, 1986, abandoned.

[51] Int. Cl.$^6$ .................. A61K 39/00; A61K 39/395; C07K 16/00
[52] U.S. Cl. .................. 424/131.1; 435/327; 435/372.3; 530/387.2; 424/277.1; 424/93.7
[58] Field of Search .................. 424/131.1, 138.1, 424/154.1, 277.1, 93.7; 435/327, 372.3; 530/387.2

[56] References Cited

PUBLICATIONS

Hellstrom et al., Cancer Res. 45:2210–2218 (1985).
Flood et al., Proc. Natl. Acad. Sci. U.S.A. 77:2209–2213 (1980).
Binz et al., Int. J. Cancer 29:417–423 (1982).
Forstrom et al., Nature (London) 303:627–629 (1983).
Nepom et al., Proc. Natl. Acad. Sci. U.S.A. 81:2864–2867 (1984).
Holbeck and Nepom, J. Immunol. Methods 60:47–52 (1983).
Chapman, J. Urol. 88:518–526 (1962).
Halliday and Maluish InAssessment of Immune Status by the Leukocyte Adherence Inhibition Test, Thomson, ed., Academic, New York, pp. 1–26 (1982).
Koppi and Halliday, Cell. Immunol. 66:394–406 (1982).
Koppi and Halliday, J. Natl. Cancer Inst. 66:1089–1096 (1981).
Binz and Wigzell, J. Exp. Med. 142:197–211 (1975).
Hellstrom and Hellstrom, Adv. Cancer Res. 12:167–223 (1969).
Brawn, Int. J. Cancer 6:245–249 (1970).
Hellstrom et al., Int. J. Cancer 6:346–351 (1970).
Taranger et al., Science 176:1337–1340 (1972).
Halliday, et al., Cell. Immunol. 10:467–475 (1974).
Heberman, Ad. Cancer Res. 19:207–263 (1974).
Steele et al., J. Natl. Cancer Inst. 54:959–967 (1975).
Halliday, et al., Int. J. Cancer 16:645–658 (1975).
Thomson, Cancer Res/ 39:627–629 (1979).
Hellstrom et al., In Springer Seminars in Immunopathology: Mechanism of Host Resistance in Cancer, Baldwin, ed., Springer–Verlag, New York, pp. 127–146 (1982).
Hellstrom et al., Int. J. Cancer 29:175–180 (1982).

*Primary Examiner*—Lila Feisee
*Assistant Examiner*—Geetha P. Bansal
*Attorney, Agent, or Firm*—Brian W. Poor; Thomas R. Savitsky

[57] ABSTRACT

The present invention relates to methods which utilize anti-idiotypic antibodies, or fragments thereof, for tumor immunotherapy or immunoprophylaxis. Monoclonal anti-idiotypic antibodies which recognize an idiotype present on a second antibody or on a T lymphocyte or on an immune suppressor factor which is directed against a defined tumor antigen, can be used for immunization against a tumor, for immune anti-tumor activation or inhibition of suppression, or for in vitro activation of lymphocytes to be used in adoptive immunotherapy. The anti-idiotypic antibodies, or fragments thereof, can also be used to monitor anti-antibody induction in patients undergoing passive immunization to a tumor antigen by administration of anti-tumor antibody. In another embodiment, administration of T lymphocytes which express an idiotype directed against a defined tumor antigen can be used to transfer delayed-type hypersensitivity to the tumor. In another method of the invention, the induction of anti-idiotypic antibodies in vivo by administration of anti-tumor antibody or immune cells or factors exhibiting an anti-tumor idiotype can be therapeutically valuable.

21 Claims, 11 Drawing Sheets

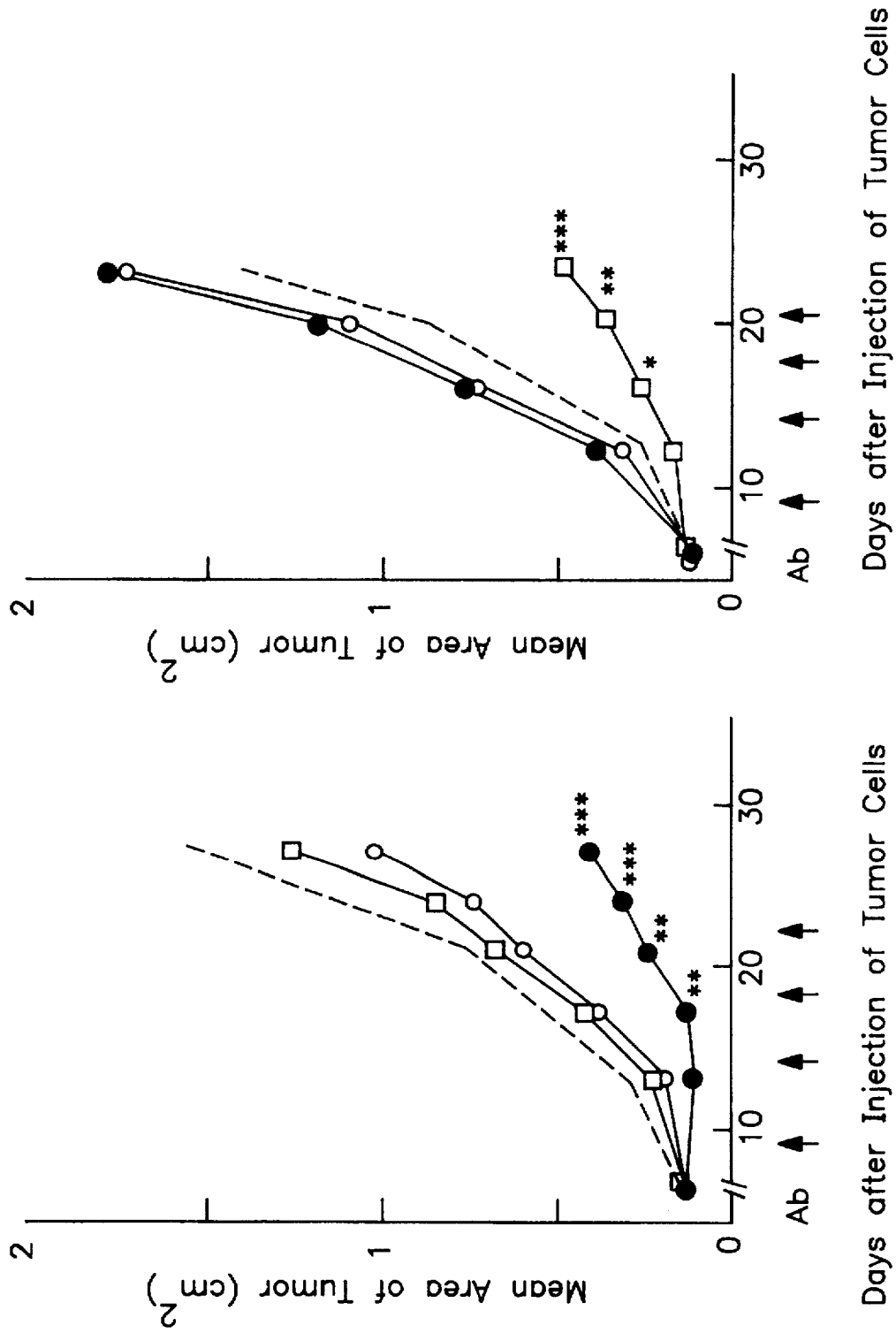

TUMOR IMMUNOTHERAPY USING ANTI-IDIOTYPIC ANTIBODIES

This application is a continuation of application Ser. No. 07/096,095, filed Sep. 10, 1987, which is a continuation-in-part of application Ser. No. 06,901,856, filed Aug. 28, 1986, abandoned.

1. FIELD OF THE INVENTION

The present invention is directed to methods which utilize anti-idiotypic antibodies for tumor immunotherapy and immunoprophylaxis. The invention relates to the manipulation of the idiotypic network of the immune system for therapeutic advantage, e.g. by use of anti-idiotypic antibody for immunization against tumor, for inhibition of immune suppression mediated by suppressor T cells or suppressor factors expressing an idiotope directed against a tumor antigen, for activation of lymphocytes used in adoptive immunotherapy, etc. In a specific embodiment, monoclonal anti-idiotypic antibodies which were raised against the idiotype of an antibody that defines a self-differentiation antigen, such as an oncofetal, or differentiation antigen, can be used in vivo to induce an immune response against tumors bearing the oncofetal antigen.

The anti-idiotypic monoclonal antibodies of the present invention will be valuable in tumor immunotherapy and immunoprophylaxis, and of general importance in human medicine. The molecules of the present invention may also be used as reagents in immunoassays such as ELISA tests and radioimmunoassays which are useful as diagnostic tools for the detection of anti-tumor antibodies or tumor antigens, and in immunoabsorption assays which are useful for the isolation and identification of antitumor antibodies. In addition, these reagents will be valuable tools in understanding the development and growth of neoplasia.

2. BACKGROUND OF THE INVENTION

2.1. ANTI-IDIOTYPIC ANTIBODIES

Anti-idiotypic antibodies or anti-idiotypes are antibodies directed against the antigen-combining region or variable region (called the idiotype) of another antibody molecule. In theory, based on Jerne's network model of idiotypic relationships (Jerne, N. K., 1974, Ann. Immunol. (Paris) 125c:373; Jerne, N. K., et al., 1982, EMBO 1:234), immunization with an antibody molecule expressing a paratope (antigen-combining site) for a given antigen should produce a group of anti-antibodies, some of which share with the antigen a complementary structure to the paratope. Immunization with a subpopulation of the anti-idiotypic antibodies should in turn produce a subpopulation of antibodies or immune cell subsets that are reactive to the initial antigen.

A network of idiotopes and anti-idiotopes has been invoked to explain immune regulation, with common or related idiotopes of antibodies, B lymphocytes, and various subsets of T lymphocytes and their soluble products interacting with anti-idiotopes (Jerne, N. K., 1974, supra; Urbain, J., et al., 1977, Proc. Natl. Acad. Sci. U.S.A. 74:5126; Rajewski, R. and Takemori, T., 1983, Ann. Rev. Immunol. 1:569). Studies which have been done on immunity to both haptens and viral antigens indicate that B cell derived anti-idiotypic antibodies can induce T cell responses (Rajewski, R. and Takemori, T., supra; Urbain, J., et al., supra; Binz, H. and Wigzell, H., 1978, J. Exp. Med. 147:63). For example, Ertl et al. immunized mice with a Sendai virus-specific T cell clone and produced an anti-idiotypic mAb which regulated the DTH response to Sendai virus (Ertl, H.C.J., et al., 1982, Proc. Natl. Acad. Sci. U.S.A. 79:7479). As evidence for a B cell antibody arising in response to a T cell idiotope, Kennedy et al. observed tumor rejection, but no antitumor antibodies, in mice treated with anti-idiotopic antibodies relating to the SV40 T antigen (Kennedy, R. C., et al., 1985, J. Exp. Med. 161:1432). The administration of exogenous anti-idiotypic antibody can exert enhancing or suppressive influences, dependent on, among other variables, the dose of the antibody (Reth, M., et al., 1981, Nature (London) 290:257).

2.2. TUMOR-ASSOCIATED ANTIGENS

A variety of tumor-associated antigens (TAA) have been described. One class of TAA is the tumor-specific transplantation type of cell-surface antigen (TSTA), which has been recognized by induction of immune responses in tumor transplant experiments.

Another class of TAA is the oncofetal or differentiation antigen. Oncofetal antigens are mainly embryonic or fetal cell products which are expressed by malignant cells due to derepression of the embryonic genes. One example of human oncofetal antigens are the carcinoembryonic antigens (CEA) of the colon. This set of antigens is found on tissues derived from the fetal gastrointestinal tract, and on tumors of the gastrointestinal tract. Alpha-fetoprotein is another known oncofetal antigen, which is secreted by hepatocarcinoma cells, as well as malignant yolk sac and fetal liver cells, and the proliferating fraction of adult liver cells.

A third class of TAA includes virally-induced tumor antigens. These include the T antigen induced by DNA tumor viruses, and the envelope antigens of RNA tumor viruses.

A variety of human cell-surface TAA has been detected in human neoplasms by mouse monoclonal antibodies (Hellstrom, K. E., et al., 1982, Human Tumor-Associated Antigens Identified by Monoclonal Antibodies, in, Springer Seminars in Immunopathology: Mechanism of Host Resistance in Cancer, Springer, New York, pp. 127–146; Herlyn, M., et al., 1984, in, Contributions to Oncology, Karger, Basel, Switzerland, Vol. 19 pp. 160–170). Many of these antigens are termed oncofetal, since they are expressed strongly by tumors and certain embryonic cells and much more weakly by normal cells from the adult host. Other tumor-associated antigens have been detected by their ability to stimulate host cell-mediated immunity (CMI) in human cancer (Hellstrom, K. E., and Hellstrom, I., 1969, Adv. Cancer Res. 12: 167–223; Halliday, W. J., and Maluish, A. E., 1982 in, Assessment of Immune Status by the Leukocyte Adherence Inhibition Test, Academic, New York pp. 1–26; Herberman, R. B., 1974, Adv. Cancer Res. 19: 207–263; Thomson, D. M. P., 1980, Cancer Res. 29: 627–629; Halliday, W. J., et al; 1975, Int. J. Cancer 16:645–654) and in tumor-bearing animals (Taranger, L. A., et al., 1972, Science 176: 1337–1340; Halliday, W. J., et al., 1974, Cell Immunol. 10:467–475; Steele, G., et al., 1975, J. Natl. Cancer Inst. 54: 959–967). Some of these antigens are also oncofetal, but their molecular nature and relationship to the antigens defined by mouse monoclonal antibodies are unclear.

Rat monoclonal antibodies to antigens shared by mouse bladder carcinomas have been obtained recently (Hellstrom, I., et al., 1982, Int. J. Cancer 29: 175–180; Hellstrom, I., et al., 1985, Cancer Res. 45: 2210–2218). One of the antibodies, 6.10, was shown to be specific for a bladder tumor oncofetal antigen (Hellstrom, I., et al., 1985, Cancer Res. 45:2210–2188).

2.3. IDIOTYPIC MANIPULATIONS OF TUMOR IMMUNITY

Several idiotypic manipulations of tumor immunity have been reported. Nepom et al. (1984, Proc. Natl. Acad. Sci. U.S.A. 81:2864–2867) described induction of tumor immunity where an oncofetal antigen was introduced into a xenogeneic host. Polyclonal anti-idiotypic antibodies were used to induce CMI in mice against a human melanoma-associated antigen. Forstrom et al. (1983, Nature (London) 303:627–629) used an anti-idiotypic antibody to induce CMI in mice to a syngeneic chemically induced sarcoma. In this study, the anti-idiotypic antibody was an auto-antibody produced by hyperimmunization to the tumor, and the tumor antigen was not a defined molecule. The studies of Flood et al. (1980, Proc. Natl. Acad. Sci. U.S.A. 77:2209–2213) and Binz et al. (1982, Int. J. Cancer 29:417–423) demonstrated idiotypic manipulations of tumor immunity in syngeneic systems, with undefined antigen molecules. Flood et al. showed evidence that murine anti-idiotypic T lymphocytes could participate in an autoimmune reaction to fibrosarcoma-specific T lymphocytes, and thus adversely affect an individual's immune response to a tumor. Binz et al. used anti-idiotypic antibodies to induce in vitro proliferation of T lymphocytes specifically cytotoxic to rat sarcoma cells.

Additional studies have looked at the effect of anti-idiotypic antibodies on tumor growth. Tilkin et al. (1981, Proc. Natl. Acad. Sci., U.S.A. 78:1809–1812) showed that immunization of mice with lymph node cells sensitized to an unidentified sarcoma antigen resulted in tumor rejection and growth inhibition. Kennedy et al. (1985, J. Exp. Med. 161:1432–1449) described the suppression of tumor formation in mice challenged with SV40-transformed cells, after injection with polyclonal anti-idiotypic antibodies related to the SV40 antigen.

Koprowski et al. (1984, Proc. Natl. Acad. Sci. U.S.A. 81:216–219) showed the presence of anti-idiotypic antibodies in patients who had a remission of carcinoma after administration of a monoclonal antibody directed against human gastrointestinal cancer.

2.4. SUPPRESSOR CELLS AND SUPPRESSOR FACTORS

The suppressor cell/factor cascade has been recognized in tumor and model systems (Nepom, G. T., et al, 1983, Experientia 39:235; Asherson, G. L., et al., 1984, Immunology 53:491; Dorf, M. E. and Benacerraf, B., 1984, Ann. Rev. Immunol. 2:127). Suppressor cells play an important role in regulating tumor immunity (Greene, M. I., et al., 1977, Proc. Natl. Acad. Sci. U.S.A. 74:5118; Hellstrom, K. E., et al., 1978, J. Exp. Med. 148:799; Nepom, G. T., et al., 1983 Experientia 39:235; North, R. J., 1982, J. Exp. Med. 155:1063; Yamauchi, K., et al., 1979, J. Immunol. 123:1653). Some of these cells produce suppressor factors (SF) (Nelson, K., et al., 1975, Int. J. Cancer 16:539; Greene, M. I., et al., 1977, J. Immunol. 119:759; Koppi, T. A. and Halliday, W. J., 1983, Cell. Immunol. 76:29) which can be detected in sera from tumor-bearing animals and human patients through the inhibition ("blocking") of in vitro manifestations of cell-mediated immunity (CMI) (Hellstrom, K. E., et al., 1978, J. Exp. Med. 148:799; Hellstrom, I., et al., 1969, Proc. Natl. Acad. Sci. U.S.A. 62:362; Baldwin, R. W., 1973, Adv. Cancer Res. 18:1; Halliday, W. J., et al., 1974, Cell. Immunol. 10:467; Steele, G., et al., 1975, J. Natl. Cancer Inst. 54:959; Hellstrom, K. E., et al., 1977, Biochim. Biophys. Acta 473:121; Halliday, W. J., et al., 1980, J. Natl. Cancer Inst. 65:327; Koppi, T. A. and Halliday, W. J., 1981, J. Natl. Cancer Inst. 66:1089; Kuchroo, V. K., et al., 1983, Cancer Res. 43:1325; Koppi, T. A., et al., 1981, J. Natl. Cancer Inst. 66:1097). Some SF have tumor specificity and can be removed from serum by absorption with the respective tumor or tumor-related antigen but not with tumors expressing different antigens (Kuchroo, V. K., et al., 1983, Cancer Res. 43:1325; Baldwin, R. W., 1973, Adv. Cancer Res. 18:1; Hellstrom, K. E., et al., 1977, Biochim. Biophys. Acta 473:121; Koppi-Reynolds, T. A. and Halliday, W. J., 1984, Immunol. Lett. 8:219). This suggests that there is a binding site or idiotope on SF molecules, complementary to the tumor antigen determinants (Nepom, G. T., et al., 1983, Experientia 39:235; Hellstrom, K. E., et al., 1977, Biochim. Biophys. Acta 473:121). It has been reported that circulating SF bind to antibodies from mice hyperimmunized with tumor cells, suggesting that the antibodies are complementary to idiotypic determinants on the SF (Hellstrom, K. E., et al., 1977, Biochim. Biophys. Acta 473:121; Nepom, G. T., et al., 1977, Proc. Natl. Acad. Sci. U.S.A. 74:4605); in these studies, both the antibody and suppressor cell responses were assumed to be polyclonal. Certain immune sera, obtained after tumor removal or regression, abrogate ("unblock") the antigen-specific suppressive ("blocking") activity of tumor-bearer sera as measured in vitro (Halliday, W. J., et al., 1974, Cell. Immunol. 10:467; Hellstrom, I. and Hellstrom, K. E., 1970, Int. J. Cancer 5:195). It has been theorized that this "unblocking" effect was mediated by anti-idiotypic antibodies (Hellstrom, K. E., et al., 1977, Biochim. Biophys. Acta 473:121). It was reported that "unblocking" antibodies had a therapeutic effect in rats with primary or transplanted polyoma virus-induced tumors (Bansal, S. C. and Sjogren, H. O., 1972, Int. J. Cancer 9:490; Sjogren, H. O. and Bansal, S. C., 1971, in Progress in Immunology, Amos, B., ed., Academic Press, New York, p. 921; Bansal, S. C. and Siogren, H. O., 1971, Nature (New Biol.) 233:76).

3. SUMMARY OF THE INVENTION

The present invention is directed to methods which utilize anti-idiotypic antibodies, or fragments thereof, for tumor immunotherapy and immunoprophylaxis. The invention relates to the manipulation of the idiotypic network of the immune system for therapeutic advantage. Particular embodiments include the use of anti-idiotypic antibodies for immunization against tumor, for activation of lymphocytes to be used in adoptive immunotherapy, and for inhibition of immune suppression mediated by suppressor T cells or suppressor factors expressing an idiotope directed against a tumor antigen. In specific embodiments, monoclonal anti-idiotypic antibodies, or fragments thereof, (a) which were raised against the idiotype of an antibody that defines a tumor antigen, such as an oncofetal or differentiation antigen, and (b) which exhibit tumor-specific properties such as induction of tumor-specific cell mediated immunity (as measured by various assays, e.g. the leukocyte adherence inhibition assay or the delayed-type hypersensitivity assay), inhibition of anti-tumor antibody binding, etc. are identified. The monoclonal anti-idiotypic antibodies, or fragments thereof, which demonstrate immunopotency can be used in vivo in a patient to induce an immune response directed against tumor cells that bear the tumor antigen. The anti-idiotypic antibodies, or fragments thereof, can also be used to monitor anti-antibody induction in patients undergoing passive immunization to a tumor antigen by administration of anti-tumor antibody.

In another embodiment, the induction of anti-idiotypic antibodies in vivo by administration of anti-tumor antibody or immune cells or factors exhibiting the anti-tumor idiotopes, can be of therapeutic value.

The invention is also directed to the monoclonal anti-idiotypic antibody molecules, antibody fragments, or chemically modified antibodies or fragments, which recognize an idiotype directed against a defined tumor antigen. The molecules of the invention may be produced by any technique known in the art, including the hybridoma technique originally described by Kohler and Milstein (1975, Nature 256:495–497), the human B-cell hybridoma technique (Kozbor et al., 1983, Immunology Today 4:72), and the EBV-transformation technique (Cole et al., 1985 Monoclonal Antibodies and Cancer Therapy, Alan R. Liss, Inc., pp. 77–96).

The invention is illustrated by way of examples in which anti-idiotypic antibodies are administered in mice to induce specific cell-mediated immunity to a murine bladder transitional cell carcinoma (BTCC) in the syngeneic hosts. The anti-idiotypic monoclonal antibody was obtained by immunization of mice with a rat monoclonal antibody directed against a murine BTCC antigen. Spleen cells from the mice were then fused with myeloma cells and screened for production of anti-idiotypic antibody by ELISA. The hybridoma was cloned and propagated, and the anti-idiotypic antibody tested for its ability to induce cell-mediated immunity (CMI) in naive mice. Assays for delayed-type hypersensitivity (DTH) in vivo and leukocyte adherence inhibition (LAI) in vitro demonstrated the induction of specific CMI to BTCC in response to the anti-idiotypic antibody.

In another example, monoclonal anti-idiotypic antibodies were used to reveal the expression of idiotopes specific to a murine bladder transitional cell carcinoma and idiotopes specific to a fibrosarcoma, on immune suppressor factors and suppressor T cells.

In a third example of the invention, serotherapy of mice by injection with anti-idiotypic antibodies related to a murine fibrosarcoma delayed the appearance and caused regression of transplanted sarcoma. A T cell line was established which expressed an idiotope directed against a fibrosarcoma, and which could transfer delayed-type hypersensitivity to the fibrosarcoma.

In another example of the invention, a mouse monoclonal anti-idiotypic antibody which is specific to an idiotype which recognizes a human melanoma-associated GD3 ganglioside antigen is described. The anti-idiotypic antibody was demonstrated to prevent binding of the anti-GD3 antibody to its antigen, and to inhibit both complement- and antibody-dependent cytotoxicity of the anti-GD3 antibody. By using the anti-idiotypic antibody as a probe, an assay was developed to monitor human antibodies to the anti-GD3 antibody in patients receiving the anti-GD3 antibody for therapeutic or diagnostic purposes.

The antibody molecules of the invention, fragments of the antibody molecules containing the idiotype of the molecules, or chemical modifications of these molecules can be used to assay for the presence of anti-tumor antibodies, tumor antigen by competition assays, and the induction of cell-mediated tumor immunity in immunoprophylactic and immunotherapeutic applications.

3.1. DEFINITIONS

As used herein, the following abbreviations will have the meanings indicated:
ADCC=antibody-dependent cellular cytotoxicity
BTCC=bladder transitional cell carcinoma
CDC=complement-dependent cytotoxicity
CMI=cell-mediated immunity
DTH=delayed-type hypersensitivity
FACS=fluorescence-activated cell sorter
FCS=fetal calf serum
FITC=fluorescein isothiocyanate
Id=idiotope
Ig=immunoglobulin
i.p.=intraperitoneal
i.v.=intravenous
kDa=kiloDalton
KLH=keyhole limpet hemocyanin
LAI=leukocyte adherence inhibition
mAb=monoclonal antibody
MCA=3-methylcholanthrene
PBS=phosphate buffered saline
PC=peritoneal cells
SC=spleen cell

4. DESCRIPTION OF THE FIGURES

FIG. 1. A schematic diagram of four types of idiotypic and anti-idiotypic responses initiated by antigenic stimuli. $T_H$ (FIG. 1B, 1D) or $T_S$ (FIG. 1C) substituting for Ab1 in the stimulation of anti-idiotypic antibody production is illustrated.

Figure 2:
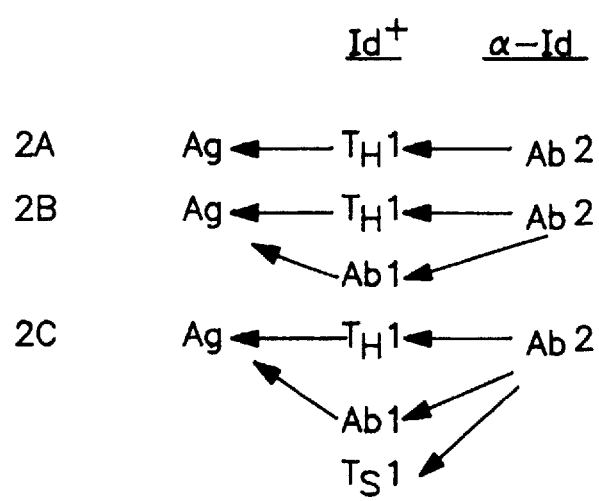

FIG. 2. A schematic diagram of three pathways by which Ab2 can induce antitumor immunity. FIG. 2A shows the induction of antigen specific $T_H$ upon immunization with Ab2. The elicitation of normally "silent" Ab1 specificities is illustrated (FIG. 2B), as is the triggering of $Id^+ T_S$ (FIG. 2C).

Figure 3:
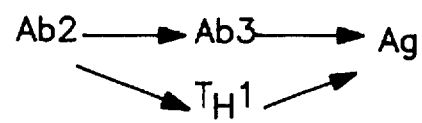

FIG. 3. A schematic diagram of immunization with internal-image anti-idiotypic antibody to elicit anti-antigen response.

Figure 4:
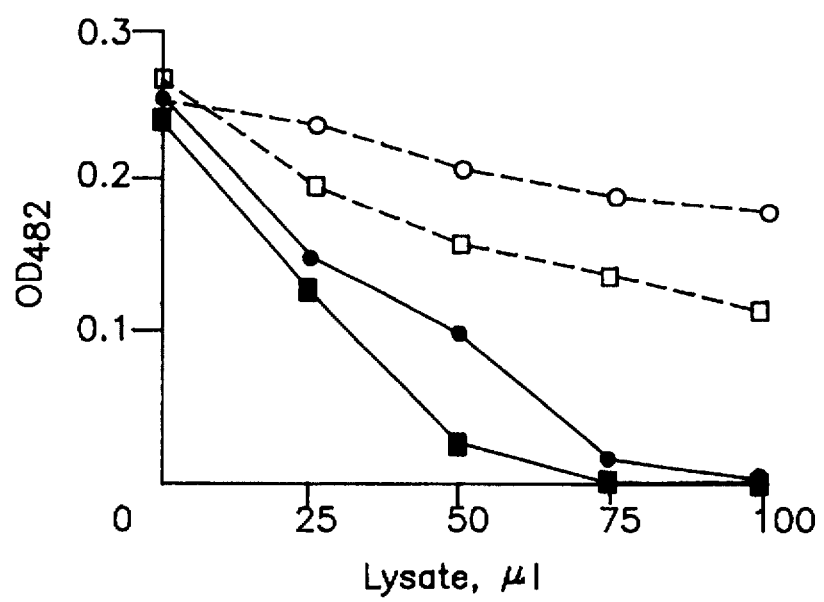

FIG. 4. Antibody 6.10 binding to antibodies 21D9 and 43A10 is inhibited by an antigen expressed by BTCC-1660. Limiting amounts of antibody 6.10 supernatant were added to polystyrene wells precoated with 2 mg of anti-idiotypic antibodies per ml in the presence of Nonidet P-40-soluble cell lysates. Closed symbols represent BTCC-1660 lysates and open symbols represent MCA-1511 lysates; squares represent an experiment with antibody 43A10 and circles represent an experiment with antibody 21D9. Peroxidase-conjugated rabbit anti-rat was added. $OD_{492}$ measures color development of the chromogen in the presence of bound peroxidase.

Figure 5A:
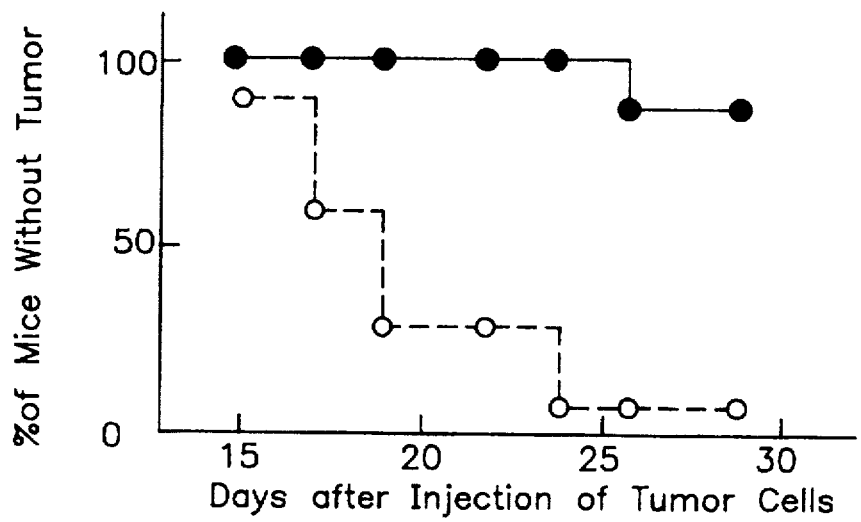
Figure 5B:
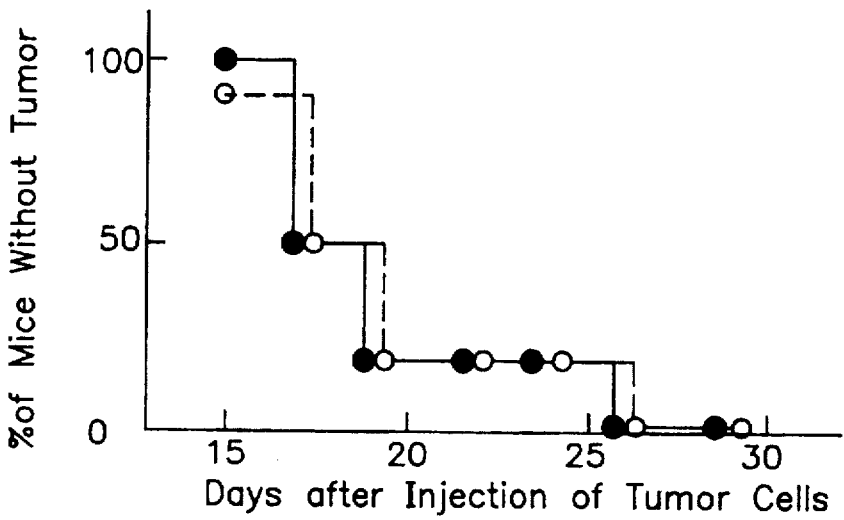
Figure 5C:
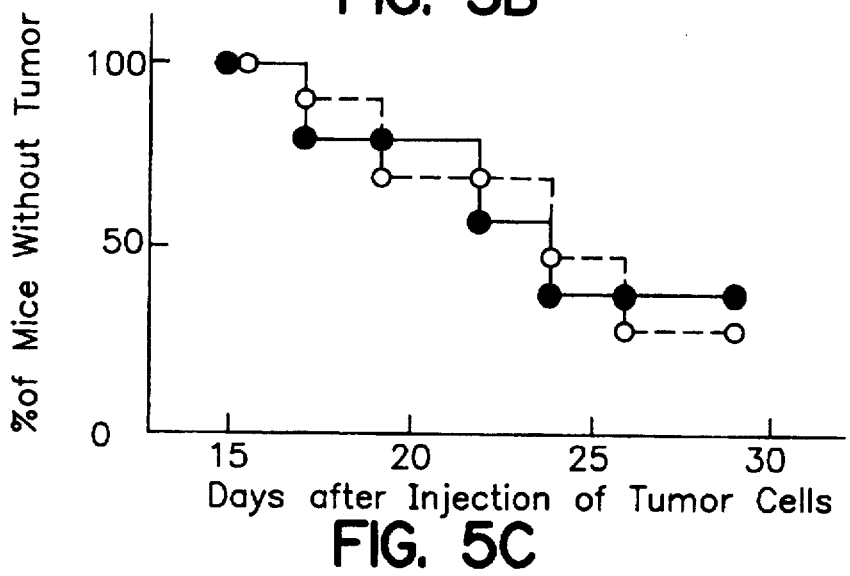

FIG. 5. T cells of line 90.3 (●—●) inhibit the growth of MCA-1490 (Panel A) but not MCA-1510 or MCA-1511 (Panels B and C). The growth of tumor mixed with control T cells (○—○) was used for comparison.

FIG. 6. Treatment of tumor-bearing mice with auto-anti-idiotypic mAb inhibits tumor growth. mAb were given intraperitoneally, on days 8, 13, 17, and 21. Tumor size is presented as the average area of the tumors for the 10 mice in each treatment group. Mice were treated with mnAb 4.72 (●—●), mAb 5.96 (□—□), mAb 8.2 (○—○) or PBS (———).

Difference significant at *p less than 0.05,p less than 0.01, *p less than 0.001.

Figure 7A:
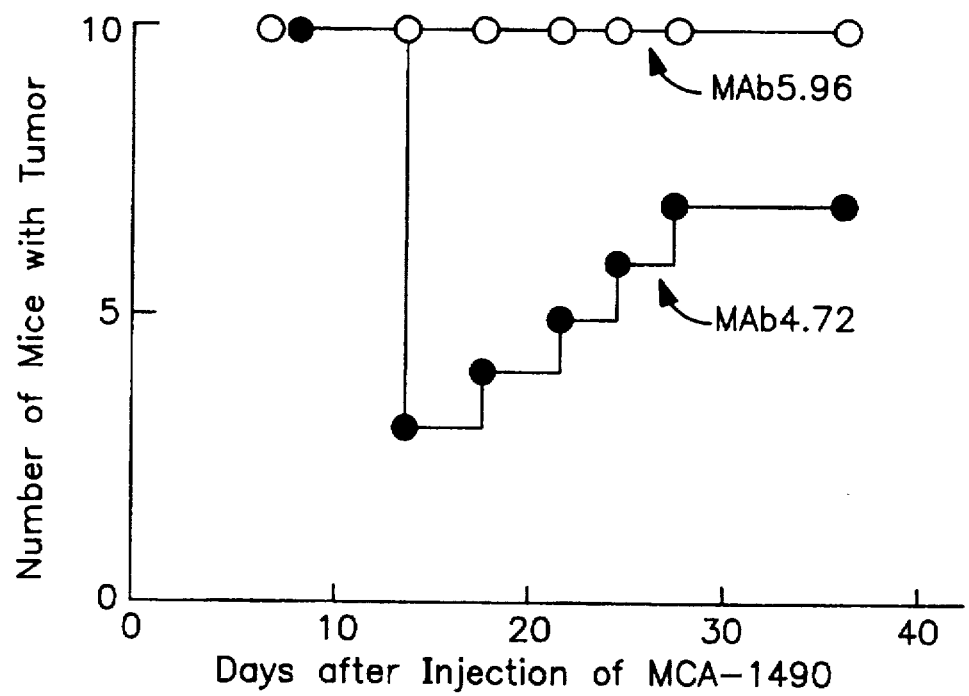
Figure 7B:
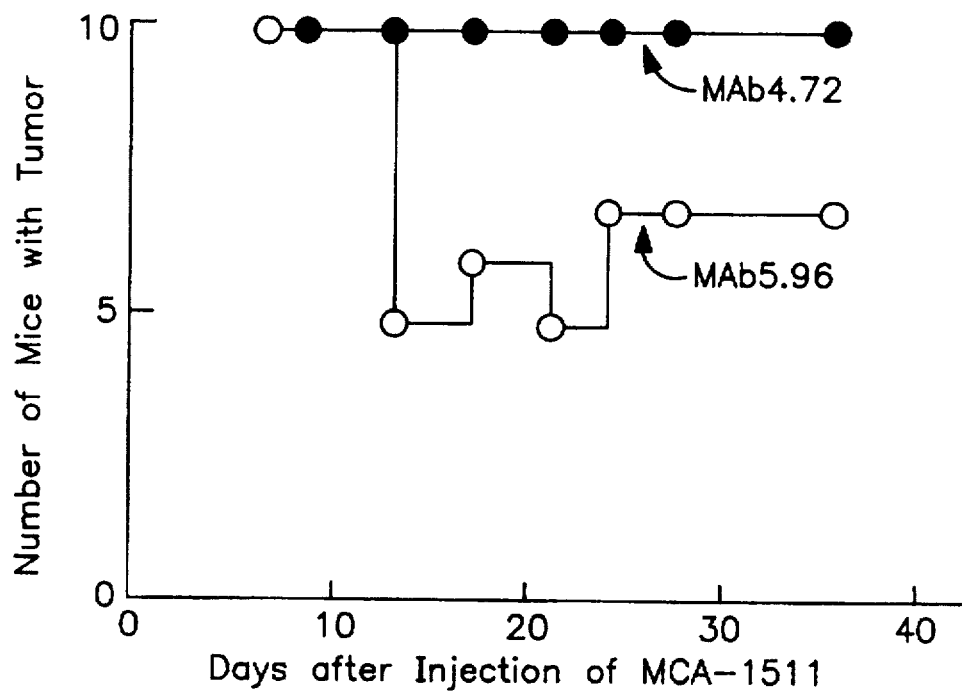

FIG. 7. Treatment of tumor-bearing mice with auto-anti-idiotopic monoclonal antibodies induces regression of growing sarcomas. The number of mice with tumors greater than 0.2 cm² after treatment with mAb 4.72 (●—●) or mAb 5.96 (○—○) is presented for tumor MCA-1490 (top panel) or MCA-1511 (bottom panel).

Figure 8:
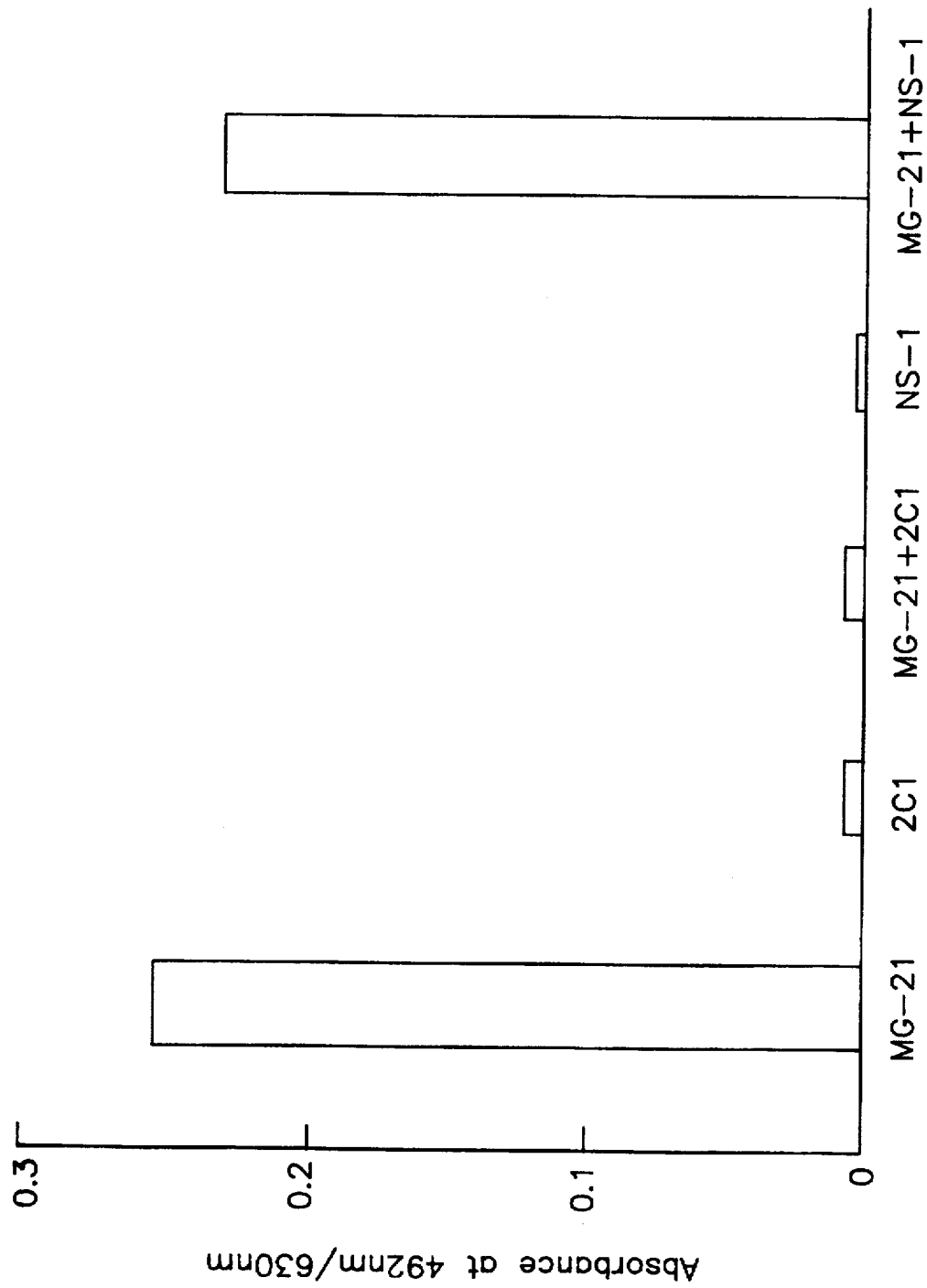

FIG. 8. Inhibition of mAb MG-21 binding to M-2669 clone 13 cells by culture supernatant of anti-idiotypic antibody-producing hybridoma 2C1.

Figure 9:
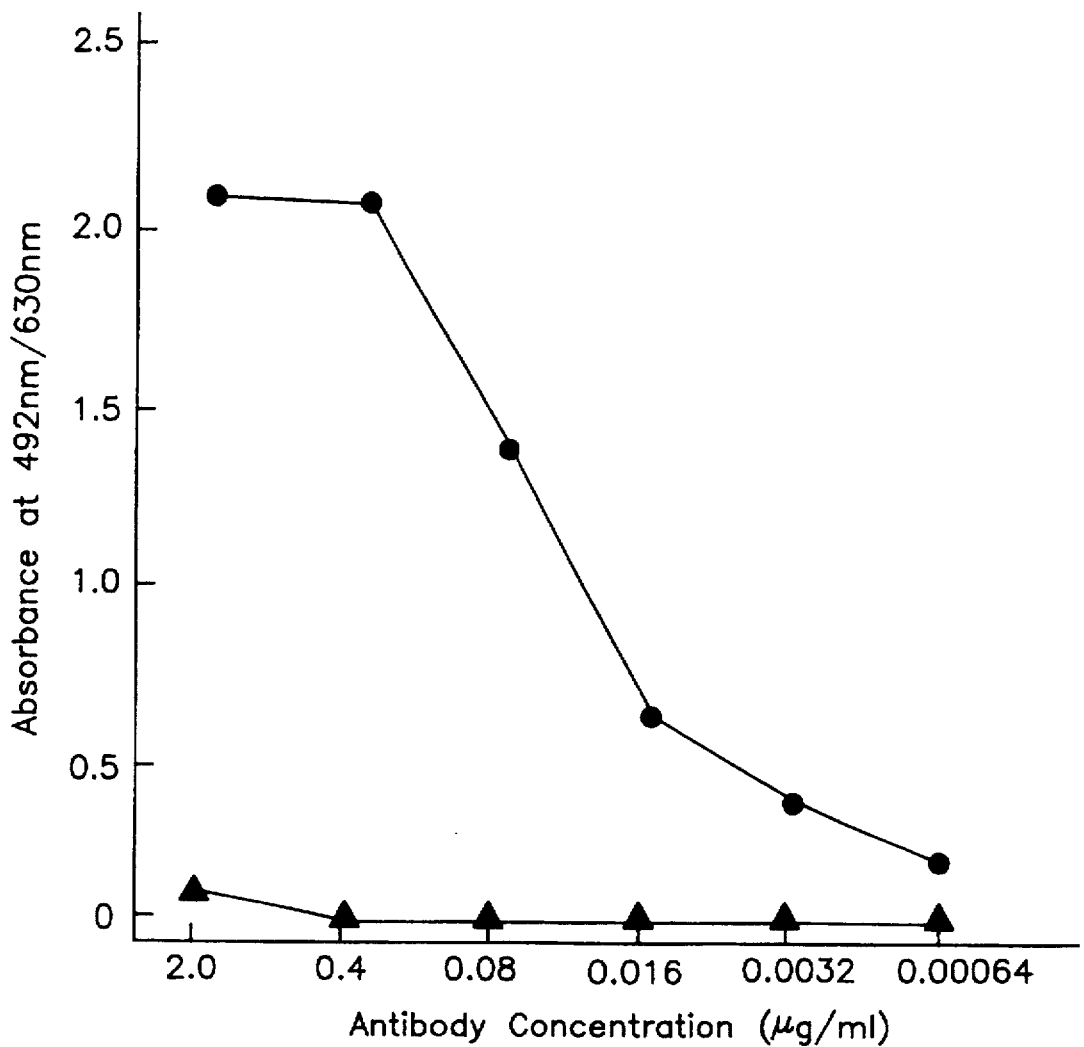

FIG. 9. Direct binding of monoclonal anti-idiotypic antibody 2C1 to mAb MG-21. Various concentrations of mAb 2C1 (●) or control immunoglobulin P1.17 (▲) were added to polyvinyl chloride wells precoated with mAb MG-21.

Figure 10:
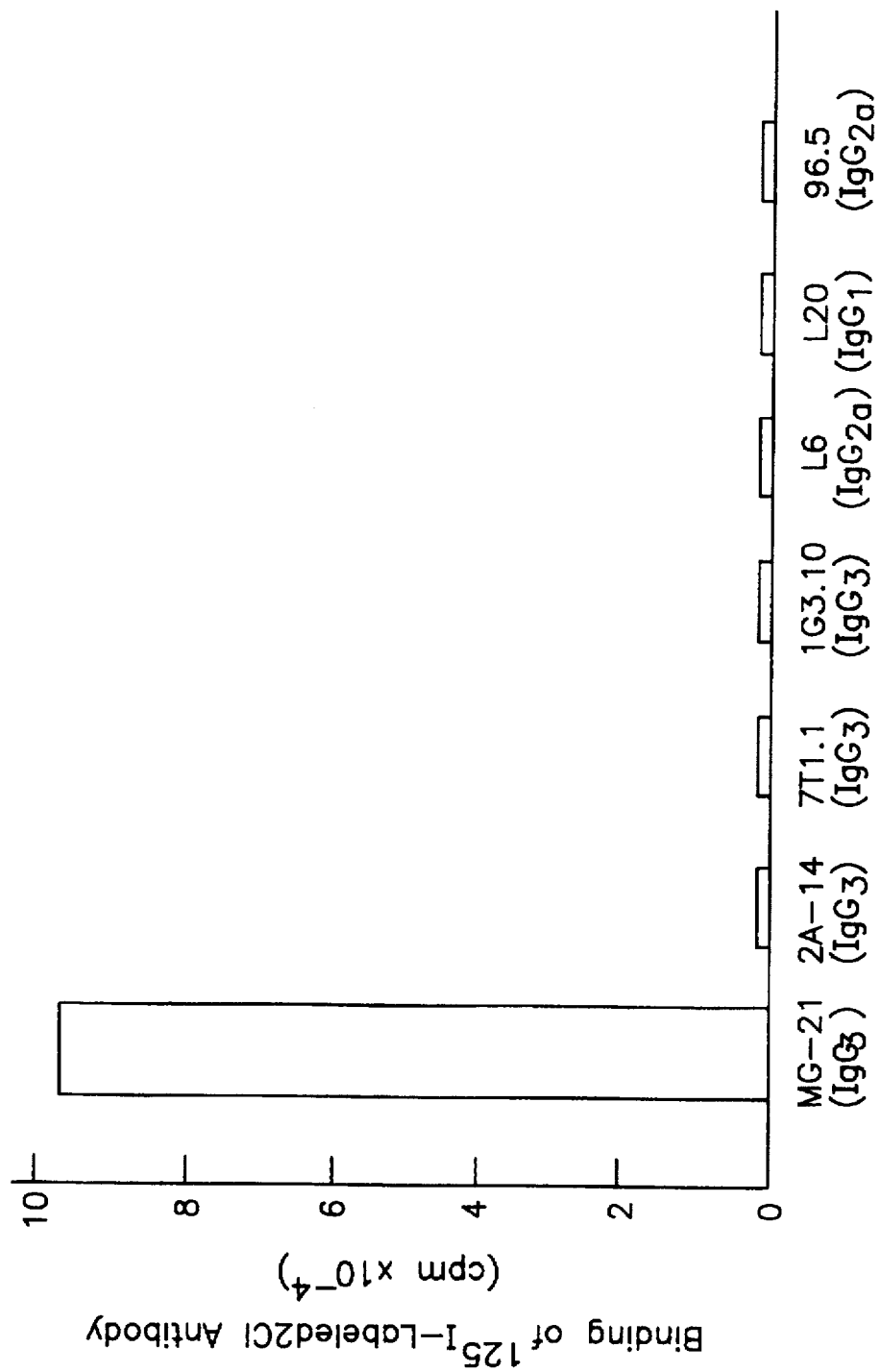

FIG. 10. Specificity of anti-idiotypic mAb 2C1 for MG-21 as compared to various mAbs.

Figure 11:
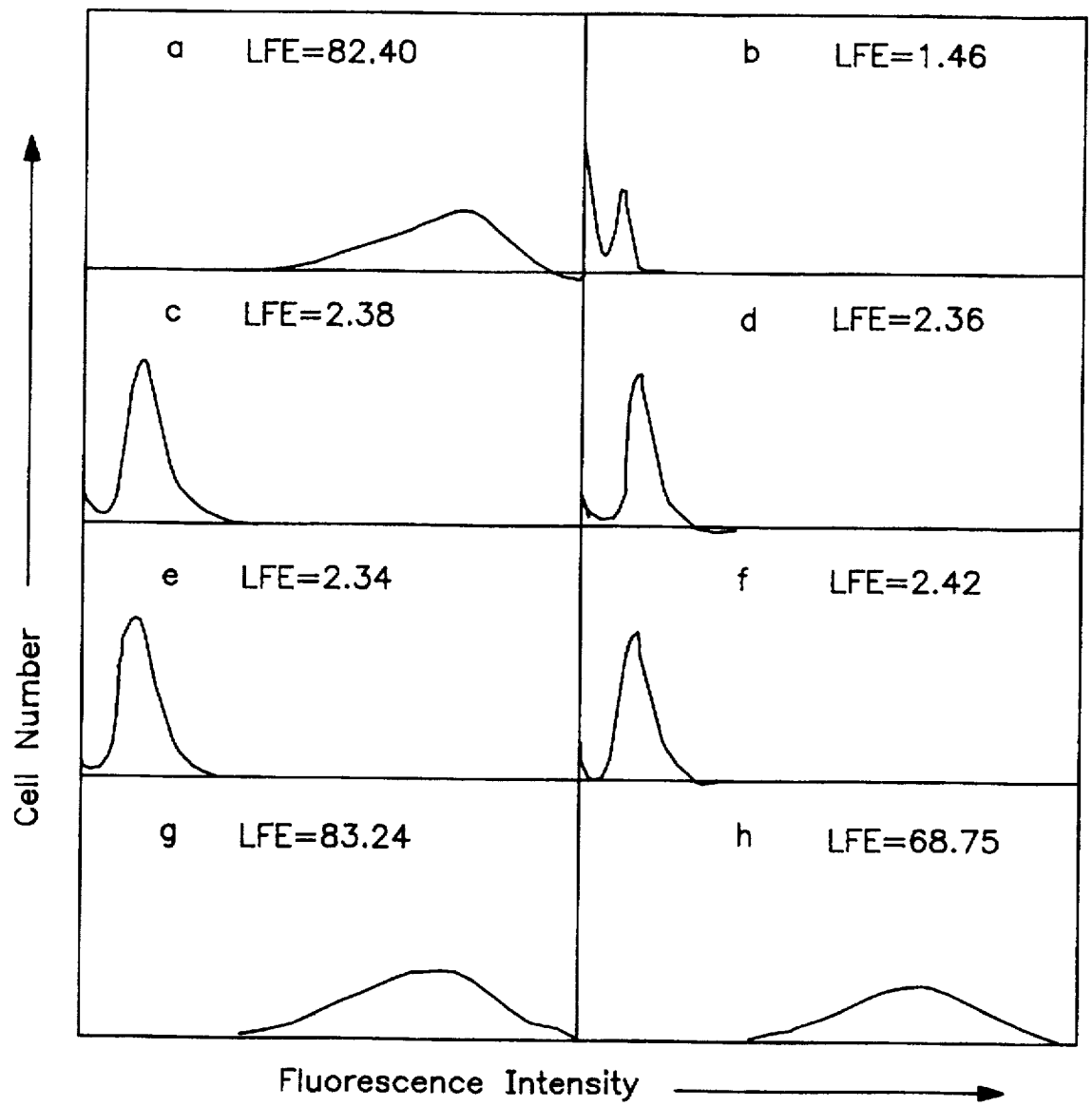

FIG. 11. Cell-sorting profiles of FITC-conjugated MG-21 against M-2669 cells in the presence or absence of mAb 2C1. Tumor cells were stained with FITC-conjugated MG-21 alone (40 ug/ml, panel a) or remained unstained to obtain the background level (panel b). Panels c through f show inhibition of staining with FITC-conjugated MG-21 in the presence of mAb 2C1 at different concentrations (panel c, 160 ug/ml; panel d, 80 ug/ml; panel e, 40 ug/ml; panel f, 20 ug/ml). Panels g and h show staining of FITC-conjugated MG-21 in the presence of mAb 26.8 (160 ug/ml) and P1.17 (160 ug/ml).

5. DETAILED DESCRIPTION OF THE INVENTION

The present invention is directed to methods which utilize anti-idiotypic antibodies for tumor immunotherapy and immunoprophylaxis. The invention relates to the manipulation of the idiotypic network of the immune system for therapeutic advantage. Immunization with anti-idiotypic antibodies (Ab2) can induce the formation of anti-anti-idiotypic immunoglobulins, some of which have the same antigen specificity as the antibody (Ab1) used to derive the anti-idiotype. This creates a powerful paradigm for manipulation of immune responses by offering a mechanism for generating and amplifying antigen-specific recognition in the immune system. An immune response to tumors appears to involve idiotype-specific recognition of tumor antigen; the present invention relates to strategies for manipulating this recognition towards achieving therapeutic benefit. Particular embodiments of the invention include the use of anti-idiotypic antibody for immunization against tumor, for activation of lymphocytes used in adoptive immunotherapy, and for inhibition of immune suppression mediated by suppressor T cells or suppressor factors expressing an idiotope directed against a tumor antigen. The anti-idiotypic antibodies, or fragments thereof, can also be used to monitor anti-antibody induction in patients undergoing passive immunization to a tumor antigen by administration of anti-tumor antibody.

In a specific embodiment, the induction of anti-idiotypic antibodies in vivo, by administration of anti-tumor antibody or immune cells or factors exhibiting the anti-tumor idiotope, can be of therapeutic value.

In another embodiment of the present invention, monoclonal anti-idiotypic antibodies, or fragments thereof, raised against the idiotype of an antibody that defines a self-differentiation antigen, such as an oncofetal, or differentiation antigen can be administered in vivo to induce a specific immune response directed against tumor cells that bear the oncofetal antigen. Patients having tumors may be immunotherapeutically treated with the monoclonal anti-idiotypic antibodies of the present invention whereas patients identified as having a predisposition may be so treated immunoprophylactically.

The present invention is also directed to anti-idiotypic mAb molecules, or fragments of the anti-idiotypic mAb molecules, or modifications thereof, that recognize an idiotype that is directed against a defined antigen specific for a tumor. Such tumor antigens include antigens of fibrosarcoma, self-differentiation antigens such as oncofetal, or differentiation, antigens which are expressed by malignant cells, including but not limited to oncofetal antigens such as carcinoembryonic antigens (CEA) of the colon, alpha-fetoprotein, the human antigenic counterpart or functional equivalent of the 175 kDa murine antigen of transitional cell bladder carcinomas, the melanoma associated antigen p97 or GD3, and differentiation antigens of human lung carcinomas such as L6 and L20, described in more detail infra.

The mAb molecules of the present invention include whole monoclonal antibody molecules and fragments or any chemical modifications of these molecules, which contain the antigen combining site that binds to the idiotype of another antibody molecule(s) with specificity to a defined tumor antigen. Monoclonal antibody fragments containing the idiotype of the mAb molecule could be generated by various techniques. These include, but are not limited to: the $F(ab')_2$ fragment which can be generated by treating the antibody molecule with pepsin, the Fab' fragments which can be generated by reducing the disulfide bridges of the $F(ab')_2$ fragment, and the 2Fab or Fab fragments which can be generated by treating the antibody molecule with papain and a reducing agent to reduce the disulfide bridges.

Depending upon its intended use, the molecules of the invention may be chemically modified by the attachment of any of a variety of compounds using coupling techniques known in the art. This includes but is not limited to enzymatic means, oxidative substitution, chelation, etc., as used, for example, in the attachment of a radioisotope for immunoassay purposes.

The chemical linkage or coupling of a compound to the molecule could be directed to a site that does not participate in idiotype binding, for example, the $F_c$ domain of the molecule. This could be accomplished by protecting the binding site of the molecule prior to performing the coupling reaction. For example, the molecule can be bound to the idiotype it recognizes, prior to the coupling reaction. After completion of coupling, the complex can be disrupted in order to generate a modified molecule with minimal effect on the binding site of the molecule.

The antibodies, or fragments of antibody molecules of the invention, can be used as immunogens to induce, modify, or regulate specific cell-mediated tumor immunity. This includes, but is not limited to, the use of these molecules in immunization against syngeneic tumors.

The method of the invention may be divided into the following stages solely for the purpose of description: (a) production of anti-idiotypic mAb(s) (which may be auto-anti-idiotypic) directed against an idiotype which binds a defined antigen of a tumor; (b) evaluation and demonstration of tumor idiotype specificity of the anti-idiotypic mAb molecules or their derivative fragments, for example, by demonstration of immunopotency by induction of specific CMI, of binding to specific suppressor T cells or suppressor factors, of binding to specific helper T cells, of inhibition of the binding of antibody directed against the tumor antigen, of inhibition of the cytotoxicity properties of the antibody directed against the tumor antigen, etc.; and (c) formulation of immunoprophylactic, immunotherapeutic, and immunodiagnostic regimens.

In a model system described in a specific example of the present invention, murine monoclonal anti-idiotypic antibodies were produced which recognize the idiotype directed against an oncofetal antigen of mouse transitional cell bladder carcinomas. These antibodies were shown to induce specific CMI when injected into naive mice. In another example of the invention, a murine tumor (bladder carcinoma or fibrosarcoma)-specific idiotope on suppressor factors and suppressor T cells was capable of being specifically bound, and suppression blocked, by the appropriate anti-idiotypic antibody. In a third example of the invention, treatment of mice with auto-anti-idiotypic antibodies related to a fibrosarcoma antigen was shown to specifically reduce the growth of established sarcomas. In yet another example of the invention, a murine monoclonal anti-idiotypic antibody which recognizes an idiotype directed against a GD3 ganglioside antigen of human melanoma is described. This antibody was able to block the binding and cytotoxicity properties of the antibody containing the idiotype which it recognizes. However, the methods described are not limited to bladder carcinoma or melanoma or fibrosarcoma antigens, but can be applied to the production and use of anti-idiotypic mAbs related to any specific tumor antigens.

The use of anti-idiotypic antibodies to induce immune responses to tumors can be viewed as two separate issues. First, such antibodies may be used to select or amplify a pre-existing antitumor repertoire, that is, to recruit, via idiotypic selection, T and/or B cells with specificity for tumor antigen. Second, anti-idiotypic antibodies can be employed as "internal images" of antigens to induce a primary immune response which is anti-anti-idiotypic, and a portion of which is directed against the nominal tumor antigen. In the latter case, the immune specificity will be against anti-idiotope, rather than antigen.

By using anti-idiotypic antibodies to induce immunity, T and B cells may be selected which are different from those which participate in a naturally occurring antitumor response, either as a result of upregulation of an immune response that is normally suppressed or by the de novo induction of a response. Of significant therapeutic importance is the potential to induce effective antitumor reactivity in hosts which are otherwise incapable of mounting such reactivity.

5.1. IDIOTYPIC INTERACTIONS INITIATED BY ANTIGENIC STIMULI

In order to effect therapeutic manipulations of the idiotypic recognition of tumor antigens, one must consider the nature of the naturally occurring idiotypic response to a growing syngeneic tumor. We shall thus discuss the nature of the idiotypic repertoire in the response to stimulation with any antigen.

Four possible idiotypic and anti-idiotypic responses which can be induced by antigens are illustrated in FIG. 1. FIG. 1A shows a sequential progression of induced complementary specificities. In this type of idiotypic cascade, immunization with antigen leads to a population of immunoglobulins which carry distinct idiotypes, the sum of which is known as the idiotype or Ab1 response. The presence of the Ab1 then induces an anti-idiotypic response, characterized by a heterogeneous population of antibodies, known as Ab2, which have specificity for the various idiotopes in the Ab1 population. Directionality of the antigen-elicited response is implied by the arrows in FIG. 1. The induction of Ab2 by Ab1 is independent of antigen (Urbain, J., et al., 1982, Ann. Immunol. 133D:179–189; Rodkey, L. S., 1974, J. Exp. Med. 139:712; Kelsoe, G. and Cerny, J., 1979, Nature 279:333). There is support for this model (FIG. 1A) in tumor immunity (Lee, V. K., et al., 1986, Biochim. Biophys. Acta 865:127–139; see examples sections infra).

An idiotypic cascade may also lead to the generation of Ab2 according to the pathway shown in FIG. 1B. Tumor antigen recognition induces antigen-specific $T_H$ cells, which bear particular idiotopes, presumably on their antigen receptor molecules. These T cells then stimulate the generation of an anti-idiotypic immunoglobulin response in the form of a population of Ab2.

What are the implications of a model in which the idiotypic cascade proceeds through alternate antibody and T cell components? In an analysis of idiotopes associated with the response to MCA-induced mouse sarcomas or carcinomas (Lee, V. K., et al., 1986, Biochim. Biophys. Acta 865:127–139; see examples sections 6.7.8, infra), immunization with monoclonal Ab2 failed to generate Ab3 with Ab1-like specificity, whereas antitumor $T_H$ were easily induced. This observation, coupled with the finding of idiotype-positive $T_H$ in the naturally occurring antitumor response, supports a model in which there can be a direct regulatory interaction between Id+ T cells and anti-idiotypic B cells (and Ab2) (Nelson, K. and Nepom, G. T., 1986, in Paradoxes in Immunology, Hoffman, G., et al., eds., CRC Press, Boca Raton, Fla., pp. 177–185; Bismuth, G., et al., 1984, Eur. J. Immunol. 14:503; Thomas, W. R., et al., 1983, J. Immunol. 130:2079). In vivo, the Id+ T cells can provide the stimulus for production of anti-idiotype.

The lack of Id+ B cell recognition in certain cases, may reflect a defect in the genetic capacity to generate antitumor idiotopes on immunoglobulin molecules; alternatively, the regulatory state in the tumor-bearing host may effectively suppress Id+ Ab1. As discussed infra (see Section 5.2.1), this apparent defect may be circumvented therapeutically in a host which does not normally develop Id+ antibody responses.

In addition to idiotypic interactions which result in a $T_H$ response leading to tumor rejection, exposure to tumor antigen (or antigen-antibody complexes) can lead to the generation of antigen-specific suppressor T cells ($T_S$) (FIG. 1C). In several tumor systems, suppressor T cells have been shown to function as inducer cells, triggering and amplifying tumor antigen-specific suppression (Nepom, G. T., et al., 1983, Experientia 39:235–242). If Id+ $T_S$ are directly induced by antigen stimulation, as in the model shown in FIG. 1C, it is possible that these cells, like the $T_H$ in FIG. 1B, can serve as stimuli for the generation of anti-idiotypic Ab2.

In a model where idiotypic $T_S$ are generated subsequent to stimulation by antigen, an alternate pathway can also be considered. As diagrammed in FIG. 1D, Id+ $T_S$ may arise as a consequence of anti-idiotypic stimulation. In a recent analysis of IgH-restricted T cell responses to the hapten azobenzenearsonate, the nature of immunoglobulin idiotopes was found to determine the development of $T_S$ idiotopes (Hayglass, K., et al., 1986, J. Exp. Med. 164:36–49; Hayglass, K., et al., 1986, Immunol. Today 7:179–183). T cells developing in IgH congenic mice acquired the idiotypic repertoire of the host, and treatment of neonatal animals with antibodies to the u immunoglobulin chain abolished the establishment of a normal repertoire of functional T cell idiotypes. Thus, the immunoglobulin compartment could determine the development of complementary T cell recognition elements.

As illustrated by the examples sections infra, the idiotypic pathway depicted in FIG. 1D appears to exist also in the context of tumor antigen recognition. In our studies on mice which had either sarcomas or bladder carcinomas induced with MCA, a single dominant T cell idiotope was found to be prevalent in the suppressor response mediated by both $T_S$ and soluble factors (see examples sections 7.8, infra). That is, instead of a heterogeneous mixture of idiotypes, some shared "public" idiotopes predominate. This was documented by removing suppressor factors using affinity absorbents made from either monoclonal or polyclonal anti-idiotypic antibodies. Our findings indicated that most of the apparent idiotypic specificities in the suppressor response to any particular tumor antigen are shared.

In model systems, the presence of "public" idiotopes has been attributed to regulatory idiotopes important for network interactions (Bona, C., et al., 1982, J. Exp. Med. 156:986). The presence of such putative regulatory idiotopes in anti-tumor immunity may reflect either a genetic selection in the generation of idiotypic $T_S$, or an influence of immunoglobulin selection in the generation of the $T_S$ repertoire. If the latter is the case, the induction of idiotypic $T_S$ can include the pathway we have shown in FIG. 1D, in which the Ab2 response influences the nature of $T_S$.

5.2. MANIPULATION OF IDIOTOPE EXPRESSION BY ANTI-IDIOTYPIC ANTIBODIES

There are essentially two approaches for using anti-idiotypic antibodies to manipulate the immune response to tumor antigens for therapeutic benefit. One is based on selecting and amplifying pre-existing antitumor idiotopes within the T and B cell repertoires, and the other entails the priming of a de novo response using an anti-idiotype which acts as an internal image of tumor antigen.

5.2.1. SELECTION AND AMPLIFICATION OF PRE-EXISTING ANTITUMOR IDIOTOPES

In the therapeutic production of anti-idiotypic antibodies based on an alteration of preexisting antitumor idiotope representation, therapeutic efforts are based on a reversal of the pathways illustrated in FIG. 1, in which the Ab2 compartment is used as the initiator of idiotypic interactions.

Three pathways by which Ab2 can induce tumor antigen-specific immunity are illustrated in FIG. 2. FIG. 2A shows that immunization with Ab2 can lead to the development of antigen specific $T_H$. This result has been accomplished against infectious agents and found to give protection from disease (Sacks, D., et al., 1982, J. Exp. Med. 155:1108; Sharp, A., et al., 1984, J. Exp. Med. 160:1195–1205; Fons, G., et al., 1985, J. Immunol. 134:1225–1229). Analogous findings have been made for several chemically and virally-induced tumors (Kennedy, R. C., et al., 1985, J. Exp. Med. 161:1432; Binz, H., et al., 1982, Int. J. Cancer 19:417–423; Tilken, A. F., et al., 1981, Proc. Natl. Acad. Sci. U.S.A. 78:1809; Flood, P., et al., 1980, Proc. Natl. Acad. Sci. U.S.A. 77:2209–2213). The Ab2 which is utilized can arise as a result of an antigen-induced idiotypic cascade, or can be induced by immunization with antigen-specific T cells (see Section 5.3, infra).

Anti-idiotypic antibodies can also stimulate "silent" clones; i.e., clones which are normally suppressed even in genetically competent individuals (Bona, C. A., et al., 1981, J. Exp. Med. 153:951). Thus, the anti-idiotypic antibodies appear to be able to "reprogram" the immune system to generate antibodies which would not otherwise be made (FIG. 2B). Thus, immunization with anti-idiotypic antibodies related to capsular polysaccharides of *E. coli* produces protective immunity in neonatal mice that do not normally develop antibodies against the capsular polysaccharides (Stein, K., et al., 1984, J. Exp. Med. 160:1001).

For Ab2 to select and stimulate both id+ B and T cell clones, it is probable that shared idiotopes between B and T cell receptors must exist (Rajewski, K. and Takemori, T., 1983, Ann. Rev. Immunol. 1:569–607; Ertl, H. C. J., et al., 1982, Proc. Natl. Acad. Sci. U.S.A. 79:7479; Nadler, P. I., et al., 1982, Eur. J. Immunol. 12:113), and correspond to antigen-specific receptors which confer the same antigen specificity for both B and T cells. In a preferred embodiment of the invention, one can select for use in immunization those Ab2 which induce T cell immunity, in which a T cell subset is stimulated which mediates the desired response. One technique to select appropriate Ab2 for use is to raise Ab2 experimentally by immunization with antigen-specific T cells (Infante, A. J., et al., 1982, J. Exp. Med. 155:1100). In this particular embodiment of the invention, the T cell receptor is used as the stimulatory idiotype so that the Ab2 population will be targeted specifically to the T cells of choice. Immunization with such an Ab2, then, will select and stimulate T cell clones which share receptor idiotopes with the immunizing cells.

Several investigators have reported successful cloning of tumor-infiltrating T lymphocytes recovered from tumor biopsies or surgical specimens. These lymphocytes, after culture in vitro with IL-2, are effective in eliciting antitumor responses when reinfused to the host (Rosenberg, S. A., et al., 1986, Science 233:1318). In a preferred embodiment of the invention, such cells should be ideal immunogens for raising Ab2 directed against the particular idiotopes associated with such antitumor clones. These Ab2, then, would serve as anti-idiotypes which potentially will select and amplify T cells with similar antitumor specificity.

As discussed supra, anti-idiotypic specificities in tumor-immunized mice appear to be complementary not only to $T_H$ but also to $T_S$ and soluble suppressor factors (Hellstrom, K. E., et al., 1977, Biophys. Biochim. Acta Reviews on Cancer 473:121–148; see Section 8, infra; Binz, H., et al., 1982, Int. J. Cancer 19:417–423; Tilken, A. F., et al., 1981, Proc. Natl. Acad. Sci. U.S.A. 78:1809; Flood, P., et al., 1980, Proc. Natl. Acad. Sci. U.S.A. 77:2209–2213). The evidence that anti-idiotypic antibodies recognize a dominant public idiotope on T -derived factors suggests that there is a regulatory relationship between the id+ cellular compartment and the Ab2 compartment (see Sections 7.8, infra; Nelson, K. and Nepom, G. T., 1986, in Paradoxes in Immunology, Hoffman, G., et al., eds., CRC Press, Boca Raton, Fla., pp. 177–185). Thus, in order to avoid the preferential activation of the $T_S$ compartment upon administration of anti-idiotypic antibodies (as illustrated in FIG. 2C), and in order to achieve a therapeutically effective result, anti-idiotypic therapy for cancer should employ proper manipulation of the idiotypic networks. Proper manipulation involves the consideration of three issues: the genetic restriction between anti-idiotype and the T cell compartment; the route of anti-idiotype administration; and the choice of idiotope specificity.

5.2.1.1. GENETIC RESTRICTION

Two types of genetic restriction can potentially present barriers to cellular recruitment by injected anti-idiotypes: MHC restriction and IgH restriction. MHC restriction confers an element of genetic control of T cell activation in an antigen-specific response. To the extent that an anti-idiotype mimics antigen in the recognition process, it is logical to consider possible requirements for histocompatibility. Indeed, examples have been reported in which antigen-primed T cells are MHC restricted not only for their specific antigen recognition, but also for their ability to recognize cell-bound anti-idiotype in vitro (Ertl, H., et al., 1986, Int. Rev. Immunol. 1:61–66).

What are the implications of these findings for the in vivo administration of anti-idiotype? In a study using anti-idiotype priming to generate anti-viral immunity, a genetically non-restricted response was observed (id.). This may have been due to the direct recruitment of $T_H$ which subsequently activated other T cell compartments. Thus, even if the MHC restricting element for anti-Id presentation is different from that of nominal antigen presentation, T cell recruitment can still occur. With an appropriate route of administration (see below), anti-idiotypic antibodies can be introduced to the immune system by antigen-presenting cells in such a way that they may be "seen" in the context of the right restriction elements. In fact, a host which is a genetic non-responder to the nominal antigen can conceivably respond to challenge with anti-idiotype, depending on the mechanism maintaining the non-responsiveness. Thus, MHC restriction appears to be of minor importance except where cell-bound anti-idiotype is used. In a preferred embodiment of the invention, anti-idiotype administration should seek to optimize the presentation of the Ab2 immunogen to the host immune system, even where MHC-incompatible.

In a preferred embodiment of the invention, the issue of IgH restriction, i.e., the necessity for genetic matching of allotypic markers associated with immunoglobulin genes, should be considered. Since variable region antibody genes are linked to constant region genes, the genetic potential for specific idiotypic determinants is linked to Ig allotypic markers. IgH restriction appears to govern many steps in the idiotypic cascade (Bach, B. A., et al., 1979. J. Exp. Med. 149:1084; Nadler, P. I., et al., 1982, Eur. J. Immunol. 12:113; Yamamoto, H., et al., 1983, J. Exp. Med. 158:635–640; Forstrom, J. W., et al., 1983, Nature 303:627–629). In essence, it acts as a permissive barrier which requires the presence of appropriate V genes, and linked allotypic markers, for idiotype-anti-idiotype recognition.

A strict IgH restriction of the immune response to Ab2 likely reflects requirements for direct recognition of network V genes; this has been referred to as a "true idiotypic" interaction (Nisonoff, A. and Lamoyi, E., 1981, Clin. Immunol. Immunopathol. 21:397). This requirement limits the type of antibody which can be used as an anti-idiotype immunogen, to one which can elicit complementary V genes in the host. Thus, in a particular preferred embodiment of the invention, experimentally derived anti-idiotypic antibodies should be IgH-matched with the host.

When is IgH-matching for anti-idiotypic administration not necessary? Anti-idiotypic antibodies which act as internal images of the nominal antigen can substitute for this immunization with antigen. Since such de novo immunization is not based on specific selection of network V genes, internal image immunogens are generally not IgH restricted (id.), and thus do not need to be host IgH-matched.

5.2.1.2. ROUTE OF IMMUNIZATION

The route of immunization with anti-idiotype can also influence the nature of the immune response. Depending upon the route of administration, anti-idiotypic antibodies have been found to either enhance or suppress immune responses (Rajewski, K. and Takemori, T., 1983, Ann. Rev. Immunol. 1:569; Urbain, J., et al., 1982, Ann. Immunol. 133D:179). For example, in a viral system, reovirus-specific immunity could be established following immunization against idiotypic determinants, and DTH, cytolytic T cells, and antigen-binding antibodies were observed. If soluble Ab2 was used as the immunogen, only the DTH response was seen, while immunization with cell-associated anti-idiotype, in the form of a hybridoma-producing Ab2, also induced cytolytic T cells (Ertl, H., et al., 1986, Int. Rev. Immunol. 1:61–66). When Ab2 is used as an internal-image immunogen (as in the reovirus system), it essentially substitutes for antigen in the initial priming; many of the immune manipulations which facilitate antigen responsiveness also augment immunity to Ab2 and can be used in various embodiments of the invention (see Section 5.3.2, infra).

Many methods may be used to introduce the immunizing formulations; these include but are not limited to intradermal, intramuscular, intraperitoneal, intravenous, subcutaneous, and intranasal routes. In particular embodiments, induction of immunity with anti-idiotypic antibodies can utilize subcutaneous (s.c.) or intramuscular injection of the antibodies in the presence of various adjuvants.

In the case of nominal antigen immunization, administration of a haptenated protein s.c. with adjuvant has been shown to yield a vigorous $T_H$ response, while the same antigen intravenously (i.v.) preferentially induced $T_S$ (Greene, M., et al., 1982, Adv. Immunol 32:253). However, when monoclonal antitumor antibodies were used therapeutically, the opposite situation was reported by Koprowski et al. (Koprowski, H., et al., 1984, Proc. Natl. Acad. Sci. U.S.A. 82:216–219), who described an anti-idiotypic response to systemically injected mouse antibodies to human gastrointestinal cancer, which was apparently accompanied by a therapeutic effect in the patient.

There is also evidence that Ab2 can effectively inhibit the ability of an Ab1 to mediate antibody-dependent cellular cytotoxicity or kill tumor cells in the presence of complement (see Section 9.2.4, infra).

Since route of Ab2 administration, as well as dosages used, are likely to have an important impact on what kind of response is induced, in a preferred aspect of the invention, preliminary studies on dosage and administration effects should be carried out. These studies can be done in an animal model such as mouse, rat, primate, etc. For example, in a particular embodiment, various routes of administration of anti-idiotypic antibody related to the melanoma antigen p97 can be tested for the in vivo and in vitro responses which they induce upon challenge with a mouse melanoma line expressing the p97 antigen (obtained following transfection with the cloned p97 gene; see copending U.S. application Ser. No. 827,313, filed Feb. 7, 1986; Brown et al., 1981, J. Immunol. 127:539–546).

5.2.1.3. IDIOTOPE SPECIFICITY

Complex antigens, including tumor antigens, contain multiple epitopes. The immune recognition which they evoke, therefore, contains many idiotopes which are determined not only by the heterogeneity of the epitopes, but also by the heterogeneity of the V genes selected among Ig and T cell receptor genes in the host. These idiotopes are largely defined by the anti-idiotopes which they induce. Thus private idiotopes elicit Ab2 responses which are unique for a particular Ab1, public idiotopes elicit Ab2 to a specificity shared by many Ab1, and Ab2 of the internal image type are induced against antigen-binding structures on Ab1 which are complementary to the antigen (Urbain, J., et al., 1982, Ann. Immunol. 125C:373–389; Augustin, A., et al., 1983, Surv. Immunol. Res. 2:78; Mosier, D. and Feeney, A., 1984, in The Biology of Idiotypes, Greene, M. and Nisonoff, A., eds., Plenum Press, New York, pp. 403–416).

In particular embodiments of the invention, likely shifts in the idiotypic repertoire can be manipulated in an attempt to achieve the desired idiotypic response. For example, idiotope selection depends in large part on the Ab2 used as immunogen. Thus, in a preferred embodiment, an Ab2 used as immunogen is one determined to be likely to cause the expression of therapeutically desirable idiotopes. For example, in a system with a dominant public idiotope on both $T_H$ and $T_S$ cells, anti-idiotypic antibodies may prime for $T_H$, if administered s.c. with adjuvant, or they may interact with soluble $T_S$ factors. As an illustration, in studies in mice which were immune to haptens and in which public idiotopes were recognized, a dominant Ab1 response with a shared public idiotope elicited a strong anti-Id response in mice of IgH-compatible strains. If anti-Id was given i.v. in neonates, or if anti-Id $T_S$ were transferred, the public Ab1 idiotope was suppressed, and this was shown to cause the expression of alternate idiotopes on antigen-specific Ab1 (Kekoe, G., et al., 1980, Immunol. Rev. 52:75). When immunization with anti-Id is applied towards tumor therapy, a similar shift in the idiotypic repertoire can occur.

In a system lacking a dominant public idiotope, or when no Ab1 is identified, the adaptability of the idiotope selection process offers encouraging alternatives. In a particular embodiment of the invention, since administration of Ab2 can select for alternate idiotypic responses, antibodies to idiotopes which do not occur naturally in the tumor-bearing host can be chosen to direct an antitumor response. In other words, one can immunize with an Ab2 which selects a $T_H$ repertoire which cannot be selected by exposure to tumor antigen. For example, one can immunize with a monoclonal, internal-image Ab2 raised against a xenogeneic antitumor antibody. Many of the existing monoclonal antitumor antibodies are, indeed, specific for antigens which may not even be immunogenic in the tumor-bearing host (Hellstrom, K. E. and Hellstrom, I., 1985, in Monoclonal Antibodies for Tumour Detection and Drug Targeting, Baldwin, R. W. and Byers, V. S., eds., Academic Press, London, pp. 17–51), and can be used in this embodiment of the invention.

5.2.2. INTERNAL IMAGE ANTIBODIES

Ab2 immunization can lead to Ab3 elicitation not only through specific V gene network interactions but also by virtue of internal-image mimicry (Urbain, J., et al., 1982, Ann. Immunol. 133D:179–189; Augustin, A., et al., 1983, Surv. Immunol. Res. 2:78). That is, when the anti-idiotype represents the conformational mirror-image of the antigen, it can substitute for nominal antigen and elicit an Ab1-like response (Nisonoff, A. and Lamoyi, E., 1981, Clin. Immunol. Immunopathol. 21:397) (FIG. 3). In a preferred embodiment, therefore, such anti-idiotypic antibodies can be used as immunogens for tumor therapy in IgH-mismatched hosts.

In an embodiment of the invention employing monoclonal anti-idiotypes, the appropriate Ab2 should be carefully selected. The experimental verification that any particular Ab2 is an internal image type of anti-idiotype hinges on its ability to mimic the conformational characteristics which define recognition of the antigen. Internal image anti-idiotypes compete in vitro with antigen for binding to idiotype-positive Ab1, and prime in vivo for Ab3 which mimic Ab1, and this priming occurs in a IgH unrestricted fashion (Nisonoff and Lamoyi, supra).

In addition to the inhibition of id+ binding to antigen, internal image Ab2 can substitute for antigen in terms of immune recognition. For example, Ab2 may stimulate antigen-specific clones in vitro in the absence of antigen, or Ab2+ cells may serve as a target for antigen-specific CTL (Ertl, H. C. J., et al., 1982, Proc. Natl. Acad. Sci. U.S.A. 79:7479). Since the Ab2 is substituting for antigen conformation, the Ab2 may be "presented" to T cells in these assays in the context of MHC molecules, and therefore the response can appear to be MHC restricted, just as for antigen-specific response (id.).

In an embodiment of the invention in which internal image immunogens are desired, xenogeneic anti-idiotypic antibodies may be used. It is possible that internal image immunogens fail to stimulate suppressor cells, while at the same time inducing $T_H$. This supposition is based on the notion, outlined in FIGS. 1D and 2C, that regulatory idiotopes which are represented by the expression of dominant V genes determine the communication between Ab2 and $T_S$, and that some anti-idiotypic antibodies may be selected which lack this particular idiotope yet retain the internal-image characteristics priming for $T_H$.

In a specific embodiment of the invention, internal image antibodies with tumor antigen activity can be used as tumor "vaccines" towards induction of specific tumor immunity. For example, such vaccines can be therapeutically valuable for patients whose primary neoplasms have been removed but who are at risk for development of metastases.

The ability of internal image Ab2 to compete with antigen for binding to Ab1 (and vice versa) is an integral part of their behavior. However, Ab2 which do not function as internal images may still compete, due to steric hindrance (and perhaps other mechanisms as well). In a preferred aspect of the ability of one should investigate the ability of an Ab2 to induce an immune response over IgH (and MHC) barriers in experimental animals as part of their characterization as potential internal images.

Since, on occasion, the distinction between internal-image anti-Id and "true" anti-Id becomes blurred, anti-idiotypic antibodies which do not have internal image specificity may still display internal image-associated properties, which can be therapeutically valuable. For example, in our study of monoclonal anti-idiotypes raised against a murine bladder carcinoma antigen-associated monoclonal antibody, immunization with the anti-idiotypes elicited a vigorous Ab3 response which lacked any detectable antigen-binding (Lee, V. K., et al., Biochim. Biophys. Acta 865:127–139). The Ab3 raised against a particular anti-Id were apparently directed against "private" specificities associated with that anti-idiotype. Although the anti-idiotypic antibodies were shown to inhibit antigen binding by the Ab1, this was presumed due to steric inhibition, and we tentatively interpreted these data to mean that the Ab2 were not internal image antibodies. Surprisingly, however, these same monoclonal Ab2 were able to prime mice for antitumor responses and also to bind to tumor-specific T cell suppressor factors (See examples Sections 6, 7, infra). Since the anti-idiotypic monoclonal antibodies in these experiments were raised in mice, and were directed against xenogeneic antitumor monoclonal antibodies raised in rats, the antitumor response elicited in mice by Ab2 immunization would not be expected to be based on specific V gene selection, and could instead be attributed to some internal image Ab2.

A second example comes from experiments analyzing idiotypic responses to TMV-associated antigens, in which mice were immunized with rabbit anti-idiotypic antibodies which were specific for "pravate" rabbit idiotopes (Francotte, M. and Urbain, J. 1984, J. Exp. Med. 160:1485). Surprisingly, these mice made anti-TMV antibodies which were idiotypically cross-reactive with the rabbit idiotopes. Thus, while the stimulatory anti-idiotype was not an "internal image" specificity, it nevertheless elicited antigen-specific information in the face of apparent V gene incompatibility.

5.3. PRODUCTION OF ANTI-IDIOTYPIC MONOCLONAL ANTIBODIES SPECIFIC TO AN IDIOTYPE WHICH RECOGNIZES A DEFINED TUMOR ANTIGEN

5.3.1. PRODUCTION OF ANTI-IDIOTYPIC MONOCLONAL ANTI-BODIES BY IMMUNIZATION WITH AN ANTIBODY (AB1) THAT RECOGNIZES A DEFINED TUMOR ANTIGEN

In a specific embodiment of the invention, production of anti-idiotypic monoclonal antibodies specific to an idiotype which recognizes a defined tumor antigen requires immunization of a host with antibodies that recognize the defined tumor antigen. As previously explained, such tumor antigens include but are not limited to oncofetal, or differentiation, antigens such as CEA, alpha-fetoprotein, the human antigenic functional equivalent of the 175 kDa murine antigen of transitional cell bladder carcinoma defined in the examples herein, melanoma associated antigen p97 (see Brown et al., 1981, J. Immunol. 127:539–546 and copending U.S. patent application Ser. No. 827,313 filed Feb. 7, 1986 which are incorporated by reference herein), differentiation antigens of human lung carcinoma such as L6 and L20 (see Hellstrom et al., 1986, Cancer Res. 46:3917–3923 and copending U.S. patent applications Ser. No. 834,172 filed Feb. 26, 1986, Ser. No. 776,321, filed Oct. 18, 1985, Ser. No. 684,759 filed Dec. 21, 1984, which are incorporated by reference herein), and the differentiation antigen associated with human melanoma, GD3 ganglioside antigen (see copending U.S. patent applications Ser. No. 831,684 filed Feb. 21, 1986, and Ser. No. 834,162 filed Feb. 20, 1986, which are incorporated by reference herein), antigens of fibrosarcoma, and the like.

The possible host species include but are not limited to experimental animals such as mice, rabbits, and chimpanzees; and humans. Various adjuvants can be used to enhance the immunological response to the antibodies, depending on the host species and including but not limited to, mineral gels, e.g., aluminum hydroxide; surface active substances such as lysolecithin; pluronic polyols; polyanions; peptides; oil emulsions; and potentially useful human adjuvants such as BCG (bacille Calmette-Guerin) and corynebacterium parvum. The Ab2 can also be coupled to an immunogenic carrier, including but not limited to LPS, or cross-linked with glutaraldehyde (Primi, C.D., et al., 1982, J. Immunol. 129:1124–1129). The immunogen may also be incorporated into liposomes, or conjugated to polysaccharides and/or other polymers, or otherwise chemically modified for use. Allotypic determinants on the Ab2 molecule itself can also be used to enhance immunogenicity. In the reovirus system, when the immunization with Ab2 crossed allotypic barriers, that is, when the host was IgH mismatched, a vigorous Ab3 response was seen (Ertl, H., et al., 1986, supra). This result suggests that Ig allotypic determinants on the anti-idiotype acted as helper determinants towards augmenting the immune responses. Thus, in a particular embodiment, IgH mismatching may be used to enhance immunogenicity.

The anti-idiotypic antibodies, or fragments of the anti-idiotypic antibodies, or chemically modified fragments or antibodies may be used for immunization. In addition, a mAb fragment containing the idiotype of the mAb molecule could be used, including but not limited to the $F_V$, Fab, Fab', or $F(ab')_2$ fragments, which can be generated by known techniques.

The monoclonal antibody can be prepared by using any technique which provides for the production of antibody molecules by continuous cell lines in culture. These include but are not limited to the hybridoma technique originally described by Kohler and Milstein (1975, Nature 256:495–497), and the more recent human B-cell hybridoma technique (Kozbor et al., 1983, Immunology Today 4:72) and EBV-transformation technique (Cole et al., 1985, Monoclonal Antibodies and Cancer Therapy, Alan R. Liss, Inc., pp. 77–96). Selection of the hybridoma can be carried out by any of numerous assays, e.g. for binding to Ab1, or for inhibition of Ab1 binding to tumor cells (Nepom, G. T., et al., 1984, Proc. Natl. Acad. Sci. U.S.A. 81:2864–2867; Holbeck, S. L. and Nepom, G. T. 1983, J. Immunol. Methods 60:47–52; see Section 9.1.7, infra).

5.3.2. PRODUCTION OF ANTI-IDIOTYPIC MONOCLONAL ANTIBODIES WHICH ARE DIRECTED AGAINST AN IDIOTOPE ON T CELLS THAT RECOGNIZES A DEFINED TUMOR ANTIGEN

In another specific embodiment of the invention, an anti-idiotypic antibody is produced, which is related to a tumor antigen, and which is directed against an idiotope associated with T cells that recognizes the tumor antigen. The idiotope may also be associated with suppressor factors that exhibit the idiotope directed against the tumor antigen. Such tumor antigens include but are not limited to those listed in Section 5.3.1, supra. In one embodiment (see Section 8, infra), the anti-idiotypic antibody can be produced by immunization with tumor antigen, formation of hybridomas, and screening for auto-anti-idiotypic monoclonal antibodies by methods including but not limited to assay of tumor-specific DTH, tumor-specific LAL binding to monoclonal antibody directed against the tumor antigen, etc. In particular embodiments, the tumor antigen used for production of auto-anti-idiotypic antibody can be specific to fibrosarcoma, transitional cell bladder carcinoma; it can be melanoma antigen p97 or GD3, or human lung carcinoma antigen L6 or L20. Alternatively, T cells ($T_H$ or $T_S$) or suppressor factors which bind tumor antigen can be used to immunize a host for the production of the anti-idiotypic antibody. In particular embodiments, T cells which express an idiotope defined by an antibody specific to fibrosarcoma, transitional cell bladder carcinoma, p97 melanoma antigen, GD3 melanoma antigen, L6 or L20 lung carcinoma antigen, may be used for immunization. Since injection of $T_S$ cells may be therapeutically detrimental, immunization with $T_H$ cells is preferred. The T cells used for immunization may be obtained, for example, from the tumor-carrying patient himself or from an appropriate (preferably histocompatible) donor whose immune system has been exposed to the tumor antigen. The T cells can then be isolated for injection by various techniques known in the art, e.g. fluorescence-tagged monoclonal anti-tumor antibody binding and FACS. (See Section 8.4, infra). Suppressor factors for immunization can be isolated by many techniques known in the art, including but not limited to immunoaffinity chromatography (to a tumor-antigen coated column), generation of T—T hybridomas by fusing T cells from tumor-bearing hosts (Nelson, K. A., et al., 1980, Proc. Natl. Acad. Sci. U.S.A. 77:2866) followed by screening e.g. for suppression of DTH to tumor antigen, specific binding to tumor antigen, etc. (see Section 8.5, infra).

5.4. EVALUATION AND DEMONSTRATION OF IMMUNOPOTENCY BY INDUCTION OF TUMOR-SPECIFIC CMI

Where the anti-idiotypic antibody of the invention is envisioned for use in immunization against tumors (see Section 5.6.1, infra), in a preferred embodiment, the immunopotency of the antibody should be tested. Any method which can demonstrate immunopotency of the anti-idiotypic molecule by showing induction of tumor-specific CMI upon immunization with the anti-idiotypic antibody or its derivative fragment(s) is within the scope of the invention for evaluation of the immunopotency of the anti-idiotypic mAb; such assays include, but are not limited to DTH (for a description of the DTH assay procedure see Forstrom et al., 1983, Nature (London) 303:627–629) and/or LAI (Halliday, W. J. & Maluish, A. E., 1982, in Assessment of Immune Status by the Leukocyte Adherence Inhibition Test, Academic, New York pp. 1–26; Koppi, T. A., and Halliday, W. J., 1982, Cell. Immunol. 66:394–406; Koppi, T. A., and Halliday, W. J., 1981, J. Natl. Cancer Inst. 66:1089–1096). Further specificity testing, as described in the model detailed in the examples herein, can include but is not limited to immunoabsorption assays and treatment of peritoneal cells with antibodies and complement.

5.5. FURTHER CHARACTERIZATION OF ANTI-IDIOTYPIC ANTIBODY

In order to further determine anti-idiotypic antibody specificity, Ab1 binding assays and/or assays of inhibition of Ab1-tumor binding may be carried out. Such assays may be accomplished by any methods known in the art, e.g. those described in Section 9, infra. Two additional assays that may be done include tests of inhibition of complement-dependent cytotoxicity or antibody dependent cellular cytotoxicity properties of Ab1 (see Sections 9.1.1.3 and 9.1.1.4 infra).

5.6. USES IN IMMUNOPROPHYLAXIS, IMMUNOTHERAPY, AND IMMUNOASSAY

The purpose of this embodiment of the invention is to describe uses of the anti-idiotypic antibody molecules of this invention, or fragments of the antibody molecules, which may or may not be chemically modified, in the field of medicine.

5.6.1. IMMUNIZATION AGAINST TUMORS

Patients having tumors may be treated therapeutically by immunization with the anti-idiotype monoclonal antibodies of the present invention whereas patients with a disposition for the tumor may be treated immunoprophylactically by such immunization. An advantage of using anti-idiotypic mAb over antigen in a tumor vaccine formulation is that large quantities of identical material can be obtained for use as immunogen. This is especially valuable when the antigen is a glycolipid or a carbohydrate, which itself may be difficult to obtain in pure form and in sufficient amounts. In addition, if the antigen is a protein, the availability of an anti-idiotypic antibody avoids the necessity of having the cloned gene for the antigen, in order to obtain sufficient quantities of the antigen for use in vaccines. The anti-idiotypic antibodies, or fragments of the anti-idiotypic antibodies, or chemically modified fragments or antibodies may be used to immunize against tumors. Any mAb fragment containing the idiotype of the mAb molecule could be used, including but not limited to the $F_v$, Fab, Fab', or $F(ab')_2$ fragments, which can be generated by known techniques. The anti-idiotypic antibody molecule or its derivative fragments may be formulated with a suitable adjuvant in order to enhance the immunological response. These adjuvants may include, but are not limited to, mineral gels, e.g. aluminum hydroxide; surface active substances such as lysolecithin, pluronic polyols; polyanions; peptides; oil emulsions; and potentially useful human adjuvants such as BCG (bacille Calmette-Guerin) and corynebacterium parvum. The immunogen may also be incorporated into liposomes, or conjugated to polysaccharides and/or other polymers, or otherwise chemically modified for use.

Many methods may be used to introduce the immunizing formulations; these include but are not limited to intradermal, intramuscular, intraperitoneal, intravenous, subcutaneous, and intranasal routes.

In particular embodiments of the invention, hosts with fibrosarcoma can be injected intraperitoneally with an anti-idiotypic monoclonal antibody specific to an idiotope which recognizes a fibrosarcoma antigen.

Immunization in test animals may be assayed by injection of the anti-idiotypic antibody or related derivative molecule, followed by challenge with a tumorigenic agent(s) such as syngeneic tumor cells or chemical carcinogens, and observing tumor development and progression.

5.6.2. ADOPTIVE IMMUNOTHERAPY

In another embodiment of the invention, T cells (preferably $T_H$) which express an idiotope which recognizes a tumor antigen which can be, but is not limited to, an antigen described in Section 5.3.1, supra, can be introduced into a host, for immunoprophylaxis or immunotherapy. Such cells can be obtained from the tumor-growing host himself, expanded in vitro, selected for the proper idiotypic specificity (either before or after expansion), and reintroduced into the host (see Section 8.4, infra). Alternatively, the T cells can be obtained from an appropriate (preferably histocompatible) donor.

In an alternative approach, it is possible to activate tumor-specific lymphocytes in vitro and to treat the patient with the activated tumor-specific leukocytes. Recently, regression of cancer was observed in response to an adoptive immunotherapeutic treatment involving the administration of lymphokine activated killer cells (LAK) to tumor-bearing hosts and Rosenberg et al., 1985, New Engl. J. Medicine 313:1485–1492). However, this therapy resulted in a number of undesirable side effects, including severe toxicity, pulmonary edema, and respiratory distress. By contrast, the method of this embodiment of the present invention involves administering to a patient stimulated lymphocytes which are specific for the tumor associated antigen (which can be, but is not limited to, an antigen described in Section 5.3.1, supra) which may result in a more specific therapy and reduced side effects. This can be accomplished, for example, by a modification of the methods described in copending application Ser. No. 909,447, filed Sep. 19, 1986, by Hu and Zarling, entitled "Methods of Adoptive Immunotherapy for Treatment of AIDS," which is incorporated by reference herein. Peripheral lymphocytes can be withdrawn from the patient, or a histocompatible donor who was exposed either to the tumor antigen or to a monoclonal anti-idiotypic antibody raised to the idiotype of an antibody that defines the tumor antigen as described above. The lymphocytes can then be stimulated in vitro in the presence of the tumor-specific anti-idiotypic antibodies of the present invention. Such specific stimulation can be accomplished using the monoclonal anti-idiotypic antibodies of the present invention in a method such as the one described by Binz et al. (1982, Int. J. Cancer 29:417–423), or described in copending application Ser. No. 909,447, filed Sep. 19, 1986. The activated T cells can then be expanded in cell culture. This expansion can be accomplished by repeated stimulation of the T cells with the anti-idiotypic antibodies of the invention, with or without IL-2, or by growth in medium containing IL-2 alone. Other methods of T cell cultivation (for example, with other lymphokines, growth factors, or other bioactive molecules) can also be used. The activated lymphocytes may then be tested for cell-mediated antitumor immune reactivity. If desired, confirmation of identity of the activated lymphocytes as T cells can be accomplished by examination of the cells with regard to cell-surface expression of T and B cell markers. This can be carried out, for example, by immunofluorescence analysis using fluorescein-conjugated monoclonal antibodies to T and B cell antigens. Expression of known T cell markers, such as the CD4 and CD8 antigens, confirms the identity of the activated lymphocytes as T cells.

The activated T cells are then tested for antitumor reactivity. This can be accomplished by any of several techniques known in the art for assaying specific cell-mediated immunity. For example, a cytotoxicity assay, which measures the ability of the stimulated T cells to kill the tumor cells in vitro, may be accomplished by incubating the lymphocytes with $^{51}$Cr-labelled tumor cells, and uninfected labelled cells, and measuring $^{51}$Cr release upon lysis. Such assays have been described (see, for example, Zarling, J. M., et al., 1986, J. Immunol. 136:4669). The activated lymphocytes can also be tested for T helper cell activity by measuring their ability to proliferate, as shown by $^3$H-thymidine incorporation, following stimulation, and/or by measuring their ability to produce lymphokines such as IL-2 or interferon upon stimulation, in the absence of exogenous IL-2 (see copending application Ser. No. 909,447, filed Sep. 19, 1986). Other assays of specific cell-mediated immunity known in the art, such as leukocyte-adherence inhibition assays (Thomson, D.M.P. (ed.), 1982, Assessment of Immune Status by the Leukocyte Adherence Inhibition Test, Academic Press, New York), may also be used. The selected lymphocytes can then be inoculated into the patient. Inoculation of the activated T cells is preferably through systemic administration although other methods of administration (for example, direct infusion into an artery) can be used. The T cells can be administered intravenously through a central venous catheter or into a large peripheral vein. In a preferred embodiment, approximately $1\times10^8$ cells are infused initially and the remainder are infused over the following several hours. In some patients, recombinant human IL-2 may be used and can be infused intravenously every 8 hours beginning at the time of T cell infusion. Injections of IL-2 will preferably be at doses of 10,000 to 100,000 units/kg bodyweight, as previously used in cancer patients (Rosenberg, S. A., et al., 1985, N. Engl. J. Med. 313:1485). The IL-2 infusion can be continued for several days after infusion of the activated T cells if tolerated by the patient.

5.6.3. INHIBITION OF IMMUNE SUPPRESSION OF ANTI-TUMOR REACTIVITY

In another embodiment of the invention, anti-idiotypic antibodies which specifically recognize an idiotope which is directed against a tumor antigen and which idiotope is present on suppressor T cells and/or suppressor factors, can be administered in vivo in order to inhibit suppression of anti-tumor reactivity. In particular embodiments, such a tumor antigen can include but is not limited to those listed in Section 5.3.1, supra.

5.6.4. IMMUNOAFFINITY APPLICATIONS

The anti-idiotypic antibodies or related molecules of this invention may be used to isolate antibodies directed against a defined tumor antigen. Techniques known in the art by which this could be accomplished include but are not limited to immunoaffinity columns and immunoabsorption reactions. Anti-tumor antibody isolated through use of the anti-idiotypic antibody or related molecules could be a valuable tool in tumor immunotherapy.

5.6.5. IMMUNOASSAYS

In an alternate embodiment of the present invention, the anti-idiotypic antibodies or related molecules of the present invention may be used as antigens in immunoassays. These immunoassays would allow the detection of anti-tumor antibody in animals or patients. The molecules of the present invention would also be used in competition immunoassays to test for the presence of tumor antigens.

The molecules of the present invention may be used in any immunoassay system known in the art, including but not limited to radioimmunoassays, ELISA assays, "sandwich" assays, precipitin reactions, gel diffusion precipitin reactions, immunodiffusion assays, agglutination assays, complement-fixation assays, protein A immunoassays, fluorescent immunoassays, and immunoradiometric assays.

In a specific embodiment, the anti-idiotypic antibodies of the invention, directed against an idiotype of "Antibody 1" which defines a tumor antigen, can be used in competitive immunoassays to monitor the presence of antibodies in patients being administered Antibody 1, for therapeutic or diagnostic purposes (see Sections 9.1.1.5, 9.2.5., infra). In another embodiment, anti-idiotypic antibodies can be used to identify anti-tumor antibodies during purification procedures.

6. ANTI-IDIOTYPIC ANTIBODY SPECIFIC TO AN IDIOTYPE WHICH RECOGNIZES A BLADDER CARCINOMA ANTIGEN

In the examples described herein, a murine model is used to demonstrate that an immune response to self-differentiation antigens can be induced in vivo in accordance with the invention. In particular, the examples demonstrate that anti-idiotypic antibodies raised against the idiotype of an antibody that defines an oncofetal antigen are capable of inducing an immune response against the tumor-specific antigen present in a syngeneic host in vivo. Delayed-type hypersensitivity in vivo and leukocyte adherence inhibition assays in vitro provide evidence for the induction of tumor-specific cell-mediated immunity in the antibody injected mice. The experiments detailed in section 6 have been described in Lee, V. K., et al., 1985, Proc. Natl. Acad. Sci. U.S.A. 82:6286–6290, incorporated by reference herein. A detailed description of each step in this embodiment of the invention is presented in the subsections below.

6.1. GENERAL PROCEDURES

6.1.1. ANIMALS

Brother-sister-mated BALB/c mice from the Fred Hutchinson Cancer Research Center colony were used for the induction and serial propagation of bladder carcinomas for the immunization that led to the development of anti-idiotypic antibodies 21D9 and A43A10, and for DTH assays.

A second source of mice, employed for the LAI tests, were from the Central Animal Breeding House (University of Queensland). These mice were also propagated by brother-sister mating, which allowed the progressive growth of bladder carcinoma, BTCC-1660, and a sarcoma, MCA-1511, without signs of rejection.

Nude (nu/nu) mice from Charles River Breeding Laboratories were used for the propagation of rat hybridomas as ascites tumors.

6.1.2. TUMORS

BTCC-1660 (Hellstrom, I., et al., 1985, Cancer Res. 45:2210–2218) is a bladder transitional cell carcinoma (BTCC) induced by MCA as described (Chapman, W. H., 1962, J. Urol. 88:518–526). It was serially propagated in syngeneic mice and regularly examined by histology to verify that the tumor line retained the characteristics of BTCC. BTCC-1660 was propagated in BALB/c mice from the Fred Hutchinson Cancer Research Center for 10 transfers prior to the DTH testing and for an additional 2 or 3 transfers in University of Queensland BALB/c mice prior to the LAI assays.

A MCA-induced, transplanted BALB/c sarcoma, MCA-1511, was employed as specificity control in the DTH and LAI assays.

6.2. ANTIBODIES

6.2.1. ANTIBODY 6.10

Antibody 6.10 is a rat monoclonal IgG2a antibody which recognizes a 175-kDa oncofetal antigen specifically expressed in all BALB/c mouse BTCC, in epithelial cells of the mouse embryo, and in a few epithelial cells of adult mice (Hellstrom, I., et al., 1985, Cancer Res. 45:2210–2218); thus, the tumor specificity of the antigen recognized by antibody 6.10 was similar to that of other tumor associated differentiation antigens, for example, the various antigens of human lung carcinomas (see Hellstrom et al., 1986, Cancer Res. 46:3917–3923). The antibody was purified by ammonium sulfate precipitation followed by DEAE chromatography for use in the described embodiment of the invention.

6.2.2. ANTI-IDIOTYPIC ANTIBODIES

Monoclonal anti-idiotypic antibodies (Ab2) were obtained by injecting BALB/c mice subcutaneously with 100 ug of purified antibody 6.10 (Ab1) in complete Freund's adjuvant followed by intraperitoneal injection of the same amount in incomplete Freund's adjuvant 5 days later. Mice were then injected with antibody 6.10 in saline for an additional two or three times at 5-day intervals. Spleen cells from the mice were harvested 3 days after the last injection and were hybridized with NS-1 myeloma cells. Hybridomas 21D9 and 43A10 were derived from two different fusions. Antibodies made by the hybridomas were initially screened for binding specifically to antibody 6.10 and not to purified normal rat serum IgG by using an ELISA (Nepom, G. T., et al., 1984, Proc. Natl. Acad. Sci. U.S.A. 81:2864–2867; Holbeck, S. L. and Nepom, G. T., 1983, J. Immunol. Methods 60:47–52). The hybridomas were cloned. They were propagated in pristane-primed BALB/c mice as ascites tumors. Antibodies 21D9 and 43A10 were found to be IgM by immunodiffusion.

We tested, as previously described (Nepom, G. T., et al., 1984, Proc. Natl. Acad. Sci. U.S.A. 81:2864–2867), to what extent antibody 6.10, compared to various rat monoclonal antibodies used as controls and also established by hybridization with NS-1 cells, could competitively inhibit the binding of antibodies 21D9 and 43A10 to antibody 6.10 on solid phase in an ELISA. The same assay was also performed with Nonidet P-40 extracts (Nepom, G. T., et al., 1984, Proc. Natl. Acad. Sci. U.S.A. 81:2864–2867) from cultured cells of BTCC-1660 and sarcoma MCA-1511 (as a control) as inhibitors to establish whether the binding of antibodies 21D9 and 43A10 to antibody 6.10 could be competitively inhibited by bladder tumor antigen-containing extracts.

A syngeneic, monoclonal, anti-idiotypic antibody, 5.96, was used as a control, since it can induce specific DTH to sarcoma MCA-1511 in BALB/c mice when tested as described for another anti-idiotypic antibody-tumor combination (Forstrom, J. W., et al., 1983, Nature (London) 303:627–629). It was induced by hybridizing spleen cells from MCA-1511 immune BALB/c mice with NS-1 cells.

6.3. ASSAYS OF CELL-MEDIATED IMMUNITY

The induction of bladder tumor-specific cell-mediated immunity (CMI) was demonstrated in vivo by using an assay for DTH, and in vitro by measuring LAI.

6.3.1. ASSAY FOR DTH IN VIVO

The DTH was induced and measured in the same manner as described for an anti-idiotypic antibody related to a chemically induced BALB/c sarcoma, MCA-1490 (Forstrom, J. W., et al., 1983, Nature (London) 303:627–629); the reactivity detected in the MCA-1490 system was found to be mediated by Thy-1$^+$, Lyt-1$^+$ cells and to have the histological characteristics of a DTH reaction (Forstrom, J. W., et al., 1983, Nature (London) 303:627–629). The mice (five per group) were each primed at various subcutaneous sites with 5–10 ug of an antibody, and 5 days later $5 \times 10^5$ tumor cells were injected into one of their hind footpads. The footpads were measured 24 hours after injection of the tumor cells with an engineer's micrometer. The increase in swelling was calculated by comparison with the contralateral footpad that was not injected. All of the mice were individually earmarked and all measurements were done in a "blind" fashion.

6.3.2. ASSAY FOR LAI IN VITRO

The LAI technique (Halliday, W. J., and Maluish, A. E., 1982, in *Assessment of Immune Status by the Leukocyte Adherence Inhibition Test*, Academic, New York, pp. 1–26; and Koppi, T. A., and Halliday, W. J. 1982, Cell Immunol. 66:394–406) was employed as an in vitro correlate of the DTH assay. This test measures immunoreactivity of Thy-1$^+$, Lyt-1$^+$, L3T4$^+$ lymphocytes which are stimulated by specific antigen to produce a lymphokine that decreases leukocyte adherence to glass.

As a primary source of effector cells, peritoneal cells (PC) were used from mice bearing transplanted tumors that were 5–10 mm in diameter. Mice injected one to three times with antibody 21D9, 43A10, or 5.96 (5 ug per injection) were also used to provide PC 5–10 days after the last injection. LAI reactivity was determined in hemocytometer chambers as described using mixtures of PC and antigens in the form of tumor extracts or anti-idiotypic antibodies at an optimal concentration as determined by prior titration. The extracts were prepared (Koppi, T. A. and Halliday, W. J., 1981, J. Natl. Cancer Inst. 66:1089–1096) by homogenizing tumor tissue (1 vol) in phosphate-buffered saline at pH 7.2 (4 vol) and centrifuging the homogenate. The supernatants were stored in small volumes at −50° C. All determinations of percentage adherence of PC were done in a blind fashion on coded mixtures. The significance of differences between treatments was assessed by Student's t test, using means of 18–20 replicate determinations.

6.4. IMMUNOABSORPTION

Antibody 6.10 (1.5 mg) was coupled to 1.5 ml of swollen CNBr-Sepharose 4B gel (Pharmacia) as described by the manufacturers. Normal rat serum globulin on Sepharose gel was used as a control. For absorption of tumor extract, 1.0 ml of undiluted extract was mixed with 1.0 ml of coupled gel for 30 minutes at room temperature. The mixture was centrifuged briefly and the supernatant was reabsorbed with another 0.5 ml portion of gel. The gel portions were pooled, washed, and eluted with glycine buffer at pH 2.8 (three times with 0.5 ml). The pooled eluates were neutralized with sodium bicarbonate solution. Absorbed extracts and eluates were stored at −50° C. Before use in LAI assays, their concentrations were adjusted to allow for dilution during absorption.

6.5. TREATMENT OF PERITONEAL CELLS WITH ANTIBODIES AND COMPLEMENT

Peritoneal cells were pretreated with anti-idiotypic antibodies and complement, before reacting in LAI assays, to test whether these antibodies could specifically inactivate antigen-reactive cells by binding to their receptors (Binz, H. and Wigzell, H., 1975, J. Exp. Med. 142:197–211). The antibodies (40–120 ug) were incubated with PC ($1\times10^7$ cells in 0.5 ml of medium) for 30 minutes at 37° C. The cells were then washed and incubated with complement (1 ml of guinea pig serum diluted 1:6) for another 30 minutes at 37° C. After the final wash, the treated PC were used as before in the assay. The effect of pretreatment on overall cell viability was negligible.

Experiments were also performed in which PC were pretreated with monoclonal antibodies to Thy-1.2 or L3T4 and guinea pig complement as previously described (Koppi, T. A. and Halliday, W. J., 1982, Cell. Immunol. 66:394–406).

6.6. SPECIFIC INDUCTION OF CELL-MEDIATED IMMUNITY

The subsections below describe the results of the experiments conducted using the methods described above.

6.6.1. ANTI-IDIOTYPIC ANTIBODIES 21D9 AND 43A10 ARE SPECIFIC FOR IDIOTYPE(S) ON ANTIBODY 6.10

Antibody 6.10 was used to immunize mice to obtain monoclonal antibodies to idiotypic determinants on antibody 6.10. Two antibodies of desired specificity made by hybridomas 21D9 and 43A10 resulted from this approach. Table I shows that both antibodies bound to antibody 6.10 and that this binding was competitively inhibited by antibody 6.10 but not by other rat monoclonal antibodies with NS-1 parent of the same or different subclasses or by rat serum IgG.

TABLE I

BINDING OF ANTIBODIES 21D9 AND 43A10 TO ANTIBODY 6.10 IS COMPETITIVELY INHIBITED BY ANTIBODY 6.10

| Inhibitor | Binding of Antibody* | |
|---|---|---|
| | 21D9 | 43A10 |
| None | 0.33 | 0.28 |
| 6.10 | | |
| 2 ug | 0.19 | 0.12 |
| 20 ug | 0.07 | 0.04 |
| 53–6.72†(anti-Ly-2, IgG2a) | 0.33 | 0.26 |
| 30–C7†(anti-gp100, IgG2a) | 0.40 | 0.25 |
| 53–8.1†(anti-Thy-1, IgG2c) | 0.30 | 0.33 |

TABLE I-continued

BINDING OF ANTIBODIES 21D9 AND 43A10 TO ANTIBODY 6.10 IS COMPETITIVELY INHIBITED BY ANTIBODY 6.10

| Inhibitor | Binding of Antibody* | |
|---|---|---|
| | 21D9 | 43A10 |
| 53–3.1†(anti-Thy-1, IgM) | 0.28 | 0.27 |
| Rat IgG††(total serum IgG) | 0.30 | 0.29 |

*$OD_{492}$ reading in ELISA with an automated spectrophotometer.
†Rat monoclonal antibodies (20 ug each) that define various mouse lymphocyte differentiation antigens.
††20 ug.

The binding of antibody 21D9 or 43A10 to antibody 6.10 was also inhibited by lysates of BTCC-1660 but not by a control lysate of sarcoma MCA-1511 (FIG. 4).

6.6.2. ANTIBODY 43A10 INDUCES CMI TO BTCC-1660 AS DETECTED BY DTH REACTIONS IN VIVO

We investigated whether antibody 43A10 could induce an active immune response in the form of DTH to BTCC-1660 cells. This was done in a "crisscross" pattern by testing two different antibodies, 43A10 and 5.96 (both with the NS-1 myeloma cell parent), and two tumors with different antigen specificity, BTCC-1600 and sarcoma MCA-1511. As shown in Table II, immunization of mice with antibody 43A10 produced DTH to BTCC-1660 but not to MCA-1511, whereas immunization with antibody 5.96 gave DTH to MCA-1511 but not to BTCC-1660. This result indicates that the DTH reactions were immunologically specific.

TABLE II

ANTIBODY 43A10 INDUCES DTH IN BALB/C MICE

| Group | Immunization | Challenge | % increase (of footpad) |
|---|---|---|---|
| Bladder Carcinoma | None | BTCC-1660 | 20.22(control) |
| | BTCC-1660 | BTCC-1660 | 45.4* |
| | 5.96 | BTCC-1660 | 24.2 |
| | 43A10 | BTCC-1660 | 41.8* |
| MCA Sarcoma | None | MCA-1511 | 5.8 (control) |
| | 5.96 | MCA-1511 | 16.4* |
| | 43A10 | MCA-1511 | 5.6 |

*Differences statistically significant from respective untreated controls (P less than 0.05.)

6.6.3. ANTIBODIES 21D9 AND 43A10 INDUCE CMI TO BTCC-1660 AS DETECTED BY LAI REACTIONS IN VITRO

To confirm the ability of antibodies 21D9 and 43A10 to induce immunoreactivity to BTCC-1600 and as a first step toward investigating this response further, we tested whether PC from mice injected with either antibody were reactive in vitro as detected by the LAI technique. An extract of BTCC-1660 was used as test antigen together with an extract of sarcoma MCA-1511, which was employed as a control. As shown in Table III, PC from BTCC-1660 tumor-bearing mice recognized the corresponding antigen extract selectively, and this activity was also found with PC from antibody 21D9-sensitized mice. A crisscross specificity control was provided by PC from antibody 5.96-sensitized animals, which were not affected by BTCC-1660 but exhibited LAI with the MCA-1511 extract. Mice sensitized with antibody 43A10 had PC that recognized antigen(s) in the BTCC-1660 extract (Table III). The same PC reacted in vitro with 43A10.

TABLE III

SPECIFICITY OF LAI REACTIONS IN MICE BEARING BLADDER CARCINOMAS OR INJECTED WITH ANTI-IDIOTYPIC ANTIBODIES

| PC Donor | Antigen in Assay[a] | % Adherence |
| --- | --- | --- |
| 1660 Tumor-Bearer | — | 86.2 ± 2.6 |
| | 1660 extract | 59.8 ± 3.4[b] |
| | 1511 extract | 85.4 ± 2.7 |
| 21D9-sensitized | — | 78.2 ± 2.7 |
| | 1660 extract | 60.5 ± 3.2[b] |
| | 1511 extract | 72.8 ± 3.9 |
| 5.96-sensitized | — | 80.6 ± 2.9 |
| | 1660 extract | 82.8 ± 3.4 |
| | 1511 extract | 59.7 ± 2.5[b] |
| 43A10-sensitized | — | 78.6 ± 4.4 |
| | 1660 extract | 63.6 ± 5.5 |
| | 43A10 | 56.6 ± 4.2[b] |

Data are presented as mean ± SEM.
[a]Antigen used at concentration determined as optimal with reactive PC (1:32 and 1:8 dilutions for extracts BTCC-1660 and MCA-1511, respectively; 0.1 ug/ml for 43A10).
[b]Significant LAI compared to control without antigen (P less than 0.01).

T lymphocytes were required for the LAI reactivity. When PC from antibody 21D9-sensitized mice were incubated with complement but no antigen, the adherence was 67.1%. This adherence decreased to 55.6% when BTCC-1660 extract was also added. When anti-Thy-1.2 antibody was added to the mixture of PC, BTCC-1660 extract, and complement, the adherence increased to 66.6% (it was 62.5% in the absence of the BTCC-1660 extract)--that is, LAI reactivity was abolished. Pretreatment with antibody to L3T4 and complement, likewise, abrogated lymphocyte reactivity to BTCC-1660.

Thus two separate techniques, DTH in vivo and LAI in vitro provided evidence for tumor-specific CMI in mice injected with anti-idiotypic antibody. The antibodies to lymphocyte surface markers identified the LAI-reactive cells from antibody 21D9-sensitized mice as belonging to the helper T-cell subset (Thy-1$^+$, L3T4$^+$), confirming previous results (Koppi, T. A. and Halliday, W. J., 1982, Cell. Immunol. 66:394–406).

6.6.4. THE ANTIGEN RECOGNIZED BY ANTIBODY 21D9-INDUCED PC IS ABSORBED FROM TUMOR EXTRACT BY ANTIBODY 6.10

When BTCC-1660 tumor extract was doubly absorbed with antibody 6.10 coupled to Sepharose gel, the residual absorbed extract no longer reacted in LAI with antibody 21D9-sensitized PC (Table IV). However, it still reacted with BTCC-1660 tumor-bearer PC, indicating the existence of cells sensitized to antigen(s) in the tumor extract other than the one defined by antibody 6.10. Also shown in Table IV are the results of testing the acid eluate from the above gel. This reacted with both types of PC and presumably contained the 6.10-related antigen in a purified form.

TABLE IV

REACTIVITY OF FRACTIONS OF BTCC-1660 EXTRACT IN LAI AFTER ABSORPTION WITH ANTITUMOR ANTIBODY 6.10 ON SEPHAROSE GEL

| | % Adherence of PC | | |
| --- | --- | --- | --- |
| Fraction in Assay[a] | 21D9-Sensitized Mice | 1660 Tumor-Bearing Mice | Normal Mice |
| — | 76.7 ± 4.3 | 72.8 ± 3.2 | 71.3 ± 3.9 |
| Residue after absorption with 6.10 gel | 71.9 ± 4.2 | 49.2 ± 4.8[b] | 75.9 ± 4.0 |
| Acid eluate from 6.10 gel | 59.6 ± 3.5[b] | 45.0 ± 3.6[b] | 74.6 ± 3.9 |
| Residue after absorption with control gel[c] | 61.1 ± 3.0[b] | 58.1 ± 3.3[b] | 84.0 ± 3.4 |
| Acid Eluate from control | 84.9 ± 3.2 | 72.8 ± 3.4 | 79.6 ± 3.3 |

Data are presented as mean ± SEM.
[a]Each fraction used as antigen in mixtures with PC from three groups of mice. The antigen extract was the same as that used in Table 3.
[b]Significant LAI compared to control without antigen (P less than 0.01).
[c]Control gel was coupled with normal rat serum globulin.

The ability of cells from antibody 21D9- or 43A10-sensitized mice to react with BTCC-1660 tumor extract in vitro suggested that the relevant tumor antigen was present in that extract. This was confirmed by immunoabsorption of antigenic activity from the extract by antitumor antibody 6.10 and its subsequent elution. The BALB/c mouse thus exhibits the ability to recognize and respond to an 175-kDa antigen shared by syngeneic bladder carcinomas, embryonic tissues, and a few adult cells of the host, after sensitization with antibodies 21D9 and 43A10.

The 175-kDa molecule was not the only antigen recognized by BTCC-1660 tumor-bearing mice and present in BTCC-1660 extract, since other antigens reactive with appropriate PC remained after absorption with antibody 6.10 (Table IV). Antigens remaining in the absorbed extract might include the individually specific antigens commonly associated with chemically induced murine tumors (Hellstrom, K. E. and Hellstrom, L. 1969, Adv. Cancer Res. 12:167–223).

6.6.5. USE OF ANTIBODY 21D9 AS A SPECIFIC INHIBITORY ANTIBODY FOR IDIOTYPE-POSITIVE CELLS

To further test the specificity of the LAI reactivity induced by injecting mice with antibody 21D9, we examined whether this reactivity was lost after in vitro incubation of PC from the injected mice with antibody 21D9 and complement. This was done in an attempt to remove the reactive cells that were expected to be idiotype-positive (Binz, H. and Wigzell, H., 1975, J. Exp. Med. 142:197–211); incubation with antibody 5.96 was used as a control. As shown in Table V, reactivity to BTCC-1660 was abrogated by pretreatment with antibody 21D9, whereas antibody 5.96 had no effect. The reverse was found when PC from antibody 5.96-sensitized mice were pretreated with the same antibodies and tested against the MCA-1511 extract.

TABLE V

SPECIFIC INACTIVATION OF TUMOR ANTIGEN-REACTIVE
CELLS BY PRETREATMENT WITH ANTI-IDIOTYPIC ANTIBODIES[a]

| Antibody | | | |
|---|---|---|---|
| To Sensitize Mice | To Pretreat PC | Antigen in Assay | % Adherence |
| 21D9 | 21D9 | — | 71.5 ± 3.5 |
| 21D9 | 21D9 | 1660 extract | 79.0 ± 4.5 |
| 21D9 | 5.96 | — | 81.7 ± 3.2 |
| 21D9 | 5.96 | 1660 extract | 54.2 ± 4.1* |
| 5.96 | 21D9 | — | 78.9 ± 3.0 |
| 5.96 | 21D9 | 1511 extract | 43.9 ± 2.2* |
| 5.96 | 5.96 | — | 71.7 ± 3.4 |
| 5.96 | 5.96 | 1511 extract | 64.9 ± 3.0 |

[a]BALB/c mice were sensitized by injection of antibody, their PC were pretreated with antibody and complement, and then these cells were tested in LAI assays with tumor extract as antigen. Data are presented as mean ± SEM.
*Significant LAI compared to control without antigen (P less than 0.001).

In these studies, we have undertaken a thorough investigation of the observed phenomena. Anti-idiotypic antibodies 21D9 and 43A10 induced specific CMI in mice. The sensitized T cells recognized the tumor antigen in crude extracts and in partially purified eluates (in LAI) and in whole bladder tumor cells (in DTH). They recognized these antigens through receptors with specificity for a single idiotype since they could be specifically inhibited by the appropriate anti-idiotypic antibody (Table V).

7. TUMOR-SPECIFIC IDIOTOPES ON SUPPRESSOR FACTORS AND SUPPRESSOR CELLS REVEALED BY MONOCLONAL ANTI-IDIOTYPIC ANTIBODIES

In the examples sections infra, two monoclonal anti-idiotypic antibodies, previously found to induce tumor-specific cell-mediated immunity in mice, were examined for their relationship to tumor-associated suppressor factors (SF), produced in culture by spleen cells from tumor-bearing mice or present in sera from such mice. A leukocyte adherence inhibition assay was used to detect cellular immunoreactivity to tumor antigens and its inhibition by SF, using peritoneal cells from mice bearing tumor or sensitized with anti-idiotypic antibody. The SF were specifically absorbed by the corresponding anti-idiotypic antibodies coupled to a solid phase, and were recovered by elution. They were also specifically neutralized by the addition of the respective antibodies to the assay system. Anti-idiotypic antibody, used with complement to pretreat spleen cells from tumor-bearing mice, prevented these cells from producing SF in culture. Tumor antigen-reactive effector cells, suppressor cells, and SF thus share similar idiotopes, permitting their respective functions to be modulated by appropriate anti-idiotopes.

7.1. MATERIALS AND METHODS

7.1.1. MICE

Brother-sister mated BALB/c mice from the Central animal Breeding House, University of Queensland, were used or tumor propagation and immunization.

7.1.2. TUMORS AND EXTRACTS

BTCC-1660 and fibrosarcoma 1511 were induced by 3-ethylcholanthrene in BALB/c mice from the Fred Hutchinson Cancer Research Center, Seattle, Wash., and propagated in syngeneic mice at Oncogen, Seattle, Wash., for 5 to 10 passages before the present experiments. The tumors were free from detectable contamination with mycoplasma and lactic dehydrogenase virus. Mice bearing tumors were transported to the University of Queensland, Brisbane, Australia, where the tumors were successfully transplanted to the locally available animals. Crude antigen extracts were prepared by homogenization of tumor tissue in phosphate-buffered saline and were standardized and tested for specific antigenic activity as previously described (Koppi, T. A. and Halliday, W. J., 1981, J. Natl. Cancer Inst. 66:1089).

7.1.3. SERA

Normal BALB/c mouse serum and serum from tumor-bearing mice (usually 10–20 days after transplantation) were obtained by tail bleeding and stored at −20° C.

7.1.4. ANTIBODIES

Monoclonal anti-idiotypic antibody (MAIA) 21D9 has been described supra (see Section 6). It was raised against a rat monoclonal anti-tumor antibody (mAb 6.10) which recognizes an oncofetal antigen expressed by all primary and transplanted BTCC tested (even when induced by different chemical carcinogens) and by several tissues of mouse embryos but not appreciably by adult mouse tissues. MAIA 5.96 is specific for an antigen of sarcoma 1511. It was derived by hybridizing spleen cells from a BALB/c mouse hyperimmunized against sarcoma 1511. Monoclonal anti-Lyt-2.2 antibody was provided by Professor I. F. C. McKenzie.

7.1.5. SENSITIZATION WITH MONOCLONAL ANTI-IDIOTYPIC ANTIBODIES

Mice were injected subcutaneously one to three times with 5 ug doses of MAIA 21D9 and 5.96 in aqueous solution.

7.1.6. PERITONEAL CELLS

Peritoneal cells (PC) were obtained from peritoneal washings of MAIA-injected mice (4–10 days after the last injection) or tumor-bearing mice (10–20 days after transplantation). Cells were collected in Hanks' solution (Commonwealth Serum Laboratories, Parkville, Australia) containing 5 I.U. heparin/ml. Cells from four to six mice were pooled, washed with Eagle's basal medium (Commonwealth Serum Laboratories) containing 10% fetal calf serum (FCS), and adjusted to $1\times10^7$/ml.

7.1.7. SPLEEN CELL CULTURES

Spleen cell (SC) cultures were prepared as previously described (Nelson, K., et al., 1975, Int. J. Cancer 16:539; Koppi, T. A. and Halliday, W. J., 1983, Cell. Immunol. 76:29). Spleens from normal and tumor-bearing mice (10–20 days after transplantation) were removed and passed through stainless steel mesh. Erythrocytes were lysed with ammonium chloride and the remaining cells were washed twice with medium. The SC were then cultured for 48 hours. The cultures were centrifuged and the supernatants were collected and stored at −50° C. until required. In some experiments, SC were treated before culture with the antibodies mentioned above (Koppi, T. A. and Halliday, W. J., 1983, Cell. Immunol. 76:29). MAIA 21D9 and 5.96 were used at 160–200 ug/ml and anti-Lyt-2.2 at 1:100 dilution; controls contained no antibody. SC suspensions were centrifuged and the cell pellets resuspended in the antibody solutions ($3\times10^7$ cells in 1.5 ml) at 37° C. for 30 minutes with occasional shaking. Each mixture was then centrifuged and the cells were washed in cold medium. The supernatants were discarded and 2.0 ml of guinea pig complement (diluted 1:5 in medium) was added to each cell pellet. The cells were resuspended and incubated for a further 30 minutes at 37° C., after which they ere washed and suspended in medium ($10^7$ cells/ml).

7.1.8. IMMUNOABSORPTION

MAIA 21D9 or 5.96 (1.8–2.0 mg) were coupled to 2 ml of swollen CNBr-Sepharose 4B gel (Pharmacia Fine Chemicals, Uppsala, Sweden) as described supra in Section 6.4. For absorption of SF from tumor-bearer sera or SC supernatants, these were mixed with equal volumes (0.5 ml) of coupled gels. The mixtures were incubated at room temperature for 1 hour on a rotary mixer, centrifuged briefly, and supernatants retained. The gels were later washed and eluted with glycine-HCl buffer, pH 2.8 (three times with 0.5 ml). The pooled eluates were neutralized to pH 7, concentrated to 0.5 ml, and stored at –20° C.

7.1.9. NEUTRALIZATION OF SUPPRESSOR FACTORS

MAIA 21D9 and MAIA 5.96 were used to neutralize or "unblock" (Hellstrom, I. and Hellstrom, K. E., 1970, Int. J. Cancer 5:195) the activity of SF present in tumor-bearer serum or in SC supernatants. Each MAIA (25–30 ug) was mixed with 0.1 ml of serum or supernatant and left for about 5 minutes at room temperature. These mixtures were examined for suppressive activity by addition to reactive LAI assays as described infra.

7.1.10. LAI TECHNIQUE

THe direct LAI assay involves the determination of glass adherence of sensitized PC and the inhibition of this adherence by a relevant antigen; SF are detected by their ability to block LAI when added to a reactive cell-antigen mixture. For the detection of LAI, the mixtures contained sensitized PC ($10^6$ cells) in 0.1 ml of medium, 0.05 ml of relevant antigen at optimal concentration (or control with medium only), and 0.05 ml of normal mouse serum. For the detection of SF in test sera, these were included in mixtures in place of normal serum. For the detection of SF in culture supernatants, these were used in 0.1 ml amounts to suspend the PC, in place of medium. Thus the serum concentration was always constant. The mixtures were preincubated at 37° C. for 30 minutes and then introduced into hemocytometers (four chambers for each different mixture). After a further incubation at 37° C. for 60 minutes, the total number of cells in each of 20 squares (a pattern of 5 in each chamber) was counted for each mixture. The nonadherent cells were washed away and the remaining adherent cells were recounted in the same squares. All mixtures were coded before counting. The percentage leukocyte adherence was calculated for each mixture (20 values/mixture), and the mean percentage adherence and standard error (SE) were determined. A reduction in adherence, consequent upon the addition of antigen to PC in a mixture with normal serum, was interpreted as LAI. If substitution of a test serum or culture supernatant restored the adherence, this was interpreted as suppression of LAI. The statistical significance of these differences was determined by Student's t test. The entire procedure has been published (Halliday, W. J., et al., 1974, Cell. Immunol. 10:467; Halliday, W. J., et al., 1980, J. Natl. Cancer Inst. 65:327; Koppi, T. A. and Halliday, W. J., 1981, J. Natl. Cancer Inst. 66:1089; Koppi, T. A. and Halliday, W. J., 1982, Cell. Immunol. 66:394; Maluish, A. E. and Halliday, W. J., 1975, Cell. Immunol. 17:131).

7.2. SUPPRESSOR FACTORS IN THE SERUM OF TUMOR-BEARING MICE SUPPRESS LAI REACTIVITY IN A TUMOR-SPECIFIC FASHION

We first performed pilot tests to investigate whether sera from mice carrying the chemically induced sarcoma 1511 or the antigenically unrelated bladder carcinoma 1660 suppressed tumor-specific LAI reactivity. The results are shown in Table VI.

TABLE VI

SUPPRESSION OF LAI REACTION BY CORRESPONDING SF

| PC Donor | Antigen | Source of SF | % Adherence (mean ± SE) |
|---|---|---|---|
| 1511 tumor bearer | — | Normal serum | 72.1 ± 3.1 |
|  | 1511 extract | Normal serum | 48.7 ± 2.9* |
|  | 1511 extract | 1511 serum | 77.6 ± 4.4 |
| 1660 tumor-bearer | — | Medium only | 80.6 ± 2.8 |
|  | 1660 extract | Medium only | 69.9 ± 3.3* |
|  | 1660 extract | 1660 SC sup. | 82.3 ± 3.2 |
| 21D9 sensitized | — | Medium only | 89.2 ± 1.9 |
|  | 1660 extract | Medium only | 69.1 ± 2.0* |
|  | 1660 extract | 1660 SC sup. | 88.3 ± 3.6 | a Significant LAI compared with control containing the same PC and no antigen; P less than 0.01.
sup.: supernatant The upper part of Table VI shows the results for sarcoma 1511. The normal adherence of PC from tumor-bearing mice was reduced by the addition of 1511 extract, and it was restored to approximately the initial level when serum from 1511-bearing animals was included in place of control serum. We concluded that PC from mice with sarcoma 1511 were immune to antigen(s) expressed by this tumor and that serum from mice bearing the 1511 tumor suppressed the in vitro manifestation of this immunity. Similar experiments were then performed with BTCC-1660, testing sera taken 6–24 days after transplantation of this tumor. Only two of several serum samples harvested 10–12 days after tumor transplantation suppressed the LAI reactivity of immune PC, and serum samples taken at other time points did not suppress at all. We therefore tested supernatants of SC cultures from mice carrying BTCC-1660. The results were then uniformly positive. This is illustrated in the lower part of Table VI. Supernatant of SC from 1660-bearing mice suppressed the LAI reactivity of PC from such mice as well as from mice sensitized with the corresponding anti-idiotypic antibody, MAIA 21D9.

Table VII presents data from experiments testing the specificity of SF related to the antigenically distinct sarcoma 1511 and BTCC-1660.

TABLE VII

SPECIFICITY OF SF FROM TUMOR-BEARING MICE

| PC Donor | Antigen | Source of SF | % Adherence (mean ± SE) |
|---|---|---|---|
| 1511 tumor bearer | — | Normal serum | 78.9 ± 3.4 |
|  | 1511 extract | Normal serum | 55.8 ± 3.5* |

TABLE VII-continued

SPECIFICITY OF SF FROM TUMOR-BEARING MICE

| PC Donor | Antigen | Source of SF | % Adherence (mean ± SE) |
|---|---|---|---|
| | 1511 extract | 1511 serum | 80.6 ± 3.2 |
| | 1511 extract | 1660 SC sup. | 49.4 ± 2.8* |
| 1660 tumor-bearer | — | Medium only | 79.5 ± 1.7 |
| | 1660 extract | Medium only | 54.1 ± 3.4* |
| | 1660 extract | 1511 serum | 55.1 ± 3.4* |
| | 1660 extract | 1660 SC sup. | 75.2 ± 2.8 |

*Significant LAI compared with control containing the same PC and no antigen; P less than 0.01.
sup.: supernatant Serum from 1511 tumor-bearing mice mice suppressed LAI reactivity to 1511 but not to BTCC-1660, and SC supernatant from BTCC-1660 bearing mice suppressed LAI to BTCC-1660 but not to 1511. It seems justifiable to compare SF in serum and in culture supernatant, since they were tested under similar conditions (especially with respect to total serum concentration in the adherence mixtures—see Section 7.1.10, supra). As described infra, SC supernatants from mice carrying the 1511 tumor gave results similar to those obtained with the corresponding sera; that is, they suppressed the LAI reactivity only of PC from mice immune to sarcoma 1511.

7.3. MONOCLONAL ANTI-IDIOTYPIC ANTIBODIES SPECIFICALLY BIND TUMOR-SPECIFIC SUPPRESSOR FACTORS

We next investigated the ability of immunoabsorbents prepared with MAIA to specifically bind SF. The effector cells were PC from both tumor-bearing mice and mice sensitized with the appropriate MAIA. Antibodies 21D9 and 5.96, coupled to Sepharose, were used to absorb serum from 1511 tumor-bearing mice. Table VIII shows the effect of adding the original unabsorbed 1511 serum, absorbed serum, and eluates from the immunoabsorbents, respectively as sources of SF.

TABLE VIII

MAIA 5.96 CAN ABSORB SF FROM SERUM OF MICE BEARING SARCOMA 1511

| PC Donor | Antigen | Source of SF | % Adherence (mean ± SE) |
|---|---|---|---|
| 1511 tumor bearer | — | Normal | 75.6 ± 3.3 |
| | 1511 extract | Normal | 49.1 ± 3.0* |
| | 1511 extract | 1511 tumor bearer | 69.6 ± 3.9 |
| | 1511 extract | 1511 abs. 5.96 | 51.8 ± 3.2* |
| | 1511 extract | 1511 abs. 21D9 | 67.8 ± 3.3 |
| | 1511 extract | 5.96 eluate | 76.8 ± 4.2 |
| | 1511 extract | 21D9 eluate | 56.7 ± 2.7* |
| 5.96 sensitized | — | Normal | 68.3 ± 4.2 |
| | 1511 extract | Normal | 39.1 ± 2.5* |
| | 1511 extract | 1511 tumor bearer | 68.2 ± 4.2 |
| | 1511 extract | 1511 abs. 5.96 | 41.1 ± 4.3* |
| | 1511 extract | 1511 abs. 21D9 | 68.2 ± 4.7 |
| | 1511 extract | 5.96 eluate | 72.6 ± 4.1 |
| | 1511 extract | 21D9 eluate | 38.4 ± 3.3* | a Significant LAI compared with control containing the same PC and no antigen; P less than 0.01.
abs.: absorbed with Suppressive activity was removed by absorption with MAIA 5.96 but not with 21D9, and it was recovered in the corresponding eluate. SC supernatants related to BTCC-1660 were similarly absorbed (Table IX).

TABLE IX

MAIA 21D9 CAN ABSORB SF FROM SUPERNATANTS OF CULTURED SC FROM MICE BEARING BTCC-1660

| PC Donor | Antigen | SC Supernatant | % Adherence (mean ± SE) |
|---|---|---|---|
| 1660 tumor bearer | — | Medium only | 82.0 ± 3.4 |
| | 1660 extract | Medium only | 58.0 ± 3.3* |
| | 1660 extract | 1660 tumor bearer | 79.7 ± 3.0 |
| | 1660 extract | 1660 abs. 21D9 | 56.4 ± 5.7 |
| | 1660 extract | 1660 abs. 5.96 | 73.3 ± 5.0 |
| | 1660 extract | 21D9 eluate | 76.0 ± 3.3 |
| | 1660 extract | 5.96 eluate | 59.7 ± 2.6* |
| 21D9 sensitized | — | Medium only | 70.2 ± 3.6 |
| | 1660 extract | Medium only | 55.8 ± 2.7* |
| | 1660 extract | 1660 tumor bearer | 64.8 ± 3.5 |
| | 1660 extract | 1660 abs. 21D9 | 51.9 ± 3.5* |
| | 1660 extract | 1660 abs. 5.96 | 71.9 ± 4.0 |
| | 1660 extract | 21D9 eluate | 77.9 ± 2.7 |
| | 1660 extract | 5.96 eluate | 58.1 ± 2.7* |

*Significant LAI compared with control containing the same PC and no antigen; P less than 0.01.
abs.: absorbed with As shown in Table IX, the suppressive activity was removed by MAIA 21D9 but not by 5.96 and was recovered by elution of the 21D9 immunoabsorbent. In both cases, absorption of SF with the relevant MAIA fully restored LAI reactivity as tested with PC from either tumor-bearing or antibody-sensitized mice (Tables VIII, IX). The "crisscross" pattern of experimentation allows the conclusion that the absorption of SF activity by the appropriate MAIA was antigen specific.

7.4. MONOCLONAL ANTI-IDIOTYPIC ANTIBODIES CAN SPECIFICALLY NEUTRALIZE THE SUPPRESSIVE ACTIVITY OF TUMOR-BEARER SERUM OR SPLEEN CELL SUPERNATANTS

We studied whether the addition of MAIA to tumor-bearer serum or SC supernatants could neutralize its suppressive activity.

After the MAIA had been added to 1511 tumor-bearer serum or BTCC-1660 SC supernatant, the mixtures were tested for suppression of LAI reactivity to the corresponding tumors. Suppression was specifically and completely neutralized by the appropriate MAIA (Table X).

TABLE X

SPECIFIC "UNBLOCKING" ACTIVITY OF MAIA 21D9 AND 5.96

| PC Donor | Antigen | Source of SF | Antibody Added to SF | % Adherence (Mean ± SE) |
|---|---|---|---|---|
| 1660 tumor bearer | — | Medium only | — | 73.7 ± 3.5 |
| | 1660 extract | Medium only | — | 50.0 ± 3.1* |
| | 1660 extract | 1660 SC sup. | — | 78.2 ± 3.7 |
| | 1660 extract | 1660 SC sup. | 21D9 | 58.8 ± 3.1* |
| | 1660 extract | 1660 SC sup. | 5.96 | 79.0 ± 4.3 |
| 1511 tumor bearer | — | Normal serum | — | 87.9 ± 2.3 |
| | 1511 extract | Normal serum | — | 67.0 ± 3.5* |
| | 1511 extract | 1511 serum | — | 83.9 ± 3.4 |

TABLE X-continued

SPECIFIC "UNBLOCKING" ACTIVITY OF MAIA 21D9 AND 5.96

| PC Donor | Antigen | Source of SF | Antibody Added to SF | % Adherence (Mean ± SE) |
|---|---|---|---|---|
| | 1511 extract | 1511 serum | 21D9 | 88.4 ± 2.6 |
| | 1511 serum | 1511 serum | 5.96 | 62.9 ± 3.6* |

*Significant LAI compared with control containing the same PC and no antigen; P less than 0.01.
sup.: supernatant

7.5. MONOCLONAL ANTI-IDIOTYPIC ANTIBODIES SPECIFICALLY INHIBIT THE IN VITRO PRODUCTION (OR RELEASE) OF SUPPRESSOR FACTORS BY SPLEEN CELLS FROM TUMOR-BEARING MICE

We tested MAIA for the ability to inhibit the in vitro production (or release) of SF by SC from tumor-bearing mice. This was done in both the BTCC-1660 and sarcoma 1511 systems, using cultured SC from mice bearing the respective tumors as the source of SF, and PC from similar mice as the source of effector cells, for the assays. Results of two complete experiments are given in Table XI.

TABLE XI

EFFECT OF PRETREATMENT OF SC FROM TUMOR-BEARING MICE WITH ANTIBODIES AND COMPLEMENT (C) ON THE PRODUCTION OF SF IN CULTURE*

| Production of SF in | | Assay of SF on PC from Tumor-Bearing Mice | |
|---|---|---|---|
| SC Culture Supernatant | | | % Adherence |
| Source of SC | Pretreatment | Antigen | (mean ± SE) |
| — | — | — | 76.5 ± 3.2 |
| — | — | 1660 extract | 55.2 ± 4.2* |
| Normal mouse | Medium + C | 1660 extract | 51.6 ± 3.4* |
| 1660 tumor bearer | Medium + C | 1660 extract | 73.8 ± 4.0$^b$ |
| Normal mouse | Anti-Lyt-2.2 + C | 1660 extract | 58.1 ± 2.8* |
| 1660 tumor bearer | Anti-Lyt-2.2 + C | 1660 extract | 53.1 ± 2.3* |
| Normal mouse | 21D9 + C | 1660 extract | 59.2 ± 3.2* |
| 1660 tumor bearer | 21D9 +C | 1660 extract. | 57.5 ± 2.4* |
| Normal mouse | 5..96 + C | 1660 extract | 62.7 ± 2.6* |
| 1660 tumor bearer | 5.96 + C | 1660 extract | 77.2 ± 3.6$^b$ |
| — | — | — | 78.8 ± 2.7 |
| — | — | 1511 extract | 63.6 ± 2.6* |
| Normal mouse | Medium + C | 1511 extract | 68.2 ± 2.5* |
| 1511 tumor bearer | Medium + C | 1511 extract | 77.7 ± 3.0$^b$ |
| Normal mouse | 21D9 + C | 1511 extract | 62.1 ± 2.3* |
| 1511 tumor bearer | 21D9 + C | 1511 extract | 83.2 ± 2.4$^b$ |
| Normal mouse | 5.96 + C | 1511 extract | 68.3 ± 3.0* |
| 1511 tumor bearer | 5.96 + C | 1511 extract | 69.0 ± 2.3* |

*PC from 1660 tumor-bearing mice were mixed with 1660 extract to assay for 1660-specific SF, and PC from 1511 tumor-bearing mice were mixed with 1511 extract to assay for 1511-specific SF.
*Significant LAI compared to control containing the same PC and no antigen; P less than 0.01.
$^b$No significant LAI; significant suppression compared with equivalent supernatant from normal mouse SC.

The results in Table XI, which show that the in vitro production (or release) of SF from tumor bearing mice was specifically inhibited, have been confirmed on numerous occasions by more restricted experiments using single antibodies. All treatments of SC with antibodies were done in the presence of complement, and no tests with antibodies alone were carried out. If SC were treated with complement alone prior to culturing, SC supernatant from BTCC-1660-bearing mice, as compared to supernatant from normal mice, suppressed the LAI activity of immune PC. This result is shown in the upper part of Table XI. If, on the other hand, the same SC were pretreated with either anti-Lyt-2.2 or with MAIA 21D9, the SC culture supernatants no longer suppressed LAI reactivity. Pretreatment of SC with MAIA 5.96, specific for sarcoma 1511, had no effect on the production of SF related to BTCC-1660. The lower part of Table XI showns a reciprocal experiment with PC and SC from mice carrying sarcoma 1511. The results were analogous to those in the upper part of the table; MAIA 5.96, but not MAIA 21D9, completely suppressed the in vitro production (or release) of SF specific for the sarcoma. Whenever SF activity was seen in the presence of supernatant from tumor-bearer SC, but not in the presence of supernatant from identically treated control SC, the difference between the two groups was statistically significant (P less than 0.025 or better).

We have thus demonstrated that tumor-related SF can be complementary to the anti-idiotope in two distinct ways: MAIA were found to bind specifically to appropriate SF and to suppress the generation (and/or release) of SF from cultured SC.

The absence of detectable SF from most sera of BTCC-1660 tumor-bearing mice was contrary to our experience with other tumors. One may speculate that BTCC-1660 stimulates an anti-idiotypic response capable of neutralizing the SF production and/or activity, or that SF are removed from circulation by being continually bound to tumor antigens. The continued production of SF by mice bearing this tumor is suggested by our consistent detection of SF in SC cultures.

Mice bearing tumors would be expected to develop CMI and SF to multiple tumor-associated antigens. We have shown in the examples described supra in Section 6, that BTCC-1660 extract contains an antigen corresponding to antibody 6.10, plus other unrelated antigen(s). Thus one would expect that tumor-bearer serum and SC supernatant should contain multiple SF, related to various antigens. However, a single MAIA can absorb all suppressive activity (Tables VIII, IX), or prevent its appearance in culture (Table XI), as if the animals had produced SF related to only one epitope. These suprising results, observed here with two different tumors using LAI as the assay system, have been confirmed with a third tumor and its corresponding MAIA. In the latter case, all SF activity was absorbed from tumor-bearer serum by the MAIA, as assayed by suppression of delayed-type hypersensitivity to whole tumor cells. Thus, a single idiotope may dominate the suppressor pathway during tumor growth, which can be specifically recognized by the appropriate anti-idiotypic antibody.

Studies performed in a different system have demonstrated that the production (and/or release) of SF by tumor-bearer SC in vitro is carried out by Thy-1$^+$, Lyt-2$^+$, I-J$^+$ T cells interacting with macrophages (Koppi, T. A. and Halliday, W. J., 1983, Cell. Immunol. 76:29). We have shown in the examples described herein that cultured Lyt-2$^+$ SC from tumor-bearing mice are inhibited from making and/or releasing SF related to the given tumor, if they are pretreated with an appropriate MAIA (in the presence of complement). This implies that the putative suppressor cells from which the SF are released express an idiotope corresponding to the respective MAIA, probably as part of their antigen receptor. Since the effector cells recognizing tumor antigen in the LAI assay can be inactivated by the same MAIA (see Section 6, supra), they must express a similar idiotope. In the case of BTCC-1660, the idiotope is shared by antibody 6.10 as well as the SF in serum. The finding of a common idiotope on this network of cells and soluble factors in tumor-bearing animals is surprising in view of some previous data from other investigators. Yamauchi et al. (1979, J. Immunol. 123:1653) reported that different antigen determinants were recognized by cytotoxic and suppressor T cells in tumor-immunized mice, whereas Levy (1978, J. Immunol. 121:916) found that the blocking activity of serum from human patients with gliomas was specific for tumor determinants different from those to which cytotoxic T lymphocytes were directed.

The circulating tumor-specific SF and splenic suppressor T cells which we describe are elements of the suppressor cell/factor cascade. Idiotypes defined by MAIA can now be added to the list of characteristic features of the serum factors from tumor-bearing mice.

If suppressor cells (and factors) enhance tumor growth in vivo (Greene, M. I., et al., 1977, Proc. Natl. Acad. Sci. U.S.A. 74:5118; Hellstrom, K. E., et al., 1978, J. Exp. Med. 148:799; North, R. J., 1982, J. Exp. Med. 155:1063), a counteracting effect of MAIA can be immunotherapeutically valuable.

8. IMMUNOTHERAPY OF MURINE SARCOMAS WITH AUTO-ANTI-IDIOTYPIC MONOCLONAL ANTIBODIES WHICH BIND TO TUMOR-SPECIFIC T CELLS

According to the network theory (Jerne, N. K., 1974, Ann. Immunol. 125C:373; Rajewski, K. and Takemori, T., 1983, Ann. Rev. Immunol. 1:569; Urbain, J., et al., 1982, Ann. Immunol. 133D:179), mice forming an immune response to syngeneic sarcomas should have antibodies to the idiotypes of the responding lymphocytes. As described in the examples infra, based on this prediction, we immunized BALB/c mice to either of two syngeneic, transplanted fibrosarcomas, and formed hybridomas which produced monoclonal antibodies which primed syngeneic mice for tumor-specific DTH. One of these auto-anti-idiotypic monoclonal antibodies is shown to define an idiotope present both on T cells which have antitumor activity and on products of T suppressor cells, which inhibit this activity. We also show that treatment of mice with either of the two monoclonal anti-idiotypic antibodies significantly reduced growth of established sarcomas, an effect that was specific for the appropriate mAb-tumor combination.

8.1. MATERIALS AND METHODS

8.1.1. MICE

BALB/c mice were bred in the Division of Animal Health Resources, Fred Hutchinson Cancer Research Center (FHCRC), Seattle, Wash., and were matched for age and sex in each experiment. Females older than ten weeks were chosen since they gave optimal responses in pilot tests. CB-20 mice were raised at FHCRC from breeding pairs obtained from Dr. Michael Potter, National Institute of Health.

8.1.2. TUMORS

Fibrosarcomas MCA-1490, MCA-1510, and MCA-1511 were induced in BALB/c mice by intramuscular injection of 3-methylcholanthrene in trioctanoin and maintained by serial syngeneic transplantation of tissue frozen in the second generation. They were shown to be free of LDH, Sendai and ectromelia viruses, and from mycoplasma, and, like other chemically induced mouse sarcomas, to express individually unique tumor-specific transplantation antigens. BW5147.G.1.4.oua$^r$.1, is a drug-marked AKR thymoma which was obtained from the Cell Distribution Center of the Salk Institute. NS1 cells came from Dr. Ingegerd Hellstrom's laboratory. Both BW5147 and NS1 cells were shown to be free of mycoplasma.

8.1.3. ASSAY OF DELAYED-TYPE HYPERSENSITIVITY

An assay was used which measured delayed-type hypersensitivity (DTH) as mediated by Thy $1^+$,Lyt $1^+$ lymphocytes, and was characterized by the typical morphological manifestations of a DTH reaction (Forstrom, J. W., et al., 1983, Nature 303:627; Cory, J., et al., 1981, in Monoclonal Antibodies and T Cell Hybridomas, Hammerling, G. J., et al., eds., Elsevier/North-Holland Biomedical Press, p. 503). Mice were immunized by subcutaneous injection of either a total of $1 \times 10^6$ irradiated (15,000 rad) tumor cells into two sites, one on each flank, or by injection of 3–10 ug of mAb (diluted in phosphate-buffered saline, PBS) at four subcutaneous sites. When material was assayed for suppression of DTH, it was always assayed for suppression of its inductive phase. In these experiments, the putative suppressive material was diluted to 100 ul in PBS and injected into a tain vein immediately following immunization.

In each test for DTH, treatment or control groups consisted of 5 mice, and they were always coded. Five days after immunization, DTH was elicited by injection of $5 \times 10^5$ tumor cells into one of the two hind footpads. After 24 hours, the thickness of both the injected and the uninjected contralateral footpads was measured, using a dial micrometer. For each treatment group, the data are presented as the mean increase in thickness (i.e., the swelling) of the injected footpads. The significance of the differences between treatment groups and corresponding controls was determined using a two-tailed Student's t test.

8.1.4. GENERATION OF AUTO-ANTI-IDIOTYPIC MONOCLONAL ANTIBODIES

BALB/c mice were immunized by subcutaneous injection of $1 \times 10^7$ trypan blue unstained, cultured MCA-1490 or MCA-1511 cells, followed three weeks later by excision of the resulting tumor nodules. After two more weeks, the mice were injected with $2 \times 10^6$ irradiated (15,000 rads) cells from the respective tumors, and two weeks later they were injected once more with the same dose. Splenic cells were obtained 7 days after the last injection and fused to NS-1 myeloma cells, using techniques which have been described (Yeh, M. Y., et al., 1979, Proc. Natl. Acad. Sci. U.S.A. 76:2927).

Hybridomas were first screened for production of IgG antibodies using a radioimmunocompetition assay (Brown, J. P., et al., 1980, J. Biol. Chem. 255:4980), and those producing greater than 4 ug IgG per ml were expanded. Culture supernatants were pooled, with each pool consisting of supernatants from five hybridomas. Antibodies were purified from each pool by affinity chromatography on S. aureus protein A covalently coupled to Sepharose CL-4B (Sigma Chemical Co., St. Louis, Mo.) (Brown, J. P., et al., 1980, J. Biol. Chem. 255:4980). The pH of the antibody olutions was adjusted to 8.5 prior to chromatography to facilitate the isolation of $IgG_1$. BALB/c mice were immunized by injection with the pooled antibodies and five days later were challenged with the appropriate tumor cells (MCA-1490 or MCA-1511 cells) for elicitation of DTH. The individual supernatants of a pool testing positive were assayed for the priming of DTH to MCA-1490 and MCA-1511, with one of the two tumors serving as the control. Two to four percent of the wells from each fusion were found to contain antibodies with the desired activity. Hybridomas making antibodies that primed for tumor-specific DTH were cloned twice by limiting dilution, after which positive clones were expanded and adapted to grow as ascites tumors in pristane-primed BALB/c mice (Yeh, M. Y., et al., 1979, Proc. Natl. Acad. Sci. U.S.A. 76:2927). Monoclonal antibodies were purified from ascites fluid by affinity chromatography on protein A Sepharose. mAb 4.72 (relating to MCA-1490) and mAb 5.96 (relating to MCA-1511) were used for the present study. They were both of the IgG1 isotype, as was mAb 8.2, which was used as a control in some experiments.

8.1.5. T CELL HYBRIDOMAS

Several hybridoma lines were obtained by fusion of BW5147 cells with thymocytes of mice carrying MCA-1490 tumors, as previously described (Nelson, K. A., et al., 1980, Proc. Natl. Acad. Sci. U.S.A. 77:2866; Nelson, K., et al., 1985, in T-Cell Hybridomas, Taussig, M. J., ed., CRC Press, p. 129). The four hybridomas used in this study produced factors which suppressed the lysis of MCA-1490 cells by specifically immune T cells as tested in a $^{51}$Cr-release assay (Nelson, K., et al., 1985, supra). Cultures of these hybridomas and of the BW5147 fusion partner were grown in Dulbecco's modified Eagles' medium (Grand Island Biological Co., Grand Island, N.Y.), which was supplemented with fetal bovine serum (150 ul/ml), penicillin (100 units/ml), streptomycin (100 ug/ml) and L-glutamine (290 ug/ml), and was buffered with sodium bicarbonate. Spent medium was taken from cells in log phase growth when there were approximately $2 \times 10^6$ cells per ml. The medium was filtered (0.4 microns, Millipore) and stored at $-70°$ C. until assayed.

8.1.6. ISOLATION OF SUPPRESSOR FACTORS BY AFFINITY CHROMATOGRAPHY WITH mAb mAb 4.72 or 5.96 was used together with a control mAb, 8.2, which is also of the IgG1 isotype and is specific for a human melanoma antigen, p97 (Brown, J. P., et al., 1981, J. Immunol. 127:539). The mAb were diluted in PBS to 2 mg per ml and then coupled to an equal volume of Affi-Gel 10 (Bio-Rad Laboratories, Richmond, Calif.) by overnight incubation at 4° C. The gels were washed, incubated with 0.1M ethanolamine and used to prepare columns. The columns were washed extensively with PBS and pre-eluted with 3M NaSCN prior to use. Spent culture media of T cell hybridomas (as a source of suppressor factor) or BW5147 cells (as a control) were diluted 1:10 in PBS, after which 0.2 ml of the diluted media were passed through columns of 0.2 ml of gel. The columns were washed with PBS until 2 ml of effluent had been collected, after which the effluents were diluted 1:10 in PBS and assayed for suppression of the inductive phase of DTH.

Experiments were also performed with sera from BALB/c mice which had been transplanted with either MCA-1490 or MCA-1511 tumors or which were untreated littermates. The sera were diluted 1:10 in PBS, after which 0.5 ml of the diluted sera was passed through columns of 0.5 ml gel. The columns were washed with PBS. The first 1.5 ml was collected as effluent and an additional 5 ml was discarded. Bound proteins were then eluted from the columns by addition of 0.5 ml of 3M NaSCN, and the eluates were desalted by passage through columns of Sephadex G-25 equilibrated with PBS. Eluates and effluents were diluted in PBS to yield a 1:100 dilution relative to the original sera. They were subsequently tested for suppression of the inductive phase of DTH.

8.1.7. BINDING OF SUPPRESSOR FACTOR K54SF to MCA-1490 CELLS

Adherent cultured MCA-1490 cells were incubated in ethylene-diamine tetraacetic acid (5 mM), washed with PBS, and incubated in a 0.1% solution of glutaraldehyde for 10 minutes at 4° C. The cells were subsequently incubated in PBS with 0.5% bovine serum albumin, followed by washing with PBS. Spent culture media of T hybridoma I-K54 or control BW5147 cells were diluted 1:100 in PBS containing 10 ug of either mAb 4.72 or mAb 8.2 (as a control), and incubated on ice for 30 minutes. Subsequently, they were added to 100 ul of packed tumor cells, which were suspended and incubated at room temperature for 10 minutes and on ice for an additional 30 minutes. In one experiment, the tumor cells were pretreated by incubation with antibody and washed three times with PBS before the addition of diluted spent media from I-K54 or BW5147 cells. After incubation on ice, the tumor cells were washed 5 times with 15 ml of PBS and suspended in 0.5 ml of glycine-HCl buffer (pH 3.0). After further incubation on ice for 10 minutes, the cells were pelleted by centrifugation at 200×g. The pH of the supernatant was immediately adjusted by passage through Sephadex G-25 equilibrated with PBS. The eluates were diluted 1:10 in PBS and assayed for suppression of the inductive phase of DTH.

8.1.8. ISOLATION AND CULTURE OF T CELL LINES

T cells reacting with mAb 4.72 were obtained from lymph nodes draining the site of a progressively growing, transplanted MCA-1490 sarcoma. The cells were isolated by centrifugation on a Percoll gradient (Pharmacia) and mixed with mAb 4.72 or mAAb 8.2 coupled with biotin. Subsequently, they were washed, treated with avidin-fluorescein isothiocyanate (FITC), washed again and analyzed on a fluorescence-activated cell sorter (FACS-II, Becton-Dickinson). Brightly stained cells, which were seen only in the sample treated with mAb 4.72, and which represented less than 1% of the sample, were collected. These cells, termed 90.3, were cultured in Click's medium supplemented with 25% medium from a culture of rat spleen cells which had been stimulated with concanavalin A for 24 hours. Vigorous growth was observed after 25 days and was maintained by expanding the cultures into fresh medium every 72 hours. Another cell line, 11.2, was established from Lyt-1 positive lymphocytes which had been obtained from nodes draining the site of a MCA-1511 tumor; it was maintained in a way similar to line 90.3. The cells were assayed between 6 and 18 weeks after establishment of the 90.3 or 11.2 lines. Normal T cells from lymph nodes of tumor-free mice were cultured for 48 hours before they were used as controls for some of the assays.

8.1.9. IN VIVO MANIPULATION OF TUMOR GROWTH

Tumor tissue was obtained from mice 14-21 days after injection of tumor cells from serial passage. A suspension was prepared by mechanical disruption and brief treatment with trypsin. Viability was assessed by exclusion of trypan blue. In the experiment presented in FIG. 5, tumor cells were mixed with cultured T cells at a ratio of 1:10 and the mixture injected in one subcutaneous site. Ten mice were used per treatment group. Tumor growth was monitored at 2–4 day intervals by two perpendicular measurements of the growing tumor nodule. Tumors with an area greater than 0.2 cm$^2$ rarely regressed in untreated controls and were considered established tumors.

In the experiments measuring the effect of mAb treatment, tumor cells were injected subcutaneously in one site per mouse. mAb was diluted in PBS and injected intraperitoneally (ip.), 10 ug per injection. Tumor growth was monitored as described above. A two-tailed Student's t test was used to determine the significance of the difference between the various treatment groups.

8.2. SUBCUTANEOUS ADMINISTRATION OF mAb 4.72 OR mAb 5.96 INDUCES TUMOR-SPECIFIC DTH TO MCA-1490 and MCA-1511

We have previously reported that mAb 4.72 can induce DTH to MCA-1490, when injected subcutaneously, and that it reacts with an idiotope on tumor-specific cells, i.e., that it is auto-anti-idiotopic (Forstrom, J. W., et al., 1983, Nature 303:627). We have now developed a similar mAb, 5.96, using lymphocytes from mice sensitized to an antigenically different sarcoma, MCA-1511 (id.) This allowed us to assess the immunological specificity of the DTH effect by testing mAb 4.72 and 5.96 in parallel (Table XII).

TABLE XII mAbs 4.72 AND 5.96 PRIME BALB/C MICE FOR DTH THAT IS TUMOR-SPECIFIC AND ALLOTYPE RESTRICTED*

| Mouse Strain | Mice Injected with | Mean Footpad Swelling ($\times 10^{-3}$ in $\pm$ SE) in Mice Challenged with | |
|---|---|---|---|
| | | MCA-1490 | MCA-1511 |
| BALB/c (H-2$^d$, Igh-1$^a$) | mAb 4.72 | 15.3 ± 1.2† | 5.0 ± 1.6 |
| | MCA-1490 cells | 18.4 ± 1.6† | Not done |
| | mAb 5.96 | 8.0 ± 1.2 | 13.7 ± 0.3† |
| | MCA-1511 cells | Not done | 18.7 ± 0.9† |
| | Diluent | 8.3 ± 1.2 | 5.0 ± 1.8 |
| CB-20 (H-2$^d$, Igh-1$^b$) | mAb 4.72 | 7.7 ± 0.4 | 6.7 ± 0.3 |
| | MCA-1490 cells | 18.3 ± 0.9† | Not done |
| | mAb 5.96 | 8.2 ± 0.6 | 6.7 ± 1.2 |
| | MCA-1511 cells | Not done | 20.0 ± 1.8† |
| | Diluent | 8.0 ± 1.2 | 5.3 ± 0.6 |

*Five mice in each group were injected subcutaneously with 5 ug of mAb or 10$^6$ tumor cells in 100 ul. Five days later, all mice were given 5 × 10$^5$ tumor cells in 20 ul into one hind footpad. The increase in the thickness (swelling) of the injected pad over the contralateral pad was determined 24 hours later and is presented as the mean (± SE) for each group.
†The response of these mice was significantly greater than that of mice injected with diluent at P less than 0.01 by Student's t test.

As shown in Table XII, BALB/c mice primed with mAb 4.72 responded with DTH to a subsequent challenge with MCA-1490 cells but not to challenge with MCA-1511 cells. mAb 5.96 behaved in an analogous way in that it primed BALB/c mice for DTH to MCA-1511 but not MCA-1490. The specificity of the DTH indicates that different idiotopes were involved in the immune responses to MCA-1490 and MCA-1511.

In agreement with previous data for mAb 4.72 (Forstrom, J. W., et al., 1983, Nature 303:627), the priming required identity at genes linked to the Igh-1 allotype locus (Table XII), since neither of the two mAb primed CB-20 mice. Immunization with tumor cells did induce DTH in the CB-20 mice. When tested with antibody binding assays (Cory, J., et al., 1981, in Monoclonal Antibodies and T Cell Hybridomas, Hammerling, G. J., et al., eds., Elsevier/North-Holland Biomedical Press, p. 503), mAb 5.96 was similar to mAb 4.72 (Forstrom, J. W., et al., 1983, Nature 303:627) in that it did not bind to sarcoma cells.

We conclude that mAb 4.72 and mAb 5.96 are functionally anti-idiotopic to the immune responses to MCA-1490 and MCA-1511, respectively.

8.3. INTRAVENOUS ADMINISTRATION OF mAb 4.72 SUPPRESSES DTH TO MCA-1490

We tested the effect of intravenous (i.v.) administration of mAb 4.72 on the DTH reactivity of mice which had been immunized by subcutaneous injection of either mAb 4.72 or MCA-1490 cells or with MCA-1511 cells, the latter being used as control. Immediately following the subcutaneous immunization, mice were injected via a tail vein with approximately 5 ug of mAb 4.72 or mAb 8.2 (as a control). The DTH response was measured 5 days later (Table XIII).

TABLE XIII mAb 4.72 SUPPRESSES DTH TO MCA-1490 WHEN INJECTED INTRAVENOUSLY (I.V.) INTO MICE IMMEDIATELY AFTER IMMUNIZATION BY SUBCUTANEOUS INJECTION OF EITHER mAb 4.72 OR MCA-1490 TUMOR CELLS*

| Mice Immunized with | Mice Challenged with | Antibody (or Fab fragments) Injected i.v. | Mean Footpad Swelling ($\times 10^{-3}$ in. ± SE) |
|---|---|---|---|
| mAb 4.72 | MCA-1490 | mAb 4.72 | 4.8 ± 0.8† |
| | | mAb 8.2 | 12.2 ± 0.7 |
| | | None (diluent) | 13.6 ± 0.5 |
| MCA-1490 | MCA-1490 | mAb 4.72 | 6.8 ± 1.6† |
| | | Fab 4.72 | 7.2 ± 1.3† |
| | | mAb 8.2 | 17.0 ± 1.3 |
| | | None (diluent) | 19.8 ± 0.7 |
| Nothing | MCA-1490 | None | 4.0 ± 0.9 |
| MCA-1511 | MCA-1511 | mAb 4.72 | 15.0 ± 2.6 |
| | | Fab 4.72 | 15.6 ± 1.2 |
| | | mAb 8.2 | 14.8 ± 2.1 |
| | | None (diluent) | 16.4 ± 2.6 |
| Nothing | MCA-1511 | None | 4.6 ± 1.3 |

*Mice were immunized by subcutaneous injection, and DTH was measured as described for Table XII. Material assayed for suppression of DTH was diluted, and 100 ul injected i.v. immediately following immunization. Each mouse received 5 ug of whole mAb or 3.5 ug of Fab fragments.
†The response of these mice was significantly lower than that of mice receiving diluent at P less than 0.001 according to Student's t test.

As shown in Table XIII, i.v. injection of mAb 4.72 suppressed the ability of subcutaneously injected mAb 4.72 or MCA-1490 cells to prime mice for DTH to MCA-1490. Furthermore, i.v. injection of Fab fragments prepared from mAb 4.72 suppressed immunization with MCA-1490 cells. Immunization with MCA-1511 cells was not suppressed, and i.v. injection of a control mAb, 8.2, had no effect.

We conclude that the route of administration influenced the DTH reactivity of mice receiving mAb 4.72, with subcutaneous injection inducing DTH (see Section 8.2., supra) and i.v. injection suppressing this effect.

8.4. EXPRESSION OF AN IDIOTOPE DEFINED BY mAb 4.72 ON T CELLS MEDIATING DTH TO MCA-1490

We studied whether the mAb 4.72 defined idiotope was present on T cells mediating DTH to MCA-1490. Mononuclear cells from lymph nodes draining a growing MCA-1490 tumor were analyzed on a fluorescence-activated cell sorter (FACS) using mAb 4.72 coupled to biotin and avidin-FITC. Brightly stained cells were observed. Although the brightly stained cells represented less than one percent of the total population of mononuclear cells, they were not seen in samples analyzed with a biotinylated control monoclonal antibody, mAb 8.2, used at the same dose. The stained cells were isolated and cultured in the presence of interleukin-2 (IL-2), from which a cell line was established, which was called 90.3. When the 90.3 cells were analyzed for surface phenotype after six weeks of culture, they bound mAb 4.72, although the fluorescence intensity was lower than that of the original cells. These cells were Thy-1 positive and expressed Lyt-1 but not Lyt-2 antigens.

We then investigated the effect of the 90.3 cells on the DTH response to MCA-1490 (Table XIV).

TABLE XIV

TUMOR-SPECIFIC DTH IS TRANSFERRED BY
T CELLS FROM LINES 90.3 AND 11.2*

| Mice Injected with Mixture of | | Mean Footpad Swelling | |
|---|---|---|---|
| Tumor Cells | Effector Cells | ($\times 10^{-3}$ in. $\pm$ SE) | |
| | | Experiment 1 | Experiment 2 |
| MCA-1490 | 90.3 | 19.2 ± 1.6† | 15.0 ± 2.2† |
| MCA-1490 | Normal T | 9.6 ± 1.1 | 4.8 ± 0.6 |
| MCA-1490 | None (diluent) | 7.0 ± 0.7 | 4.0 ± 0.4 |
| MCA-1511 | 90.3 | 9.4 ± 1.0 | 4.0 ± 0.4 |
| MCA-1511 | 11.2 | 17.3 ± 2.6 | 10.7 ± 1.2† |
| MCA-1511 | Normal T | 10.2 ± 2.3 | 3.0 ± 0.3 |
| MCA-1511 | None (diluent) | 8.0 ± 0.7 | 3.0 ± 0.4 |
| None (diluent) | 90.3 | 0.4 ± 1.2 | 0.2 ± 0.4 |
| None (diluent) | 11.2 | 2.6 ± 0.6 | 1.2 ± 0.6 |
| None (diluent) | Normal T | 4.8 ± 1.0 | 3.6 ± 1.2 |

*Effector T cells (2 × 10⁵) derived from lines 90.3 or 11.2 or from naive BALB/c mice were mixed with MCA-1490 or MCA-1511 cells (5 × 10⁵) and injected into one footpad of a naive BALB/c mouse. Five mice were used per group. After 24 hours, DTH was measured and calculated as described in Table XII.
†The response of these mice was significantly greater than that of mice receiving diluent and MCA-1490 cells at P less than 0.02 by Student's t test.

As shown in Table XIV, there was DTH to MCA-1490 when mixtures of 90.3 cells and MCA-1490 cells were injected into the footpads of naive BALB/c mice. There was no DTH to MCA-1511, and neither was there any footpad swelling in mice which received only the 90.3 cells but no MCA-1490 cells. A second line of T cells, 11.2, was established from lymph nodes of mice draining the antigenically different sarcoma MCA-1511. The 11.2 line gave DTH to MCA-1511 but not to MCA-1490. Lymph node cells from naive mice were cultured in medium containing IL-2 for 48 hours prior to the assays and was used as another control; they did not transfer DTH to MCA-1490.

90.3 cells, which had been cultured for nine weeks, were tested for their effect on the in vivo growth of the MCA-1490 tumor. Cultured T cells from naive mice were used as controls. The T cells were mixed with MCA-1490, MCA-1510 or MCA-1511 tumor cells; each mixture was injected subcutaneously into ten naive BALB/c mice. Time to appearance of tumors was monitored, as well as the growth rate of the tumors. As shown in FIG. 5, one of ten mice which had received a mixture of MCA-1490 together with 90.3 cells developed palpable tumors, as compared to nine of ten mice in which control T cells rather than 90.3 cells were admixed. The 90.3 cells had no effect on two antigenically different sarcomas, MCA-1510 or MCA-1511.

We conclude that mAb 4.72 reacted with a small population of T cells from mice bearing sarcoma MCA-1490, and that cell line 90.3, which was derived from such cells, was specifically reactive to MCA-1490.

8.5. EXPRESSION OF AN IDIOTOPE RECOGNIZED BY mAb 4.72 ON FACTORS DERIVED FROM SUPPRESSOR T CELLS

We have previously described the generation of T-T hybridomas by fusing T cells from mice bearing sarcoma MCA-1490 (Nelson, K. A., et al., 1980, Proc. Natl. Acad. Sci. U.S.A. 77:2866). The monoclonal products (suppressor factors) made by four of these hybridomas, I-K54, II-15, II-32, and II-122, have been demonstrated to suppress DTH to MCA-1490, but not to MCA-1511, and to bind specifically to MCA-1490 cells, while they differed as to the kinetics and genetic restriction of their suppression (Nelson, K., et al., 1985, in T-Cell Hybridomas, Taussig, M. J., ed., CRC Press, p. 129).

We selected one of the four suppressor factors, K54SF, to test whether the idiotope defined by mAb 4.72 was associated with the portion of that factor which could bind to MCA-1490. K54SF (obtained from supernatant of cultured I-K54 cells) and MCA-1490 cels were inoculated together, after which the tumor cells were washed and any K54SF that had bound to them was eluted. Suppression was assayed by DTH tests after injecting the eluates i.v. into mice immediately after these had been immunized subcutaneously with MCA-1490 or MCA-1511 cells. Tumor-specific suppressive activity was recovered in the eluates.

The ability of mAb 4.72 to inhibit the binding of K54SF to MCA-1490 was investigated in more detail. Medium containing K54SF was mixed with either mAb 4.72 or mAb 8.2 (control) before it was added to MCA-1490 cells, and eluates of the cells were tested for suppression (Table XV).

TABLE XV

INCUBATION OF K54SF (A SUPPRESSOR FACTOR MADE BY T-T HYBRIDOMA I-K54) WITH mAb 4.72 INHIBITS ITS BINDING TO MCA-1490 CELLS*

| Anti-MCA-1490 Immune Mice Injected with | | | Mean Footpad Swelling ($\times 10^{-3}$ in. ± SE) in Mice Challenged with MCA-1490 | |
|---|---|---|---|---|
| Source of Suppressor Factor (medium) | Suppressor Factor First Mixed with | Subsequently Incubated with and Eluted from | Experiment 1 | Experiment 2 |
| I-K54 | mAb 8.2 | MCA-1490 | 6.4 ± 0.6† | 4.0 ± 0.7† |
| I-K54 | mAb 4.72 | MCA-1490 | 15.6 ± 1.1 | 15.2 ± 0.9 |
| BW5147 (control) | mAb 8.2 | MCA-1490 | 17.4 ± 0.9 | Not done |
| BW5147 (control) | mAb 4.72 | MCA-1490 | 17.2 ± 1.6 | Not done |
| I-K54 | Diluent | MCA-1490 pre-incubated with mAb 8.2 | Not done | 6.6 ± 1.5† |
| I-K54 | Diluent | MCA-1490 pre-incubated with mAb 4.72 | Not done | 17.6 ± 1.2† |

*Media of I-K54 or BW5147 (control) cells were first mixed with mAb 4.72 or mAb 8.2, after which they were incubated with MCA-1490 cells. In Experiment 2, there were also groups (lines 5 and 6 in the Table) in which MCA-1490 cells were incubated with mAb 8.2 or mAb 4.72, before they were incubated with I-K54 medium. After incubation, the tumor cells were washed, and material bound to them was eluted and assayed for suppression of DTH to MCA-1490. Mean footpad swelling in unimmunized (control) mice was 5.0 ± 0.3 in Experiment 1 and 5.2 ± 0.6 in Experiment 2, and mean footpad swelling in anti-MCA-1490 immune mice challenged with MCA-1490 was 15.8 ± 1.4 in Experiment 1 and 17.6 ± 1.0 in Experiment 2.
†The response of these mice was significantly lower than that of mice receiving diluent at P less than 0.001 by Student's t test.

As shown in Table XV, eluates of MCA-1490 cells which had been incubated with a mixture of mAb 8.2 and K54SF, suppressed DTH to MCA-1490. In contrast, eluates of MCA-1490 cells incubated with a mixture of K54SF and mAb 4.72 were not suppressive. This result indicates that the ability of K54SF to bind to MCA-1490 was inhibited by its binding to mAb 4.72. Eluates of MCA-1490 cells which had been incubated with BW5147 (control) medium and mAb 8.2 were not suppressive; thus suppression was not due to eluted tumor antigen. Pretreatment of MCA-1490 cells with mAb 4.72 did not prevent them from binding K54SF (see line 6 of Table XV), and thus the inhibition seen when K54SF was incubated with mAb 4.72 was not due to competition between mAb 4.72 and K54SF for binding to antigen on MCA-1490 cells. The results suggest that the idiotope recognized by mAb 4.72 is expressed at the site of K54SF which binds to MCA-1490 or, at least, in close proximity to that site. Similar results were obtained for the suppressor factor produced by a T cell hybridoma, II-32.

Since K54SF suppresses DTH to MCA-1490, we assayed the effect of K54SF on the function of 90.3 cells, since these cells could transfer DTH specific to MCA-1490 (see Section 8.4, supra). Mice were injected, in one footpad, with a mixture of cells from the 90.3 line and cells from the MCA-1490 tumor. One hour later, K54SF (as supernatant of the I-K54 hybridoma) was injected into the same footpad; BW5147 supernatant was used as control. As shown in Table XVI, injection of K54S F suppressed the ability of the 90.3 cells to mediate DTH to MCA-1490.

TABLE XVI

DTH TO MCA-1490, AS TRANSFERRED BY T CELLS FROM LINE 90.3, IS SUPPRESSED BY A FACTOR PRODUCED BY T-T HYBRIDOMA I-K54*

| Cells Transferring DTH | Source of Suppressor Factor (culture medium) | Mean Footpad Swelling ($\times 10^{-3}$ in. $\pm$ SE) | |
|---|---|---|---|
| | | Experiment 1 | Experiment 2 |
| 90.3 | None (diluent) | 19.2 ± 1.6 | 15.0 ± 2.2 |
| | I-K54 1.0 ul | 8.2 ± 0.8† | Not done |
| | I-K54 0.1 ul | 9.4 ± 0.9† | 3.0 ± 0.4† |
| | BW5147 1.0 ul | 20.3 ± 1.4 | Not done |
| | BW5147 0.1 ul | 19.6 ± 1.6 | 13.3 ± 1.2 |
| Normal T | None (diluent) | 9.6 ± 1.1 | 4.8 ± 0.6 |
| Diluent | None (diluent) | 7.0 ± 0.7 | 4.0 ± 0.6 |

*Line 90.3 T cells were mixed with MCA-1490 cells an injected into the footpads of naive BALB/c mice to assay for DTH, as described in Table XIV. Medium of I-K54 or BW5147 (control) cells was diluted to 5 ul and injected into the same footpad as the T cell-tumor cell mixture. Five mice were used per group.
†The response of these mice was significantly lower than that of mice receiving 90.3 cells, tumor cells and diluent, at P less than 0.01 by Student's t test.

Since both 90.3 effector cells and K54 suppressor cells appeared to carry a mAb 4.72-defined idiotope, we evaluated whether this idiotope was present also on suppressor factors made by T cell hybridomas other than K54. Suppressor factors derived from four different T cell hybridomas were assayed for suppressive activity after incubation with immobilized mAb 4.72. Spent medium from the four hybridomas and from BW5147 (control) cells, was passed through columns of either mAb 4.72 or mAb 8.2 (control), which had been covalently coupled to agarose. The effluents were assayed for suppression of DTH to MCA-1490, by injecting them i.v. into BALB/c mice immediately after they had been subcutaneously immunized to MCA-1490 (Table XVII).

TABLE XVII mAb 4.72 BINDS TO FACTORS WHICH ARE PRODUCED BY T CELL HYBRIDOMAS AND WHICH SUPPRESS DTH TO MCA-1490*

| Source of Suppressor Factors (culture medium from) | Mean Footpad Swelling ($\times 10^{-3}$ in. $\pm$ SE) in Mice Injected with Medium Adsorbed with | |
|---|---|---|
| | mAb 8.2 | mAb 4.72 |
| BW5147 (control) | 24.2 ± 1.8 | 23.4 ± 0.8 |
| Hybridoma I-K54 | 7.8 ± 1.0† | 22.9 ± 1.2 |
| Hybridoma II-15 | 9.6 ± 2.8** | 18.4 ± 2.2 |
| Hybridoma II-32 | 10.8 ± 2.0** | 24.8 ± 2.4 |
| Hybridoma II-122 | 11.0 ± 1.2† | 23.6 ± 2.0 |

*Spent culture medium of T cell hybridomas I-K54, II-15, II-32 and II-122 or of BW5147 (control) cells were passed through columns of mAb 4.72 or 8.2 covalently coupled to agarose. The effluents were assayed for suppression of the inductive phase of DTH to MCA-1490 as described in Table XIII. Statistical significance of differences in footpad swelling, as compared to control mice receiving diluent was estimated by Student's t test.
†P less than 0.001
** P less than 0.01

As shown in Table XVII, media derived from each of the four T hybridomas and passaged through a control column (of mAb 8.2) suppressed the induction of DTH to MCA-1490, while this suppression was removed by passage through a mAb 4.72 column. All four suppressor factors thus appeared to express the idiotope defined by mAb 4.72.

This result suggested that the idiotope defined by mAb 4.72 was dominant in regulating the suppressor response to MCA-1490. However, as factors made by only four hybridomas were studied, we next analyzed the presumably polyclonal suppressor response in mice bearing a growing MCA-1490 sarcoma. This experiment was done on the basis of the demonstration that sera from mice carying MCA-1490 or MCA-1511 sarcomas can suppress the induction of DTH to the respective tumors (Table XVIII).

TABLE XVIII

SERA FROM MICE BEARING SARCOMA MCA-1490 OR MCA-1511 SUPPRESSES DTH TO THE RESPECTIVE TUMOR*

| Serum Donor | Mean Footpad Swelling ($\times 10^{-3}$ in. $\pm$ SE) in Mice Immunized and Challenged with | |
|---|---|---|
| | MCA-1490 | MCA-1511 |
| MCA-1490 tumor-bearer mice | 6.7 ± 1.3† | 20.0 ± 0.4 |
| MCA-1511 tumor-bearer mice | 15.9 ± 2.6 | 10.4 ± 2.3† |
| Naive mice | 17.5 ± 4.5 | 22.2 ± 2.6 |
| None (diluent) | 15.0 ± 1.4 | 21.0 ± 1.4 |

*Sera from mice bearing progressively growing MCA-1490 or MCA-1511 tumors or from control mice were diluted and 100 ul injected i.v. into mice immediately before immunization to MCA-1490 or MCA-1511. DTH was elicited and measured as described in Table XII. Mean footpad swelling in unimmunized mice was 5.3 ± 1.2 after challenge with MCA-1490 and 6.3 ± 0.3 after challenge with MCA-1511.
†The response of these mice was significantly lower than that of mice receiving diluent at P less than 0.01 by Student's t test.

Sera from tumor-bearing mice were chromatographed on columns of mAb 4.72 or mAb 8.2 (control), the material bound to the columns was eluted, and effluents and eluates were assayed for suppression of DTH (Table XIX).

TABLE XIX mAb 4.72 BINDS SERUM FACTORS WHICH SUPPRESS DTH TO MCA-1490
BUT DO NOT BIND SERUM FACTORS WHICH SUPPRESS DTH TO MCA-1511*

| Mice | | | Intravenously injected | | | |
|---|---|---|---|---|---|---|
| Immunized with | Challenged with | Sera | Immuno-adsorbed on Column Pre-pared with | Fraction from Immuno-adsorbent Column | Mean Footpad Swelling ($\times 10^{-3}$ in. $\pm$ SE) | |
| | | | | | Experiment 1 | Experiment 2 |
| MCA-1490 | MCA-1490 | MCA-1490 tumor-bearer | mAb 8.2 | Effluent | 6.0 ± 1.3† | 6.0 ± 1.4† |
| | | | mAb 8.2 | Eluate | 16.6 ± 0.7 | Not done |
| | | | mAb 4.72 | Effluent | 15.0 ± 1.0 | 16.0 ± 2.0 |
| | | | mAb 4.72 | Eluate | 7.2 ± 0.8† | 8.0 ± 1.3† |
| | | None (diluent) | — | — | 15.0 ± 1.4 | 15.0 ± 0.3 |
| None (unimmunized) | MCA-1490 | None | | | 5.3 ± 1.2 | 6.3 ± 0.7 |
| MCA-1511 | MCA-1511 | MCA-1511 tumor-bearer | mAb 8.2 | Effluent | 10.2 ± 1.2† | 10.2 ± 1.2† |
| | | | mAb 8.2 | Eluate | 19.2 ± 2.0 | Not done |
| | | | mAb 4.72 | Effluent | 9.8 ± 1.6† | 9.8 ± 1.2 |
| | | | mAb 4.72 | Eluate | 16.8 ± 1.5 | 15.8 ± 1.2 |
| | | None (diluent) | — | — | 21.0 ± 1.4 | 17.6 ± 0.8 |
| None (unimmunized) | MCA-1511 | None | | | 6.3 ± 0.3 | 5.7 ± 0.7 |

*Sera from mice bearing MCA-1490 or MCA-1511 tumors were passed through immunoadsorbent columns of mAb 4.72 or mAb 8.2, covalently coupled to agarose. The columns were washed, and bound material was eluted with 3 M NaSCN and desalted on Sephadex G-25 which had been equilibrated with PBS. The effluents and eluates of each column were assayed for suppression of the inductive phase of DTH as described in Tables XIII and XVI.
†The response of these mice was significantly lower than that of immunized mice receiving diluent at P less than 0.01 by Student's t test.

As shown in Table XIX, sera from mice bearing MCA-1490 suppressed DTH to MCA-1490 after passage through a control column (of mAb 8.2) but not after passage through a mAb 4.72 column, and material which suppressed DTH to MCA-1490 was recovered in an eluate of the latter column. Immunoadsorption with mAb 4.72 did not remove the ability of sera from mice bearing a different tumor, MCA-1511, to suppress DTH to that tumor.

Our results indicate that suppression of DTH to MCA-1490 was associated with an idiotope recognized by mAb 4.72 and that suppression of DTH to MCA-1511 did not involve that idiotope.

8.6. SEROTHERAPY OF MICE WITH MCA-1490 OR MCA-1511 TUMORS

We investigated whether injection of mAb 4.72 and 5.96 protected mice against challenge with the appropriate tumor cells (MCA-1490 or MCA-1511, respectively) and whether it had any therapeutic effect on established tumors. The mAb were injected intraperitoneally; the i.v. route was not chosen in view of the evidence (see Section 8.3, supra) that mice so injected showed decreased DTH reactivity to tumor antigens.

In the first set of experiments, mice (20 per group) were injected with either mAb 4.72 or (control) mAb 8.2. They were challenged, 5 days later, with MCA-1490 cells at a dose which, according to pilot tests, caused progressive tumor growth in approximately 90% of the recipients. Priming with mAb 4.72 delayed the appearance of transplanted MCA-1490 sarcoma by 5 to 9 days compared to controls, but there was no significant difference between the percentage of mice dying from progressively growing tumors. The growth of the antigenically unrelated MCA-1511 sarcoma was not affected. Varying the amount of mAb 4.72 injected did not improve the results. Rather, in one experiment in which ice received 100 times the amount of mAb 4.72 which could rime for DTH, the growth of MCA-1490 was accelerated as compared to both control mice and control tumors. A dual effect has also been reported in the manipulation of immunity to viral antigens, using anti-idiotypic antibodies (Kennedy, R. C. and Dreesman, G. R., 1984, J. Exp. Med. 159:655; Kennedy, R. C., et al., 1984, J. Virol. 50:951).

In a second series of experiments, mice were first injected with MCA-1490 cells subcutaneously, and this was followed 7 or 8 days later by 100 ug mAb i.p.; at this point in time, tumors had become barely palpable in about 50% of the mice. The antibody injection was repeated at 4 to 5 day intervals for a total of four injections. In all of the 10 mice given mAb 4.72, the original small tumor nodules had regressed when the experiment was terminated after 6 weeks. At that time, 6 of 10 mice given the control mAb 8.2 had progressively growing tumors with a surface area greater than or equal to 0.20 cm². This difference between the two groups was significant at P less than or equal to 0.05.

To test the limits of this form of therapy, the dose of tumor cells was increased by giving tumor cells at a dosage twice that required to grow out in 100% of the recipients. The two antigenically distinct sarcomas, MCA-1490 and MCA-1511, were treated in parallel with the appropriate anti-idiotopic mAb (4.72 and 5.96, respectively). Groups of ten mice were injected with mAb 4.72 (related to MCA-1490), mAb 5.96 (related to MCA-1511), mAb 8.2 (as a control), or diluent (as another control), starting nine days after transplantation when all the mice had barely palpable tumors (greater than 0.2 cm²). As shown in FIG. 6, treatment with mAb 4.72 limited the growth of MCA-1490, but not of MCA-1511, and treatment with mAb 5.96 similarly inhibited MCA-1511, but not MCA-1490. The differences between mice receiving the appropriate anti-idiotopic mAb and any of the three controls (the inappropriate anti-idiotopic mAb, mAb 8.2 or diluent) was statistically significant at P less than or equal to 0.001. FIG. 7 presents these data in more detail by showing the number of mice with tumors in each group treated with mAb 4.72 or mAb 5.96. In each of the two groups receiving appropriate anti-idiotopic antibody, tumors regressed in 5 or 7 of the 10 treated mice, and three of these mice (in each of the two groups) remained free of tumor for two weeks after the last injection of antibody. At that time, all the mice in the control groups had tumors with a surface area greater than 1.5 cm$^2$, and some of the mice had already died with tumor.

We conclude that treatment of mice with established sarcomas MCA-1490 and MCA-1511, using intraperitoneal injection of the appropriate anti-idiotopic mAb, had significant antitumor activity.

8.7. DISCUSSION

We herein describe evidence that T cells and anti-idiotypic B cells were generated in mice which either bore a growing sarcoma or had been immunized to such a tumor. T cells bearing the same idiotope included cells which mediated tumor-specific DTH and cells which made a soluble, tumor-specific suppressor factor. By employing anti-idiotopic mAb, we could manipulate the antitumor response so as to limit the growth of established syngeneic sarcomas expressing the relevant tumor antigens.

Two mAb, 4.72 and 5.96, were used. They were isolated from BALB/c mice which had been immunized to sarcomas MCA-1490 or MCA-1511, respectively. We regard the two mAb as anti-idiotopic in view of three findings which relate to their functions. First, each mAb induced tumor-specific DTH in syngeneic mice in the absence of tumor antigen. Second, this induction was allotype restricted. Third, neither mAb bound to the immunizing tumor.

The idiotope defined by mAb 4.72 was identified on T cells which mediated DTH to MCA-1490. This was done in an experiment in which mAb 4.72 was used to isolate from lymph nodes of mice responding to MCA-1490, a small fraction of lymphocytes which expressed the 4.72-defined idiotope and from which a T cell line, 90.3, could be established. Naive mice receiving the 90.3 cells displayed DTH to MCA-1490 but not to MCA-1511, and the 90.3 cells prevented the outgrowth of sarcoma MCA-1490 but not sarcoma MCA-1510 or MCA-1511. Cheever et al. (1986, J. Exp. Med. 163:1100) have demonstrated the ability of Lyt 1$^+$2$^-$ T cells to limit the progression of murine leukemia. However, their protocol includes restimulation of the cultured cells with antigen as well as IL-2. The tumor specificity of the 90.3 cells argues against their being lymphokine-activated killer cells.

Products of T cells which suppressed the DTH response to MCA-1490 were found to express the idiotope defined by mAb 4.72. This was shown in studies on four T cell hybridomas which had been obtained by fusing thymocytes from mice carrying growing MCA-1490 tumors with BW5147 cells (Nelson, K., et al., 1985, in T-Cell Hybridomas, Taussig. M. J., ed., CRC Press, p. 129). The products of these previously bed previously been found to suppress the lysis of $^{51}$Cr labelled MCA-1490 cells by specifically immune cytolytic T cells (Nelson, K. A., et al., 1980, Proc. Natl. Acad. Sci. U.S.A. 77:2866) and to suppress the induction of DTH to MCA-1490 (Cory. J., et al., 1981 in Monoclonal Antibodies and T Cell Hybridomas, Hammerling, G. J., et al, eds., Elsevier/North-Holland Biomedical Press, p. 503); this suppression was specific for the response to MCA-1490 and was allotype restricted. Furthermore, the suppressor factors had been found to bind to MCA-1490 cells from which they could be recovered by elution (Nelson, K. A., et al., 1980, supra). In the examples described herein, we demonstrate that mAb 4.72 inhibits the binding of all four suppressor factors to MCA-1490 cells. This suggests that the idiotope defined by mAb 4.72 is associated with the site on the suppressor factor which binds to a tumor antigen on MCA-1490 cells. T suppressor factors bearing the idiotope defined by mAb 4.72 could both suppress the priming for DTH by mAb 4.72 and the transfer of DTH to MCA-1490 by T cells from line 90.3 (which, as discussed supra, express the mAb 4.72-defined idiotope).

Based on these data, we suggest the following model: mAb 4.72 defines an idiotope which occurs on tumor-specific regulatory T cells and is dominant in the immune response of BALB/c mice to MCA-1490. During this response, the same or a cross-reacting idiotope activates a B cell clone producing anti-idiotypic antibody. The latter antibody is presumed to regulate both suppressor T cells and DTH-reactive T cells. Our model assumes, as supported by various studies (Rajewski, K. and Takemori, T., 1983. Ann. Rev. Immunol. 1:569; Urbain, J., et al., Ann. Immunol. 133D:179; Binz, H. and Wigzell, H., 1978, J. Exp. Med. 147:63; Ertl, H. C. J., et al., 1982, Proc. Natl. Acad Sci. U.S.A. 79:7479), that T and B cells interact in idiotypic networks. Our model also assumes that a B cell derived anti-idiotypic antibody (mAb 4.72 in our example) arose in response to a T cell idiotope and not to a parallel set of idiotope-positive B cells. In support of this, we have no evidence for tumor cell binding antibody in the response of mice to MCA-1490, nor have we been able to induce such antibody by immunizing with mAb 4.72. This is in contrast with the ease in demonstrating idiotope-positive, antigen-reactive T cells. The data support the hypothesis that a T cell idiotope can induce an anti-idiotypic response in the B cell compartment, which in its turn can regulate T cell responses in both upwards and downwards directions.

An alternative model assumes that the mAb 4.72-defined idiotope displays an internal image of the MCA-1490 tumor antigen. However, it is difficult to reconcile that model with the allotype (Igh-1) restriction of the induction of DTH by mAb 4.72.

In the present study, we used the anti-idiotopic mAb 4.72 in a successful attempt to remove the suppressive activity of sera from mice bearing MCA-1490. All the circulating serum factors which could be detected by measuring suppression of DTH to MCA-1490 appeared to express the 4.72-defined idiotope.

As described supra, we next examined the feasibility of manipulating the immune response to tumor by using anti-idiotypic mAb. mAb 4.72 and 5.96 were chosen, as they could both induce DTH reactive cells in naive mice, and as the idiotope defined by one of the mAb, 4.72, was expressed on DTH reactive cells in immune mice. Our first set of experiments addressed the question of tumor prevention, by giving mAb before tumor transplantation, while a second series of experiments dealt with therapy of already established tumors. When mice received mAb 4.72 before they were challenged with MCA-1490 cells, tumor outgrowth commonly was delayed by a few days. These antitumor effects did not improve by increasing mAb dose; in fact, an experiment with a 100-fold increase in mAb dose showed accelerated tumor growth.

In a second set of experiments, we investigated the therapeutic value of injecting mice with established sarcomas intraperitoneally with the appropriate anti-idiotopic mAb. Injection of mAb 4.72 (but not of mAb 5.96) limited the growth of sarcoma MCA-1490 and, more importantly, it induced the regression of 3 out of 10 such sarcomas and prolonged the survival of the treated mice. Injection of mAb 5.96 (but not of mAb 4.72) had a similar effect in mice with sarcoma MCA-1511, also inducing regression of 3 out of 10 sarcomas.

9. ANTI-IDIOTYPIC ANTIBODY SPECIFIC TO AN IDIOTYPE WHICH RECOGNIZES A HUMAN MELANOMA-ASSOCIATED GD3 GANGLIOSIDE ANTIGEN

Mouse monoclonal antibody (mAb) MG-21 (Hellstrom et al., 1985, Proc. Natl. Acad. Sci. U.S.A. 82:1499–1502; see copending U.S. applications Ser. No. 831,684 filed Feb. 21, 1986, and Ser. No. 834,162 filed Feb. 26, 1986) recognizes a GD3 ganglioside antigen expressed on the surface of cells from most human melanomas and in trace amounts on normal cells (Dippold, W. G., et al., 1980, Proc. Natl. Acad. Sci. U.S.A. 77:6114–6118; Nudelman, E., et al., 1982, J. Biol. Chem. 257:12752–12756; Yeh, M. Y., et al., 1982, Int. J. Cancer 29:269–275). mAb MG-21 demonstrates complement-dependent cytotoxicity (CDC) to GD3-positive cells with human serum as the source complement, and antibody-dependent cellular cytotoxicity (ADCC) to GD3-positive cells with human lymphocytes (Hellstrom et al., 1985, supra). The GD3 antigen to which MG-21 binds has been used with some success as the target for a passively administered mouse mAb, R24 (Houghton, A. N., et al., 1985, Proc. Natl. Acad. Sci. U.S.A. 82:1242–1246), whose specificity and biological activity is similar to that of MG-21. As described in the examples infra, we have used MG-21 (Ab1) as an immunogen to generate a mouse monoclonal anti-idiotypic antibody (Ab2), which was designated 2C1. This mAb, which is an IgG2a, was selected by its capacity to inhibit the binding of MG-21 to a GD3-positive melanoma cell line. mAb 2C1 was found to bind to MG-21 with high avidity, but not to any of six other mouse mAb. It could completely abrogate the binding of MG-21 to GD3-positive melanoma cells as well as to purified GD3, and it inhibited the CDC and ADCC properties of MG-21 in a dose-dependent fashion. By using mAb 2C1 as a probe, an assay was developed to monitor human antibodies to mAb MG-21 in patients receiving mAb MG21 for therapeutic or diagnostic purposes. A detailed description of each step in this embodiment of the invention is presented in the subsections below.

9.1. MATERIALS AND METHODS

9.1.1. MICE

Eight to twelve week-old BALB/c female mice were purchased from the Animal Facilities of the Fred Hutchinson Cancer Research Center (Seattle, Wash.).

9.1.2. TARGET CELLS

Human melanoma cell line M-2669 clone 13 was used; for simplicity, it is referred to here as M-2669. It had been established from a metastatic melanoma and cloned (Beaumier, P. L., et al., 1986, J. Nucl. Med. 27:824–828). Cells from this clone strongly express the GD3 antigen defined by mAb MG-21 as determined by a binding assay (id.). The melanoma cells were grown in 6% $CO_2$ in air in RPMI 1640 culture medium (Gibco, Grand Island, N.Y.) containing 15% heat-inactivated fetal calf serum (Hyclone Laboratories, Inc., Logan, Utah) buffered with $NaHCO_3$ and supplemented with penicillin (100 U/ml), streptomycin (100 mg/ml) and L-glutamine (290 mg/liter).

9.1.3. GLYCOLIPID

GD3 ganglioside antigen was purified from M-2669 clone 13 melanoma cells as described (Nudelman, E., et al., 1982, J. Biol. Chem. 257:12752–12756), and was provided by Dr. Sen-itiroh Hakomori at Fred Hutchinson Cancer Research Center (Seattle, Wash.).

9.1.4. MONOCLONAL ANTIBODIES

MG-21 (Hellstrom, I., et al., 1985, Proc. Natl. Acad. Sci. U.S.A. 82:1499–1502) is an IgG3 antibody which binds to a GD3 ganglioside antigen expressed strongly on about 80–90% of human melanomas (Nudelman, E., et al., 1982, J. Biol. Chem. 257:12752–12756; Yeh, M.-Y., 1982, Int. J. Cancer 29:269–275). MG-21 can mediate CDC in the presence of human serum and ADCC in the presence of human peripheral blood lymphocytes (PBL), and it can inhibit the outgrowth of human melanoma xenografts in nude mice (Hellstrom, I., et al., 1985, Proc. Natl. Acad. Sci. U.S.A. 82:1499–1502).

mAb 2A-14 is an IgG3 which also binds to the GD3 ganglioside antigen, but to an epitope which by cross-blocking experiments appears to be different from that recognized by MG-21.

mAb 96.5 is an IgG2a which binds to p97, a melanoma-associated cell surface glycoprotein (Brown, J. P., et al., 1981, J. Immunol. 127:539–546; see copending U.S. patent applications Ser. No. 827,313, filed Feb. 7, 1986 and Ser. No. 007,230, filed Jan. 27, 1987).

mAb L6 is an IgG2a which binds to a carbohydrate antigen expressed strongly on cells from most human carcinomas but not melanomas (Hellstrom, I., et al., 1986, Cancer Res. 46:3917–3923; see copending U.S. patent applications Ser. No. 684,759, filed Dec. 21, 1984 and Ser. No. 776,321, filed Oct. 18, 1985).

mAb L20 is in IgG1 which identifies a 110 kd protein expressed on the surface of cells from most human carcinomas but not melanomas (id.).

mAb 7T1.1 is an IgG3 immunoglobulin specific for blood group A antigen strongly expressed on many human carcinomas.

mAb 1G3.10 is an IgG3 antibody specific for blood group A-like antigen also expressed on many human carcinomas.

mAb 26.8, which was used as an Ab2 control, is an IgG1 which binds to an idiotope on mAb 96.5 specific for the p97 melanoma antigen. mAb 26.8 can inhibit the binding of mAb 96.5 to p97.

P1.17 is an IgG2a mouse myeloma protein which was obtained from the American Type Culture Collection (ATCC Accession No. TIB 10).

Antibodies were purified either from spent culture medium or ascitic fluid by affinity chromatography on protein A-Sepharose CL-4B as described by Ey et al. (1978, Immunochemistry 15:429–436).

9.1.5. COUPLING OF ANTIBODY WITH KEYHOLE LIMPET HEMOCYANIN

Antibody MG-21 was coupled to keyhole limpet hemocyanin (KLH) by chemical cross-linking in the presence of glutaraldehyde according to the procedures of Bona et al. (1979, J. Exp. Med. 149:815–823). In brief, 1 ml of mAb MG-21 solution (3.6 mg/ml) was mixed with 1 ml of KLH solution (3 mg/ml) in 0.1M phosphate buffer, pH 7.5. Coupling was initiated by the addition of 1 ml of a 0.25% solution of glutaraldehyde (Sigma Chemical, St. Louis, Mo.). The mixture was shaken at room temperature for 1 hour. The reaction was stopped by adding 250 ul of 1M glycine. Antibody-KLH conjugate was stored frozen at –20° C. before use.

9.1.6. PRODUCTION OF MONOCLONAL ANTI-IDIOTYPIC ANTIBODIES (Ab2) SPECIFIC FOR MG-21 (Ab1)

Two 8-week-old BALB/c female mice were immunized intraperitoneally (i.p.) with 100 ug of MG-21-KLH conjugate in complete Freund's adjuvant. Two weeks later, the same amount of conjugate was given i.p. in incomplete Freund's adjuvant. Another 8 weeks later, the mice were boosted again with conjugate in saline. Four days after the last immunization, spleens were removed and the harvested cells were fused with NS-1 mouse myeloma cells by use of polyethylene glycol. Hybridomas secreting anti-idiotypic antibodies specific for MG-21 were selected, grown in HAT medium, and cloned using established procedures (Yeh, M.-Y., et al., 1979, Proc. Natl. Acad. Sci. U.S.A. 76:2927–2931).

9.1.7. mAb (Ab1) BINDING INHIBITION ASSAY

Enzyme-linked immunosorbent assays (ELISAs) of antibody binding were used for the initial screening of hybridomas secreting anti-idiotypic antibodies. In this assay, hybridoma culture supernatants were tested for inhibition of binding of MG-21 ("Ab1") to M-2669 cells, as evidence for the presence of anti-idiotypic antibodies ("Ab2"). M-2669 melanoma cells, seeded into polyvinyl chloride plates ($10^5$ cells/well) and fixed with 0.5% glutaraldehyde, were used as targets. One hundred ul of mAb MG-21 (5 ug/ml) were mixed with equal volumes of hybridoma supernatants, incubated at 4° C. for 2–4 hours, and then added to the target cells. After another incubation for 1 hour at 37° C., the plates were washed three times with 0.05% Tween-20 in PBS (PBS-Tween buffer). The cells were then incubated with 100 ul of goat anti-mouse IgG antibody-peroxidase conjugate (Boehringer Mannheim Biochemicals, Indianapolis, Ind.) diluted 1/10,000 in PBS-Tween buffer at 37° C. for 30 minutes, and washed again. One hundred ul of o-phenylenediamine (OPD) containing 0.015% $H_2O_2$ in citrate phosphate, pH 5.0, were dispensed in each well as substrate for peroxidase. About 3–5 minutes later, 100 ul of 1.3N $H_2SO_4$ were added for blocking the enzyme-substrate reaction. Absorbance was measured at 492 nm/630 nm dual wavelength for each well in a GSC microplate reader (Genetic System Corp., Seattle, Wash.).

To investigate the dose-dependency of the inhibitory effect of anti-idiotypic antibody (Ab2) on the binding of MG-21 (Ab1) to cells and GD3 antigen, 100 ul of a fixed concentration (5 ug/ml) of MG-21 were mixed with 100 ul of various concentrations of appropriate anti-idiotypic or control antibodies, incubated at 37° C. for 1 hour, and then added to wells precoated with M-2669 cells ($10^5$/well) or purified GD3 antigen (200 ng/50 ul/well). The remaining procedures were the same as those above.

9.1.8. DETERMINATION OF IMMUNOGLOBULIN ISOTYPE

Goat antisera to the specific class of mouse immunoglobulin were used (Southern Biotechnology Assoc., Birmingham, Ala.). Fifty ul of each such anti-serum was diluted in PBS (1 ul/ml), plated into 96-well plates (Dynatech, Alexandria, Va.), and incubated overnight at 4° C. The plates were washed once with PBS-Tween buffer, and then incubated for 1 hour at room temperature with 100 ul per well of RPMI 1640 medium containing 15% fetal calf serum (FCS). After washing, 50 ul of hybridoma spent culture medium were added, followed by incubation of the plates at room temperature for 1 hour and one washing with PBS-Tween buffer. Subsequently, 50 ul of goat anti-mouse IgG antibody conjugate diluted 1/10,000 in PBS-Tween buffer were added to each well. The plates were incubated for 30 minutes at 37° C. and washed five times with PBS-Tween buffer, after which 100 ul of OPD substrate were added to each well. Five minutes later, the reaction was stopped by adding 100 ul of 1.3N $H_2SO_4$, and the absorbance was measured in a GSC microplate reader.

9.1.9. ANTI-IDIOTYPIC ANTIBODY (Ab2) BINDING ASSAY

A binding assay was used to determine whether the ability of Ab2 to inhibit the binding of MG-21 (Ab1) was specific. Purified MG-21 at 0.5 ug/100 ul was added to coat each well of 96-well polyvinyl chloride plates (Costar, Cambridge, Mass.), after which 200 ul per well of RPMI 1640 medium containing 15% FCS was added as a "blocker" to prevent antibody binding to plastic. After washing, 100 ul of purified Ab2 or control immunoglobulin P1.17 were added at various concentrations. The plates were incubated at 37° C. for 30 minutes, and then washed three times with PBS-Tween buffer. One hundred ul of peroxidase-conjugated rabbit anti-mouse IgG which had the same isotype as the Ab2 were then added after dilution in PBS-Tween buffer. After incubation for 30 minutes at 37° C., followed by extensive washing, 100 ul of OPD substrate were added and incubated for 3–5 minutes in the dark. Finally, 100 ul of 1.3N $H_2SO_4$ were added. The plates were read by a GSC microplate reader.

9.1.10. RADIOIODGATION OF ANTIBODY AND DIRECT $^{125}$I-Ab2 BINDING ASSAY

One hundred ug of purified mAb were incubated with 500 uCi Na$^{125}$I (Amersham Corporation, Arlington Heights, Ill.) and 40 ug of chloramine-T in 500 ul of PBS at 4° C. for three minutes. Labeled mAb was separated from free $^{125}$I by gel filtration on a column of Sephadex G-25; the specific activity was approximately $4 \times 10^6$ cpm/ug. The labeled mAb was diluted in 15% FCS in PBS before use.

For a direct $^{125}$I-Ab2 binding assay, 100 ul of various purified mAb (50 ug/ml) in 15 mM NaHCO$_3$ at pH 9 were plated into 96-well plates (Dynatech, Alexandria, Va.) at 4° C. overnight. After washing, the wells were blocked by incubation overnight at 4° C. with 200 ul of RPMI 1640 medium containing 15% FCS. The plates were washed three times with PBS-Tween buffer, and $2.5 \times 10^5$ cpm of labeled Ab2 in 100 ul of 30% FCS were added to each well and incubated at room temperature for 1 hour. After thorough washing, the bound radioactivity was dissolved in 100 ul of 2M NaOH, transferred to test tubes, and counted in a Gamma counter (Beckman, Irvine, Calif.).

9.1.11. ANTIBODY-FITC CONJUGATION

Fluorescein isothiocyanate (FITC) was conjugated to mAb MG-21 as described by Goding (Goding, J. W., 1976, J. Immunol. Methods 13:215–226). Briefly, 2 mg of purified MG-21 was dialyzed overnight in 0.2M carbonate/bicarbonate buffer, pH 9.5. FITC (Molecular Probes Inc., Junction City, Oreg.) dissolved in dimethyl sulfoxide (1 mg/ml) was added at a ratio of 40 ug FITC/mg of antibody. The mixture was incubated at 37° C. for 45 minutes, after which conjugated mAb was separated from free FITC by passage through a G-25 Sephadex column equilibrated with PBS containing 0.1% NaN$_3$. The fluorescein/antibody conjugation ratio was about 3.5 to 4.0. The conjugated mAb was stored at −20° C. in PBS containing 1% bovine serum albumin (BSA).

9.1.12. FLUORESCENCE ACTIVATED CELL SORTER ANALYSIS

For binding inhibition analysis using a fluorescence activated cell sorter (FACS), 100 ul of FITC-conjugated MG-21 were incubated for 30 minutes at 37° C. with 100 ul of various concentrations of purified Ab2 or control antibodies in 10% normal mouse serum. The antibody mixtures were then added to test tubes containing $1 \times 10^6$ paraformaldehyde-fixed M-2669 cells in 100 ul of PBS. After 30 minutes of incubation, the cells were washed two times with PBS, and then analyzed with a Coulter Epics C fluorescence activated cell sorter (Coulter Corporation, Hialeah, Fla.). Data were expressed as linear fluorescent equivalence (LFE), which represents relative fluorescent intensity.

9.1.13. COMPLEMENT-DEPENDENT CYTOTOXICITY ASSAY

To test whether Ab2 specific for MG-21 can inhibit complement-dependent cytotoxicity (CDC) of mAb MG-21, a 4-hour $^{51}$Cr-release assay (Hellstrom, I., et al., 1985, Proc. Natl. Acad. Sci. U.S.A. 82:1499–1502) was used. Briefly, $10^6$ target cells were labeled with 100 uCi of $^{51}$Cr for 2 hours at 37° C. After labelling, the cells were washed three times, resuspended in RPMI 1640 medium containing 15% FCS, and 20,000 labeled cells, suspended in 45 ul of RPMI 1640 medium, and seeded into each well of Microtiter V-bottom plates (Dynatech Laboratories, Alexandria, Va.). Various concentrations of purified MG-21 were combined with different concentrations of purified Ab2 (or control mAb) to test for inhibition of CDC. They were added in 90 ul per well, followed by 65 ul of undiluted unheated human serum per well. After incubation for 4 hours at 37° C., the plates were centrifuged at 400×g, 100 ul of supernatants from each well were removed, and the level of radioactivity was determined by a Gamma counter (Beckman, Irvine, Calif.). Spontaneous release was defined as the cpm released into the medium from target cells which had not been exposed to antibody or complement, and total release was estimated as the cpm released from target cells that were osmotically lysed. Percent cytotoxicity was calculated by the following formula:

$$\text{Percent cytotoxicity} = \frac{\text{Experimental release} - \text{Spontaneous release}}{\text{Total release} - \text{Spontaneous release}} \times 100$$

9.1.14. ANTIBODY-DEPENDENT CELLULAR CYTOTOXICITY ASSAY

To test whether Ab2 can inhibit the antibody-dependent cellular cytotoxicity (ADCC) of mAb MG-21, a 4-hour release assay was employed. PBL from healthy human subjects were used as effector cells. They were separated on Ficoll-Hypaque and prescreened for low natural killer (NK) cell activity. Only lymphocytes with low NK activity (less than 10% $^{51}$Cr-release over four hours) were used. After labeling of the target cells, they were plated ($2 \times 10^4$ cells/50 ul) into Microtiter plates as for the CDC assay. Fifty ul of purified MG-21 and 50 ul of purified Ab2 (or control) mAb were added at various concentrations, followed by $2 \times 10^6$ lymphocytes per well in 50 ul of medium; the ratio of lymphocytes to target cells was 100:1. The mixtures were incubated for 4 hours at 37° C. in a 6% $CO_2$ in air atmosphere. Subsequently, the plates were centrifuged, and 100 ul of supernatants were transferred from each well for radioactivity measurement. Percent cytotoxicity was calculated as for the CDC assay.

9.1.15. COMPETITION ASSAY FOR DETECTING ANTI-MG-21 ANTIBODIES IN PATIENT SERA

A competition assay using monoclonal anti-idiotypic antibody (Ab2) as a probe was developed for detecting anti-MG-21 antibodies in the sera of patients treated with mAb MG-21. Briefly, 100 ul of Ab2 (5 ug/ml) in 15 mM $NaHCO_3$ buffer, pH 9, were added to each well of Falcon pro-bind assay plates (Becton Dickinson, Oxnard, Calif.), incubated at room temperature for 1 hour, and subsequently washed with PBS-Tween buffer. Seventy-five ul of mAb MG-21 (1 ug/ml) were preincubated for 45 minutes with equal volumes of sera from a patient or with pooled normal human serum; the sera were diluted 1:2.5, 1:5 and 1:10 in PBS. Subsequently, 100 ul of the mixtures were added to the Ab2-precoated plates. After an additional incubation for 30 minutes at room temperature, the plates were washed twice with PBS-Tween buffer. One hundred ul of rabbit anti-mouse IgG3 antibody-peroxidase conjugate (Zymed Laboratories Inc., South San Francisco, Calif.), diluted 1:1,000 in PBS-Tween buffer, were added and incubated for 30 minutes at room temperature. After three washes with PBS-Tween buffer, the wells were filled with 100 ul of OPD substrate containing 0.015% $H_2O_2$ in citrate phosphate, pH 5.0. Five minutes later, 100 ul of 1.3N $H_2SO_4$ were added, and the plates were read by a GSC microplate reader. Percentage of inhibition of MG-21 binding to mAb 2C1 was calculated by the following formula:

$$\text{Percent inhibition} = \left(1 - \frac{\text{OD in the presence of patient serum}}{\text{OD in the presence of normal human serum}}\right) \times 100$$

Serum samples from three of eight patients with advanced melanoma, which were enrolled in a phase I trial of mAb MG-21, were tested by this assay. Briefly, MG-21 in 5% human serum albumin had been infused to these patients over a 4–6 hour time period with the infusions being repeated daily for 7 days. The serum samples were taken prior to treatment and at various intervals after, and were stored at −80° C. until analysis.

9.2. RESULTS

9.2.1. SELECTION OF HYBRIDOMAS

Spleen cells from mice immunized with MG-21 were fused with NS-1 cells to generate hybridomas which could produce Mab to idiotypic determinants on MG-21; the latter mAb are referred to as Ab2. Two weeks after fusion, hybridoma supernatants were tested for antibodies inhibiting the binding of MG-21 to M-2669 cells. One hybridoma, 2C1, which had such activity, was cloned and expanded. As shown in FIG. 8, supernatant of the 2C1 hybridoma strongly inhibited the binding of MG-21 to M-2669 cells but did not itself bind to M-2669 cells. Supernatant from the NS-1 myeloma was used as a control and did not inhibit the binding of MG-21.

Hybridoma 2C1 grew as an ascites tumor, when inoculated intraperitoneally into pristane-primed BALB/c mice. mAb 2C1 was found to be an IgG2a by solid phase enzyme immunoassay with goat anti-mouse Ig specific class antisera.

As shown in FIG. 9, mAb 2C1 gave strong binding to MG-21 when tested in an ELISA at concentrations between 0.08 ug/ml and 2 ug/ml with significant binding still being observed at 6.4 ng/ml. No binding was seen to P1.17, an IgG2a myeloma protein (FIG. 9).

9.2.2. mAb 2C1 IS SPECIFIC FOR MG-21

To determine the degree of specificity of 2C1 for MG-21, a binding assay was performed using $^{125}$I-labeled 2C1. Six mouse mAbs, which had been generated against a variety of human tumors, were included as controls. As shown in FIG. 10, mAb 2C1 bound strongly to MG-21 but not to any of the six control mAbs, two of which (2A-14 and 96.5) were specific for melanoma-associated antigens that were different from the epitope recognized by MG-21. Of these two mAb, 2A-14 reacts with an epitope of the GD3 antigen which is different from that recognized by MG-21.

9.2.3. mAb 2C1 (Ab2) INHIBITS THE BINDING OF MG-21 (Ab1) TO M-2669 CELLS AND GD3 ANTIGEN IN A DOSE-DEPENDENT MANNER

A binding assay was used to titrate how much mAb 2C1 was required as Ab2 to inhibit the binding of MG-21 (Ab1) to M-2669 cells. As shown in Table XX, mAb 2C1 completely inhibited the binding of MG-21 to M-2669 cells when present at a concentration equal to or greater than that of MG-21; two control immunoglobulins, mAb 26.8 and P1.17, gave no significant inhibition.

TABLE XX

DOSE-DEPENDENT INHIBITORY EFFECT OF mAb 2C1 ON THE BINDING OF mAb MG-21 TO M-2669 CELLS

| Antibody 1 concentration | Antibody 2 concentration | Absorbance at 492/630 nm[1] |
|---|---|---|
| MG-21 (2.5 ug/ml) | None | 6.324 ± 0.015[2] |
| MG-21 (2.5 ug/ml) | mAb 2C1 (10 ug/ml) | 0.071 ± 0.029* |
| MG-21 (2.5 ug/ml) | mAb 2C1 (5 ug/ml) | 0.043 ± 0.026* |
| MG-21 (2.5 ug/ml) | mAb 2C1 (2.5 ug/ml) | 0.053 ± 0.002* |
| MG-21 (2.5 ug/ml) | mAb 2C1 (1.25 ug/ml) | 0.129 ± 0.019** |
| MG-21 (2.5 ug/ml) | mAb 2C1 (0.625 ug/ml) | 0.156 ± 0.023** |
| MG-21 (2.5 ug/ml) | mAb 26.8 (10 ug/ml) | 0.305 ± 0.007 |
| MG-21 (2.5 ug/ml) | mAb 26.8 (5 ug/ml) | 0.329 ± 0.035 |
| MG-21 (2.5 ug/ml) | mAb 26.8 (2.5 ug/ml) | 0.315 ± 0.024 |
| MG-21 (2.5 ug/ml) | mAb 26.8 (1.25 ug/ml) | 0.337 ± 0.035 |
| MG-21 (2.5 ug/ml) | mAb 26.8 (0.625 ug/ml) | 0.330 ± 0.036 |
| MG-21 (2.5 ug/ml) | P1.17 (10 ug/ml) | 0.322 ± 0.049 |
| MG-21 (2.5 ug/ml) | P1.17 (5 ug/ml) | 0.368 ± 0.019 |
| MG-21 (2.5 ug/ml) | P1.17 (2.5 ug/ml) | 0.331 ± 0.019 |
| MG-21 (2.5 ug/ml) | P1.17 (1.25 ug/ml) | 0.318 ± 0.035 |
| MG-21 (2.5 ug/ml) | P1.17 (0.625 ug/ml) | 0.318 ± 0.031 |

[1]Data are presented as mean ± SE.
[2]Control
Differences statistically significant from control without Ab2,
*, P less than 0.01; **, P less than 0.025.

In a parallel study, purified GD3, which is the antigen recognized by MG-21, was used instead of M-2669 cells. mAb 2C1 inhibited the binding of MG-21 to the purified GD3 ganglioside in a dose-dependent manner (Table XXI).

TABLE XXI

DOSE-DEPENDENT INHIBITORY EFFECT OF mAb 2C1 ON THE BINDING OF mAb MG-21 TO GD3 GANGLIOSIDE ANTIGEN

| Antibody 1 concentration | Antibody 2 concentration | Absorbance at 490 nm/630 NM[1] |
|---|---|---|
| MG-21 (2.5 ug/ml) | None | 0.486 ± 0.092[2] |
| MG-21 (2.5 ug/ml) | mAb 2C1 (25 ug/ml) | 0.085 ± 0.006* |
| MG-21 (2.5 ug/ml) | mAb 2C1 (12.5 ug/ml) | 0.073 ± 0.010* |
| MG-21 (2.5 ug/ml) | mAb 2C1 (6.25 ug/ml) | 0.075 ± 0.008* |
| MG-21 (2.5 ug/ml) | mAb 2C1 (3.125 ug/ml) | 0.379 ± 0.009 |
| MG-21 (2.5 ug/ml) | mAb 2C1 (1.563 ug/ml) | 0.502 ± 0.075 |
| MG-21 (2.5 ug/ml) | mAb 2C1 (0.782 ug/ml) | 0.482 ± 0.033 |
| MG-21 (2.5 ug/ml) | mAb 2C1 (0.391 ug/ml) | 0.533 ± 0.078 |

1Data are presented as mean ± SE.
[2]Control
Differences statistically significant from control without Ab2,
*, P less than 0.01.

The inhibitory effect of mAb 2C1 on the binding of MG-21 to M-2669 cells was confirmed by FACS analysis using FITC-conjugated MG-21. Starting with 40 ug/ml of FITC-conjugated MG-21, which approximately corresponded to the saturation concentration, excess amounts of mAb 2C1 or control antibodies were added to M-2669 cells. FIG. 11 shows that 2C1 completely inhibited the binding of FITC-conjugated MG-21 to the tumor cells, while control antibodies had no effect.

9.2.4. ANTIBODY 2C1 INHIBITS THE CDC AND ADCC ACTIVITY OF MG-21 AGAINST M-2669 CELLS

Previous experiments have shown that MG-21 gives strong CDC and ADCC with GD3-positive melanoma cells (Hellstrom, I., et al., 1985, Proc. Natl. Acad. Sci. U.S.A. 82:1499–1502). We now tested whether 2C1 had any effect on these activities. As shown in Table XXII, CDC of MG-21 was completely abrogated by adding mAb 2C1 at a concentration greater than that of MG-21, but not by adding either of two control antibodies, mAb 26.8 or P1.17.

TABLE XXII

INHIBITION OF CDC OF mAb MG-21 AGAINST M-2669 CELLS BY mAb 2C1

| Antibody 1 Final Concentration | Antibody 2 Final Concentration | Cytotoxicity[1] % |
|---|---|---|
| MG-21 (5 ug/ml) | None | 100 (Control) |
| MG-21 (5 ug/ml) | mAb 2C1 (10 ug/ml) | |
| MG-21 (5 ug/ml) | mAb 2C1 (1 ug/ml) | 84 |
| MG-21 (5 ug/ml) | mAb 2C1 (0.1 ug/ml) | 100 |
| MG-21 (5 ug/ml) | mAb 26.8 (10 ug/ml) | 100 |
| MG-21 (5 ug/ml) | mAb 26.8 (1 ug/ml) | 100 |
| MG-21 (5 ug/ml) | P1.17 (10 ug/ml) | 100 |
| MG-21 (5 ug/ml) | P1.17 (1 ug/ml) | 100 |
| MG-21 (1 ug/ml) | None | 64 (Control) |
| MG-21 (1 ug/ml) | mAb 2C1 (10 ug/ml) | 1* |
| MG-21 (1 ug/ml) | mAb 2C1 (1 ug/ml) | 0* |
| MG-21 (1 ug/ml) | mAb 2C1 (0.1 ug/ml) | 56 |
| MG-21 (1 ug/ml) | mAb 26.8 (10 ug/ml) | 69 |
| MG-21 (1 ug/ml) | mAb 26.8 (1 ug/ml) | 60 |
| MG-21 (1 ug/ml) | P1.17 (10 ug/ml) | 67 |
| MG-21 (1 ug/ml) | P1.17 (1 ug/ml) | 69 |

[1]Cytotoxicity was determined in a 4-hour $^{51}$Cr-release assay using normal human serum as a source of complement. No cytotoxicity was seen with human serum alone. Antibodies alone did not give any cytotoxicity. Significance was determined by student's t-test and is indicated by *, P less than 0.01.

Antibody 2C1 also completely inhibited the ADCC activity of MG-21 against M-2669 cells when its concentration was greater than that of MG-21, while no significant inhibition was seen with the two control antibodies (Table XXIII).

TABLE XXIII

INHIBITION OF ADCC OF mAb MG-21 AGAINST M-2669 CELLS BY mAb 2C1

| Antibody 1 Final Concentration | Antibody 2 Final Concentration | Cytotoxicity[1] % |
|---|---|---|
| MG-21 (5 ug/ml) | None | 40 (Control) |
| MG-21 (5 ug/ml) | mAb 2C1 (10 ug/ml) | 4* |
| MG-21 (5 ug/ml) | mAb 2C1 (1 ug/ml) | 16* |
| MG-21 (5 ug/ml) | mAb 2C1 (0.1 ug/ml) | 33 |
| MG-21 (5 ug/ml) | mAb 26.8 (10 ug/ml) | 44 |
| MG-21 (5 ug/ml) | mAb 26.8 (1 ug/ml) | 40 |
| MG-21 (5 ug/ml) | P1.17 (10 ug/ml) | 34 |
| MG-21 (5 ug/ml) | P1.17 (1 ug/ml) | 39 |
| MG-21 (1 ug/ml) | None | 32 (Control) |
| MG-21 (1 ug/ml) | mAb 2C1 (10 ug/ml) | 7* |
| MG-21 (1 ug/ml) | mAb 2C1 (1 ug/ml) | 3* |
| MG-21 (1 ug/ml) | mAb 2C1 (0.1 ug/ml) | 16* |

TABLE XXIII-continued

INHIBITION OF ADCC OF mAb MG-21
AGAINST M-2669 CELLS BY mAb 2C1

| Antibody 1<br>Final Concentration | Antibody 2<br>Final Concentration | Cytotoxicity[1]<br>% |
|---|---|---|
| MG-21 (1 ug/ml) | mAb 26.8 (10 ug/ml) | 26 |
| MG-21 (1 ug/ml) | mAb 26.8 (1 ug/ml) | 23 |
| MG-21 (1 ug/ml) | P1.17 (10 ug/ml) | 28 |
| MG-21 (1 ug/ml) | P1.17 (1 ug/ml) | 23 |

[1]Cytotoxicity was determined in a 4-hour $^{51}$Cr-release assay using normal human peripheral blood lymphocytes as effectors. The ratio of effector cells to target cells was 100:1. Antibodies alone gave no cytotoxicity and lymphocytes alone gave 6.9% cytotoxicity. Significant differences compared to control without Ab2 were calculated by student's t-test, *, P less than 0.01.

9.2.5. DETECTION OF ANTI-MG-21 ANTIBODIES IN PATIENT SERA USING mAb 2C1 AS A PROBE

Since mAb 2C1 is specific for MG-21, it can be used as a reagent for detecting human anti-MG-21 antibodies in the sera of patients treated with MG-21. A competition assay was developed (see Section 9.1.15., supra), by which we tested whether sera from any of 3 patients injected with MG-21 inhibited the binding of MG-21 to mAb 2C1. As shown in Table XXIV, sera obtained from all these three patients 17, 18 or 21 days, respectively, (or later) after administration of MG-21, strongly inhibited the binding of MG-21 to mAb 2C1 with 20–83%. The pretreatment sera gave less than 13% inhibition as compared to pooled normal human serum.

TABLE XXIV

INHIBITION OF BINDING OF mAb MG-21 TO mAb 2C1
BY SERA FROM PATIENTS RECEIVING mAb MG-21

| Patient<br>No. | Dose of MG-21/day<br>for 7 Days* | Days After<br>Start of mAb<br>Treatment | % Inhibition of Binding | | |
|---|---|---|---|---|---|
| | | | 1:2.5** | 1:5 | 1:10 |
| 1 | 5 mg/M²/day | 0 | 0 | 0 | 0 |
| | | 14 | 58 | 53 | 33 |
| | | 18 | 60 | 58 | 43 |
| | | 24 | 65 | 62 | 47 |
| | | 28 | 83 | 87 | 85 |
| 2 | 5 mg/M²/day | 0 | 10 | 12 | 0 |
| | | 21 | 55 | 46 | 31 |
| | | 28 | 53 | 32 | 25 |
| | | 49 | 62 | 46 | 20 |
| | | 61 | 59 | 32 | 27 |
| 3 | 50 mg/M²/day | 0 | 6 | 13 | 2 |
| | | 18 | 28 | 21 | 20 |
| | | 28 | 30 | 30 | 26 |
| | | 45 | 45 | 31 | 15 |
| | | 66 | 77 | 60 | 45 |
| | | 127 | 73 | 50 | 43 |

*Patient received 4–6 hour infusion of MG-21 daily for 7 days in dose noted. Serum samples were drawn at various times after the start of treatment.
**Serum samples were diluted 1:2.5, 1:5 and 1:10 in PBS.

The anti-idiotypic mAb antibody 2C1, which we describe here, recognizes an idiotype specific to a human melanoma-associated GD3 ganglioside antigen. mAb 2C1 was shown to bind to mAb MG-21 even at a low concentration (0.08 ug/ml), but not to other tAb of the same or different isotypes. It inhibited, in a dose-dependent manner, the binding of MG-21 to the GD3 ganglioside antigen as well as to GD3-positive M-2669 melanoma cells. Furthermore, mAb 2C1 completely abrogated the CDC and ADCC activities of mAb MG-21, as long was its concentration was greater than that of MG-21.

Using mAb 2C1 as a probe, we have developed an assay for human anti-MG-21 antibodies in the sera of patients treated with MG-21. Analogous assays may be developed for other types of anti-tumor antibodies. Since human antibodies binding to MG-21 were present at short times (14–21 days) after treatment of patients with MG-21, unless such antibodies are highly effective in inducing an immune response leading to tumor rejection, procedures minimizing such antibody development can be envisioned for use when prolonged treatment of patients by administered anti-tumor antibodies is desired.

10. DEPOSIT OF MICROORGANISMS

Hybridoma cell line 2C1, producing monoclonal antibody 2C1, has been deposited with the American Type Culture Collection, Rockville, Md., and has been assigned accession number HB 9484.

The present invention is not to be limited in scope by the cell line deposited since the deposited embodiment is intended as a single illustration of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

What is claimed is:

1. An adoptive immunotherapeutic method for increasing cell-mediated cytotoxicity specific for a syngeneic bladder carcinoma, fibrosarcoma, lung carcinoma or melanoma in vivo, comprising selecting histocompatible tumor-reactive helper and/or cytotoxic T cells using a monoclonal anti-idiotypic antibody, expanding the cells in culture, and administering a dosage of the T cells that express an idiotype that is directed against an immunochemically defined antigen specific for the bladder carcinoma, fibrosarcoma, lung carcinoma or melanoma, which antigen comprises a tumor-associated antigen selected from the group consisting of oncofetal and differentiation antigens, and which dosage is effective in transferring cell-mediated cytotoxicity to the antigen-expressing bladder carcinoma, fibrosarcoma, lung carcinoma or melanoma, as measured by a positive result using either of the following assays in which the antigen is employed: a leukocyte adherence inhibition assay, and a delayed type hypersensitivity assay.

2. The method according to claim 1 in which the tumor specific antigen comprises an oncofetal antigen.

3. An adoptive immunotherapeutic method for increasing cell-mediated cytotoxicity specific for a syngeneic melanoma in vivo, comprising selecting histocompatible melanoma-reactive helper and/or cytotoxic T cells using a monoclonal anti-idiotypic antibody, expanding, the cells in culture, and administering a dosage of the T cells that express an idiotype that is directed against an immunochemically defined melanoma antigen specific for a tumor, and which dosage is effective in transferring cell-mediated cytotoxicity to the antigen-expressing tumor cells, as measured by a positive result using either of the following assays in which the antigen is employed: a leukocyte adherence inhibition assay, and a delayed type hypersensitivity assay.

4. The method according to claim 3 in which the melanoma antigen comprises p97.

5. The method according to claim 3 in which the melanoma antigen comprises GD3.

6. An adoptive immunotherapeutic method for increasing cell-mediated cytotoxicity specific for a syngeneic lung carcinoma in vivo, comprising selecting histocompatible lung carcinoma-reactive helper and/or cytotoxic T cells using a monoclonal anti-idiotypic antibody, expanding the cells in culture, and administering a dosage of the T cells that express an idiotype that is directed against an immunochemically defined lung carcinoma antigen specific for a tumor, and which dosage is effective in transferring cell-mediated cytotoxicity to the antigen-expressing tumor cells, as measured by a positive result using either of the following assays in which the antigen is employed: a leukocyte adherence inhibition assay, and a delayed type hypersensitivity assay.

7. The method according to claim 6 in which the lung carcinoma antigen comprises L6.

8. The method according to claim 8 in which the lung carcinoma antigen comprises L20.

9. An adoptive immunotherapeutic method for increasing cell-mediated cytotoxicity specific for a syngeneic oncofetal bladder carcinoma in vivo, comprising selecting histocompatible oncofetal bladder carcinoma-reactive helper and/or cytotoxic T cells using a monoclonal anti-idiotypic antibody, expanding the cells in culture, and administering a dosage of the T cells that express an idiotype that is directed against an immunochemically defined oncofetal bladder tumor antigen specific for a tumor, and which dosage is effective in transferring cell-mediated cytotoxicity to the antigen-expressing tumor cells, as measured by a positive result using either of the following assays in which the antigen is employed: a leukocyte adherence inhibition assay, and a delayed type hypersensitivity assay.

10. An adoptive immunotherapeutic method for increasing cell mediated cytotoxicity specific for a syngeneic fibrosarcoma in vivo, comprising selecting histocompatible fibrosarcoma-reactive helper and/or cytotoxic T cells using a monoclonal anti-idiotypic antibody, expanding the cells in culture, and administering a dosage of the T cells that express an idiotype that is directed against an immunochemically defined fibrosarcoma antigen specific for a tumor, and which dosage is effective in transferring cell-mediated cytotoxicity to the antigen-expressing tumor cells, as measured by a positive result using either of the following assays in which the antigen is employed: a leukocyte adherence inhibition assay, and a delayed type hypersensitivity assay.

11. An immunotherapeutic method for increasing cell-mediated cytotoxicity specific for a syngeneic tumor in vivo, wherein the tumor is a bladder carcinoma, a lung carcinoma, a fibrosarcoma or a melanoma, comprising:

(a) isolating tumor reactive lymphocytes from a patient who has been immunogenically exposed to (i) an antigen specific for the tumor, or (ii) a monoclonal anti-idiotypic antibody that specifically recognizes an idiotype that is directed against an immunochemically defined antigen specific for the tumor, which antigen comprises a tumor-associated antigen selected from the group consisting of oncofetal and differentiation antigens, which idiotype is present on a second antibody molecule or on a T lymphocyte or on an immune suppressor factor;

(b) stimulating the lymphocytes in vitro by exposing the lymphocytes to the monoclonal anti-idiotypic antibody, (c) selecting and expanding the lymphocytes in step (b); and (d) injecting an effective dosage of the lymphocytes of step (c) into a patient who has the tumor and who is histocompatible with the lymphocytes.

12. The method according to claim 11 in which the tumor specific antigen comprises an oncofetal antigen.

13. The method according to claim 12 in which the oncofetal antigen comprises a melanoma antigen.

14. The method according to claim 13 in which the melanoma antigen comprises p97.

15. The method according to claim 13 in which the melanoma antigen comprises GD3.

16. The method according to claim 15 in which the monoclonal anti-idiotypic antibody comprises monoclonal antibody 2C1, as deposited with the ATCC and assigned accession number HB 9484.

17. The method according to claim 12 in which the oncofetal antigen comprises a lung carcinoma antigen.

18. The method according to claim 17 in which the lung carcinoma antigen comprises L6.

19. The method according to claim 17 in which the lung carcinoma antigen comprises L20.

20. The method according to claim 12 in which the oncofetal antigen comprises an oncofetal bladder tumor antigen.

21. The method according to claim 11 in which the tumor specific antigen comprises a fibrosarcoma antigen.

* * * * *